United States Patent [19]

Geiger et al.

[11] Patent Number: 5,401,766

[45] Date of Patent: Mar. 28, 1995

[54] AMINOACID DERIVATIVES, A PROCESS FOR THEIR PREPARATION, AGENTS CONTAINING THESE COMPOUNDS, AND THE USE THEREOF

[75] Inventors: Rolf Geiger, Frankfurt am Main; Volker Teetz, Hofheim am Taunus; Hansjörg Urbach, Kronberg/Taunus; Bernward Schölkens, Kelkheim; Rainer Henning, Giessen, all of Germany

[73] Assignee: Hoechst Aktiengesellschaft, Frankfurt am Main, Germany

[21] Appl. No.: 208,443

[22] Filed: Mar. 9, 1994

Related U.S. Application Data

[63] Continuation of Ser. No. 297,191, Aug. 28, 1981, abandoned.

[30] Foreign Application Priority Data

Aug. 30, 1980 [DE] Germany ............... 30 32 709.4
May 8, 1981 [DE] Germany ............... 31 18 191.0

[51] Int. Cl.$^6$ ............... C07D 209/34; A61K 31/405
[52] U.S. Cl. ............... 514/307; 514/414; 514/235.2; 546/146; 546/147; 546/165; 548/491; 548/492
[58] Field of Search ............... 546/147, 165, 146; 514/414, 419; 548/492, 491; 424/274

[56] References Cited

U.S. PATENT DOCUMENTS

| | | | |
|---|---|---|---|
| 3,472,872 | 1/1969 | Bell ............... | 546/328 |
| 3,501,497 | 3/1970 | Bell ............... | 546/328 |
| 4,294,832 | 10/1981 | Yoneda et al. ............... | 514/147 |
| 4,303,583 | 12/1981 | Kim et al. ............... | 260/239.3 |
| 4,344,949 | 8/1982 | Hoefle et al. ............... | 546/147 |
| 4,350,633 | 9/1982 | Kim et al. ............... | 260/326.11 R |
| 4,350,704 | 9/1982 | Hoefle et al. ............... | 546/170 |
| 4,374,817 | 2/1983 | Gruenfeld ............... | 548/491 |
| 4,374,847 | 2/1983 | Gruenfeld et al. ............... | 548/491 |
| 4,404,206 | 9/1983 | Vincent et al. ............... | 546/147 |
| 4,404,206 | 9/1983 | Vincent et al. ............... | 424/258 |
| 4,431,644 | 2/1984 | Smith et al. ............... | 548/452 |
| 4,431,645 | 2/1984 | Smith et al. ............... | 544/13 |
| 4,468,396 | 8/1984 | Magatti ............... | 514/222 |
| 4,490,386 | 12/1984 | Seamans et al. ............... | 548/492 |
| 4,500,713 | 2/1985 | Suh et al. ............... | 546/165 |
| 4,508,729 | 4/1985 | Vincent et al. ............... | 514/419 |
| 4,512,979 | 4/1985 | Ruthchett et al. ............... | 514/2 |
| 4,565,819 | 6/1986 | Vincent et al. ............... | 546/146 |
| 5,158,959 | 10/1992 | Geiger et al. ............... | 514/309 |
| 5,162,362 | 11/1992 | Geiger et al. ............... | 514/414 |

FOREIGN PATENT DOCUMENTS

| | | |
|---|---|---|
| 0012380 | 6/1981 | Australia . |
| 0012845 | 7/1980 | European Pat. Off. . |
| 0018549 | 11/1980 | European Pat. Off. . |
| 2448533 | 9/1980 | France . |
| 2448533 | 9/1980 | France . |
| 2470767 | 6/1981 | France . |
| 2042535 | 9/1980 | United Kingdom . |

OTHER PUBLICATIONS

* Burger "Med. Chem.", 3rd Ed. vol. 1, 1970, pp. 1142–1148.
* Geiger et al., "Chemical Abstracts", vol. 97, 1982, col. 97:92759h.
* Remond et al., "Chemical Abstracts", vol. 97, 1982, col. 97:216716p.

Primary Examiner—Werren B. Lone
Attorney, Agent, or Firm—Curtis, Morris & Safford

[57] ABSTRACT

Aminoacid derivatives of the formula I

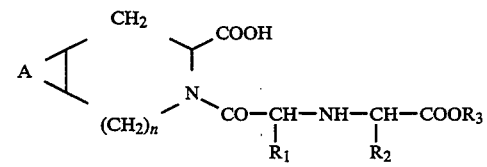

A, n, R$^1$, R$^2$ and R$^3$ have the meanings given, and salts thereof, a process for their preparation, pharmaceutical preparations based on these compounds, and their use as medicaments.

13 Claims, No Drawings

AMINOACID DERIVATIVES, A PROCESS FOR THEIR PREPARATION, AGENTS CONTAINING THESE COMPOUNDS, AND THE USE THEREOF

This application is a continuation of application Ser. No. 06/297,191, filed Aug. 28, 1981, abandoned.

The subject of the invention is a compound of the formula I

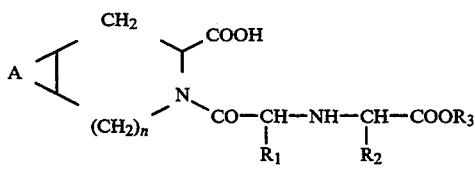

in which n denotes 0 or 1, A⊐ denotes a benzene ring or cyclohexane ring, $R_1$ and $R_2$, which are identical or different and in turn can also be substituted, each represent alkyl or alkenyl having up to 6 C atoms, cycloalkyl or cycloalkenyl, each having 5 to 7 C atoms, cycloalkylalkyl having 7 to 12 C atoms, aryl or partly hydrogenated aryl having 6 to 10 C atoms, aralkyl having 7 to 14 C atoms and a monocyclic or bicyclic heterocyclic structure having 5 to 7 or 8 to 10 members, of which 1 to 2 are —S— or —O— and/or up to 4 are —N atoms, and $R_3$ denotes hydrogen, alkyl having 1 to 6 C atoms, alkenyl having 2 to 6 C atoms or aralkyl having 7 to 14 C atoms, and physiologically tolerated salts thereof.

Methyl, ethyl, n-propyl, isopropyl, n-butyl, isobutyl, tertiary-butyl, the straight-chain and branched pentyls and hexyls, and also cyclopentyl, cyclohexyl, cycloheptyl, cyclopentenyl, cyclohexenyl or cycloheptenyl, phenyl, naphthyl, dihydronaphthyl, tetrahydronapthyl, benzyl, phenethyl, p-fluorophenethyl, o-methylphenethyl, p-methoxyphenethyl, 2,4-dichlorophenethyl and cyclohexylethyl may be particularly mentioned as preferred examples of $R^1$ and $R^2$.

The 5-membered to 7-membered monocyclic or 9-membered and 10-membered bicyclic heterocyclic structures can be unsubstituted, but can also carry one or several identical or different substituents, such as halogen, oxygen (also sulfoxide or sulfone), hydroxyl, carboxyl, carboxamido, sulfonamido, nitro, alkyl and aralkyl having up to 9 C atoms, methoxy or ethoxy. If the ring is substituted, monosubstitution or disubstitution is preferred.

Hydrogen, ethyl, butyl, t-butyl, benzyl and p-nitrobenzyl may be mentioned as preferred meanings for $R^3$.

The alkyls or alkenyls which are suitable as $R^1$ or $R^2$ can be straight-chain or branched. They can carry one or several identical or different substituents, in particular: cycloalkyl or cycloalkenyl having 5–7 C atoms, hydroxyl, alkoxy having 1 to 2 C atoms, aryloxy having 1 to 2 C atoms in the alkyl part, it being possible for the alkyl part to be substituted by methoxy, ethoxy, carboxyl, carboxamido, amino or alkylamino and the aryl part by the substituents mentioned and additionally by helogen or nitro, amino, monoalkylamino, dialkylamino, trialkylamino, monocycloalkylamino, dicycloalkylamino or tricycloalkylamino which has up to a total of 7 C atoms in the alkyl groups or cycloalkyl groups and which can be optionally substituted in the alkyl radical by hydroxyl, carboxyl, carboxamido, carboethoxy, amino, alkylamino, dialkylamino, piperidino or morpholino, alkyloxycarboylamino, aryloxycarbonylamino, aralkyloxycarbonylamino, alkylureido, arylureido, aralkylureido or formyl, or alkanoylamino, aroylamino or aralkanoylamino having up to 10 C atoms, arylamino or aralkylamino in which the aryl part can be monosubstituted or disubstituted by alkyl or alkoxy having 1 to 2 C atoms, methlenedioxy, amino, hydroxyl, acetoxy, carboxyl, carboxamido, carboethoxy, halogen or nitro, alkylmercapto, arylmercapto or aralkylmercapto having up to 7 C atoms, it being possible for the alkyl part to be substituted by methoxy, ethoxy, hydroxyl, carboxyl, carboxamido, carboethoxy, amino or alkylamino and the aryl part by the radicals mentioned and additionally by halogen, nitro or sulfonamido, and also the sulfoxides and sulfones thereof, carboxyl, carboethoxy, carboxamido, alkylaminocarbonyl, cycloalkylaminocarbonyl, cycloalkyleneaminocarbonyl or dialkylaminocarbonyl having up to 6 C atoms, arylaminocarbonyl or aralkylaminocarbonyl, guanido, phenyl, naphthyl, dihydronaphthyl and tetrahydronaphthyl, which can be monosubstituted or disubstituted by halogen, hydroxyl, acetoxy, carboxyl, carboamido, sulfonamido, nitro, methyl, ethyl, methoxy or ethoxy, and 5-membered to 7-membered monocyclic or 9-membered to 10-membered bicyclic heterocyclic structures, which optionally contain 1 to 2 S or O atoms and/or up to 4 N atoms per ring and which can be optionally substituted as described above.

If nothing is mentioned to the contrary in the individual case, alkyl is to be understood, preferably, as meaning a straight-chain or branched alkyl having 1 to 6 C atoms. The same applies for alkanoyl, alkylamino and alkylmercapto.

Aryl preferably denotes phenyl, phenyl which is substituted by halogen, alkyl or alkoxy, or naphthyl. The same applies for aroyl, arylamino and arylmercapto.

Aralkyl preferably includes benzyl, phenethyl and the corresponding compounds substituted in the phenyl nucleus by halogen, nitro, alkyl or alkoxy. The same applies for aralkanoyl, aralkylamino and aralkylmercapto.

Compounds of the general formula I, in which $R_1$ represents the side-chain or a naturally occurring L-aminoacid, for example methyl, isobutyl, methylthioethyl, carboxymethyl, carboxyethyl, amino-n-butyl, guanido-n-propyl, imidazol-4-ethyl, benzyl, 4-hydroxybenzyl or 3-indolemethyl, and functional derivatives thereof, such as ethers, esters or amides, are particularly preferred. The radical $R_1$, however, can also be a part of mercapto acids, hydroxy acids or aminoacids which do not occur in nature.

The invention further relates to a process for the preparation of the compounds of the formula I, which comprises (a) reacting a compound of the formula II with a compound of the formula III

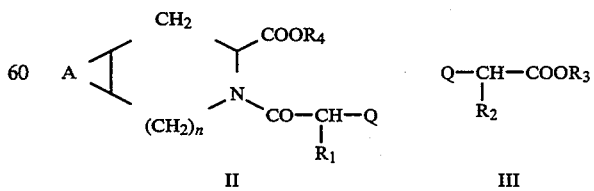

in which one Q denotes a nucleofugic group and the other Q denotes —$NH_2$, and $R_4$ represents H, methyl, ethyl, benzyl or tertiary-butyl, and, if appropriate, converting an ester which is obtained into the carboxylic acid (R$_3$ and/or R$_4$ is hydrogen), or (b) reacting a compound of the formula IV

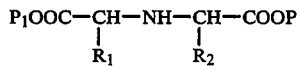

wherein P denotes H, but one of the two P s can also have the meaning of R$_3$ or tertiary-butyl, with a compound of the formula V

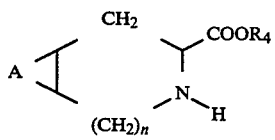

in the presence of a condensing agent, and, if appropriate, converting one or both ester groups into the carboxylic acid, or (c) reacting a compound of the formula VI with a compound of the formula VII

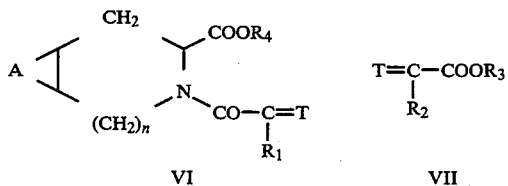

in which one T represents a hydrogen atom and an NH$_2$ group and the other T represents an oxygen atom, and reducing the Schiff base obtained.

For the preparation of the compounds I, 2-halogenocarboxylic acid derivatives II or III can be used, for example, as starting compounds, these derivatives reacting with nucleophiles. This reaction is preferably carried out in water-miscible organic solvents, if appropriate in the presence of water, an inorganic or tertiary or quaternary organic base being added. Aprotic organic solvents are preferred if the reactants are soluble in them, a trialkylamine, tetraalkylammonium hydroxide or tetramethylguanidine or a suspension of an alkali metal carbonatae or alkaline earth metal carbonate being advantageously added as the base.

The starting materials

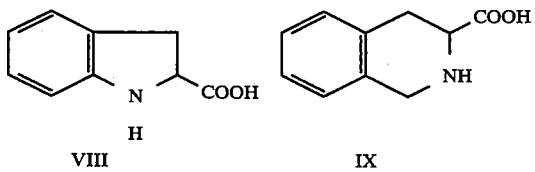

are known from the literature, but their specific pharmacological action as constituents of the compounds of the formula I according to the invention has not hitherto been described. The compound VIII can be prepared according to Aust. J. Chem. 20 (1967), page 1935, and the compound IX according to J. Amer. Chem. Soc. 70 (1948), page 182.

The starting materials

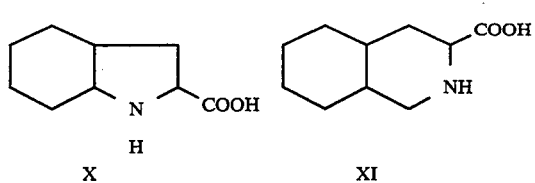

are prepared by catalytic hydrogenation, preferably over rhodium catalysts, from the compounds of the formula VIII or IX.

From these compounds, the ester with R$_4$ is obtained in a known manner, and is condensed with halogenocarboxylic acids to give the compounds II (Q=halogen), either via the acid chlorides, mixed anhydrides or active esters, or by other methods, such as those described in detail in Houben-Weyl, Methoden der Organischen Chemie (Methods of Organic Chemistry), Volume 15. When R$_1$ is CH$_3$, D-2-chloropropionic acid, which is easily obtainable from L-lactic acid, can be used, for example, as the starting material.

The intermediates of the formula II (Q=NH$_2$) are obtained from the carboxylic acid esters of the general formula V by condensation with an N-protected 2-aminocarboxylic acid. The protective group is split off again after the end of the condensation. Benzyloxycarbonyl is an example of a suitable protective group. The condensation can be carried out not only with CDD/HOBt (dicyclohexylcarbodiimide/1-hydroxybenzotriazole), but also with another suitable condensing agent, for example with that described in Houben-Weyl, Volume 15.

Compounds of the formula IV are used as starting materials in procedure (b).

If R$_1$ and R$_2$ are identical, P can be hydrogen. This compound is then condensed, for example in the presence of dicyclohexylcarbodiimide, with one equivalent of a compound of the formula V, and R$_4$ is split off in a known manner. The reaction proceeds possibly via the anhydride XII which can be isolated, the anhydride then being opened with a compound of the formula V.

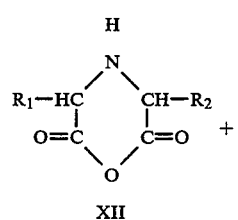

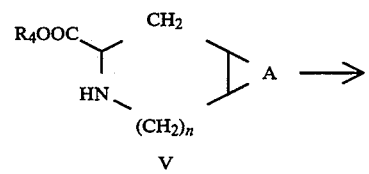

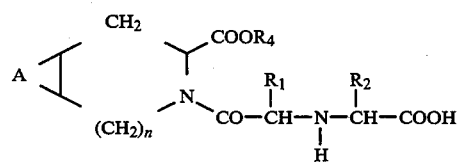

If the radicals $R_1$ and $R_2$ in the compound IV are not identical, preferably only one of the radicals P is hydrogen, and the other should preferably have the meaning of $R^3$ or be tertiary-butyl. This compound is then condensed in the manner described with the compounds of the formula V, and one or both ester groups are converted, if appropriate, to the carboxylic acid.

The condensation which is significant for $T=NH_2$ in the formulae VI or VII and which takes place with 2-ketocarbonic acids or esters thereof according to (c) leads, in a manner which is in itself known, via Schiff bases, for example after reduction with sodium borohydride or sodium cyanoborohydride, by catalytic hydrogenation or electrolytic reduction, to the corresponding compounds of the formula I, in good purity.

The new compounds have, inter alia, 3 chiral centers at α-C atoms. The arrangement of the ligands preferably corresponds to the L-configuration. In general, sterically largely uniform compounds of the formula I can be obtained by crystallization. Counter-current distribution or preparative HPLC are preferable methods for concentrating sterically uniform forms.

Diastereomers can be separated, if appropriate, by crystallization or preparative HPLC at the stage of the intermediates X and XI, so that products of the formula I which have a uniform steric arrangement at all chiral centers can be obtained by the process described above.

The new compounds of the formula I have a lasting, intense hypotensive action.

They can be employed for combating hypertension of various geneses, and can be applied by themselves or in combination with other hypotensive, vasodilatory or diuretic compounds. Typical representatives of these classes of action are described, for example, in Erhart-Ruschig, Arzneimittel (Medicaments), 2nd edition, Weinheim 1972. The compounds can be used intravenously, subcutaneously or perorally.

For the purpose of oral administration, the active compounds are mixed with the usual additives, such as carriers, stabilizers or inert diluents and brought into an appropriate form of administration by usual methods, for example into tablets, gelatin capsules, aqueous alcoholic or oily suspensions or aqueous alcoholic or oily solutions. Suitable inert carriers are, for example, magnesium carbonate, lactose or corn starch. Formulation may be done in the form of dry or humid granules. Suitable oily carriers or solvents are, for example, oils of vegetable or animal origin, such as sunflower oil or cod-liver oil.

For the purpose of subcutaneous or intravenous administration, the active compounds or physiologically acceptable salts thereof are dissolved together with the usual substances. Suitable solvents for the new active compounds and the corresponding physiologically acceptable salts are, for example, water, physiological saline solutions or alcohols, for example ethanol, propanediol or glycerol, or sugar solutions, such as glucose or mannitol solutions, or a mixture of said solvents.

The new compounds may be administered alone or in admixture with physiologically acceptable auxiliaries or carriers.

Suitable physiologically acceptable salts are salts formed with the following acids: hydrochloric or hydrobromic acid, phosphoric acid, sulfuric acid, methylsulfuric acid, amidosulfonic acid, nitric acid, formic acid, acetic acid, propionic acid, succinic acid, tartaric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-amino-salicyclic acid, hydroxyethanesulfonic acid, benzenesulfonic acid, or with synthetic resins containing acid groups.

The dosage in peroral administration is 20–200 mg per individual dose. It can also be increased in severe cases, since toxic properties have not hitherto been observed. A reduction of the dose is also possible, and is especially appropriate if diuretics are administered simultaneously. The individual dose should be between 0.01 and 10 mg in the case of intravenous or subcutaneous administration.

The compounds of the formula I are present as inner salts. If both carboxyl groups are free, alkali metal salts, alkaline earth metal salts and salts with physiologically acceptable amines can additionally be formed. A free amino group which is present can also be reacted with a mineral acid or organic acid to give a salt. The other compounds of the formula I can also be used in the free form or as such salts.

The examples which follow are intended to illustrate the procedure according to the invention, without restricting the invention to the substances mentioned here as representatives.

| | |
|---|---|
| 1,2,3,4-Tetrahydroisoquinoline-3-carboxylic acid | Tic |
| Decahydroisoquinoline-3-carboxylic acid | Dic |
| Indoline-2-carboxylic acid | Idc |
| Octahydroindole-2-carboxylic acid | Oic |
| Benzyloxycarbonyl | Z |
| tertiary-Butyloxycarbonyl | Boc |
| tertiary-Butyl | tBu, $Bu^t$, tert-$C_4H_9$ |
| 4-Nitrobenzyl | Nb |
| Dicyclohexylcarbodiimide | DCC |
| Dimethylformamide | DMF |
| Dimethylacetamide | DMA |
| N-Ethylmorpholine | NEM |
| Cyclohexylamine | CA |
| Dicyclohexylamine | DCA |

If no other process is indicated, the compounds described in the examples which follow are subjected to an HPLC purification for the purposes of analysis and biological determination.

EXAMPLE 1

N-(1-Carboxy-3-phenylpropyl)-L-alanyl-1,2,3,4-tetrahydroisoquinoline-3-carboxylic acid a)
2-Carbobenzoxy-3-carboxy-1,2,3,4-tetrahydroisoquinoline (Z-Tic)

188 g (1.05 moles) of 3-carboxy-1,2,3,4-tetrahydroisoquinoline are added to 1,050 ml of 1N NaOH at 0°, and 160 ml of benzyl chlorocarbonate and a further 1,050 ml of 1N NaOH are then simultaneously added dropwise at this temperature, whilst stirring. The mixture is then stirred for 2 hours at room temperature and extracted three times with ether, and the alkaline/aqueous phase is acidified to pH 1 with concentrated HCl. The oil which separates out is extracted with ethyl acetate. The ethyl acetate solution is washed with water until the water phase has a pH of 3.0. After the ethyl acetate solution has been dried over sodium sulfate, the product crystallizes from this solution after concentration and trituration. 1.5 liters of diisopropyl ether are added to the suspension of crystals, and the latter is stirred for one hour at room temperature, and filtered under suction. The product is dried over phosphorus pentoxide in a high vacuum. Yield: 256.7 g Melting point 138°–39° C.

b) 2-Carbobenzoxy-3-carboxy-1,2,3,4-tetrahydroisoquinoline tertiary-butyl ester 312 ml of tertiary butanol and 8 g of 4-dimethylaminopyridine are added to a solution of 248.8 g (0.8 mole) of 2-carbobenzoxy-3-carboxy-1,2,3,4-tetrahydroisoquinoline in 1,600 ml of methylene chloride. The mixture is cooled to −5° C., and a solution of 176 g of dicyclohexylcarbodiimide in 350 ml of methylene chloride is then added in portions. The mixture is stirred for 5 hours at 0° C., and is then allowed to stand for 16 hours at room temperature. After dicyclohexylurea has been filtered off under suction, the reaction solution is extracted three times with saturated sodium bicarbonate solution. The reaction solution is dried over magnesium sulfate and concentrated in vacuo at room temperature to an oily consistency. 286 g of the product remain as a yellowish oil (97% of theory). NMR: 7.30 s (5H); 7.20 s (4H); 5.1-4.3 m (3H); 5.0 s (2H); 1.46 s (9H)

c) 3-Carboxy-1,2,3,4-tetrahydroisoquinoline tertiary butyl ester hydrochloride 284 g of 2-carbobenzoxy-3carboxy-1,2,3,4-tetrahydroisoquinoline tertiary-butyl ester (0.775 mole) are dissolved in 3 liters of methanol, 15 g of 10% Pd/barium sulfate catalyst are added to the solution, and the latter is hydrogenated with hydrogen under normal pressure. The pH value of the solution is maintained at pH 4.0 (glass electrodes) by dropwise addition of 1N methanolic HCl. The catalyst is filtered off under suction, and the solution is evaporated to dryness in vacuo at room temperature. The product which crystallizes is triturated with anhydrous ether, filtered under suction and dried over phosphorus pentoxide in vacuo. Yield: 156 g Melting point 180° (decomposition)

The tosylate can be obtained either by the addition of methanolic toluenesulfonic acid instead of methanolic hydrochloric acid during the hydrogenation, or by dissolving the hydrochloride in water, adding the calculated quantity of sodium tosylate and cooling the solution to approximately 4° C., whilst seeding and stirring. The tosylate is thereby precipitated in crystalline form. The crystals are filtered off, washed with water and dried.

Melting point 139°–140° (decomposition)

d) Carbobenzoxy-L-alanyl-3-carboxyl-1,2,3,4-tetrahydroisoquinoline tertiary-butyl ester 27 g (0.15 mole) of 3-carboxy-1,2,3,4-tetrahydroisoquinoline tertiary-butyl ester hydrochloride are suspended in 200 of dimethylformamide, the suspension is cooled to −5° C., whilst stirring and with the exclusion of moisture, and 19 ml (0.15 mole) of N-ethylmorpholine and a solution of 33.4 g of carbobenzoxyalanine, 20 g of N-hydroxybenzotriazole and 33 g of dicyclohexylcarbodiimide in 100 ml of dimethylformamide are added to the suspension. The mixture is stirred for one hour at 0° C., is allowed to stand overnight at +4° C., and is then worked up at room temperature after stirring for one hour. The reaction solution is filtered off under suction from the precipitated dicyclohexylurea and is brought to dryness at room temperature in a high vacuum. The oil which remains is taken up in 1 l of ethyl acetate, and is washed with three times 150 ml of saturated sodium carbonate solution, 5% potassium bisulfate solution and once with water. After the solution has been dried over anhydrous sodium sulfate, the solvent is distilled off in vacuo at room temperature. Yield: 59 g of oil.

e) L-Alanyl-3-carboxy-1,2,3,4-tetrahydroisoquinoline tertiary-butyl ester hydrochloride (Ala-Tic-O-But)

15 g of carbobenzoxy-alanyl-3-carboxy-1,2,3,4-tetrahydroisoquinoline tertiary butyl ester in 400 ml of methanol are hydrogenated using 8 g of 10% Pd/barium sulfate catalyst. The apparent pH of the solution (glass electrodes) is kept at 4.0 by the addition of 1N methanolic hydrochloric acid. After 8 hours, the solution is filtered off from the catalyst and is evaporated to dryness in vacuo at room temperature. The solid residue is digested with diisopropyl ether and dried in vacuo.

Melting point 110° (decomposition)

The following compounds are prepared analogously to Ala-Tic-OBut:

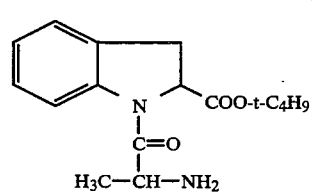

7.3–6.5m(4H); 4.4t(1H);
3.8–3.0m+d(3H); 1.4s(9H); 1.2d(3H)

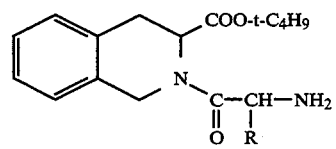

for R:H the following signals are common to the compounds below:
7.2s(4H); 5.1–4.3m(3H);
3.9–3.0m(4H); 1.4s(9H)

7.2s(4H); 3.9–3.0m(5H)

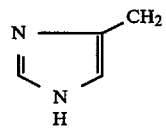

13.1s(1H); 7.5s(1H); 6.8s(1H); 2.8m(2H)

| Structure | NMR |
|---|---|
| (CH₃)₂CH—CH₂— | 1.5m(3H); 0.9d(6H) |
| CH₂F— | 5.1–4.3m(5H) |
| C₆H₅—S—CH₂—CH₂— | 7.2–7.0m(9H); 2.7–2.0m(4H) |
| CH₃—CH₂—CH(CH₃)— | 1.5–1.0m(9H) |
| C₆H₅—CH₂— | 7.1s(5H); 2.7d(2H) |
| 3-indolyl-CH₂— | 7.8–6.4m(9H) |
| HO—CH₂— | 3.7d(2H) |
| C₆H₅—CH₂—O—C(=O)—NH—CH₂—CH₂—CH₂—CH₂— | 7.1s(5H); 5.0s(2H); 2.4m(2H); 1.8–1.3m(6H) |
| C₆H₅—CH₂—O—C(=O)—NH—CH₂—CH₂—CH₂—CH₂—CH₂— | 7.1s(5H); 5.0s(2H); 2.4m(2H); 1.8–1.3m(8H) |
| C₆H₅—CH₂—O—C(=O)—NH—CH₂—CH₂—CH₂— | 7.1s(5H); 5.0s(2H); 2.4m(2H); 1.8–1.3m(4H) |
| C₆H₅—CH₂—O—C(=O)—NH—CH₂— | 7.1s(5H); 5.0s(2H); 2.3m(2H) |
| H₂N—C(=NH)—NCH₂CH₂CH₂— | 8.3–7.6m(2H); 2.9–1.6m(6H) |
| C₆H₅—CH₂—O—C(=O)—NH—CH₂CH₂— | 7.1s(5H); 5.0s(2H); 2.4m(2H); 1.7–1.4m(2H) | f) N-(1-Carboxy-3-phenylpropyl)-B-alanyl-1,2,3,4-tetrahydroisoquinoline-3-carboxylic acid tertiary-butyl ester 305 mg of alanyl-1,2,3,4-tetrahydroisoquinoline-3-carboxylic acid butyl ester (Ala-Tic-OBut) and 445 mg of 4-phenyl-2-oxo-butyric acid are dissolved in 4 ml of methanol, and the solution is brought to a pH of 7.5 with aqueous 1N NaOH. 200 mg of sodium cyanoborohydride are added to the mixture, and the latter is allowed to react for 36 hours. The mixture is concentrated to dryness and the substance is obtained by column chromatography over silica gel (eluant system: chloroform/methanol/water/glacial acetic acid 20+15+2+1). Yield: 382 mg. Melting point decomposition from 120°.

g)
N-(1-Carboxy-3-phenylpropyl)-L-alanyl-1,2,3,4-tetrahydroisoquinoline-3-carboxylic acid 350 mg of N-(1-carboxy-3-phenylpropyl)-Ala-Tic-OBu$^t$ are dissolved in 3 ml of anhydrous trifluoroacetic acid, and the solution is left for 30 minutes at room temperature. The solution is concentrated in vacuo and the residual oil is triturated with cold diisopropyl ether and petroleum ether. Yield: 276 mg of an amorphous substance NMR: 7.20 and 7.10 (s); 4.3 (s, broad); 3.0-3.9 (m, broad); 1.23 and 1.15 (d)

EXAMPLE 2

N-(1-Carboethoxy-3-phenylpropyl)-L-alanyl-1,2,3,4-tetrahydroisoquinoline-3-carboxylic acid 4.8 g of H-Ala-Tic-O Bu$^t$. Tos-OH are dissolved in 40 of absolute ethanol, the solution is adjusted to pH 7 with KOH in ethanol, 6.2 g of ethyl 2-oxo-4-phenylbutyrate are added, and the mixture is stirred in the presence of 9 g of powdered molecular sieve of 4 Å, whilst a solution of 2 g of sodium cyanoborohydride in 15 ml of absolute ethanol is slowly added. After about 20 hours, the mixture is filtered and the solvent is distilled off in vacuo. The residue is distributed between ethyl acetate and water, and the ethyl acetate phase is separated off and brought to dryness in vacuo. The residue is subjected to chromatography over silica gel in an ethyl acetate/cyclohexane (1:2 to 1:4) eluant.

The product is dissolved in 20 ml of trifluoroacetic acid, and the solution is stirred for 30 minutes at room temperature. The trifluoroacetic acid is distilled off in vacuo, and the product is further distilled with toluene and is subjected to chromatography over silica gel in methylene chloride/methanol (10:1). Yield: 2.2 g

EXAMPLE 3

N-(1-Carboxy-5-aminopentyl)-L-alanyl-1,2,3,4-tetrahydroisoquinoline-3-carboxylic acid 10 ml of ice-cold trifluoroacetic acid were poured over 1.2 g of N-(1-carboxy-5-Boc-aminopenthyl)-L-alanyl-1,2,3,4-tetrahydroisoquinoline-3-carboxylic acid, and the mixture was stirred for one hour at room temperature. The mixture is then evaporated in vacuo. The residue is dissolved in water and the solution is subjected to a freeze-drying process. Yield: 0.95 g

EXAMPLE 4

N-(1-Carboxy-3-phenylpropyl)-L-alanyl-1,2,3,4-tetrahydroisoquinoline-3-carboxylic acid 880 mg of N-(1-carboethoxy-3-phenylpropyl)-L-alanyl-1,2,3,4-tetrahydroisoquinoline-3-carboxylic acid are dissolved in 20 ml of dioxane/water (9:1) and are hydrolyzed at room temperature with 4.5 ml of 1N sodium hydroxide solution. After one hour, the solution is acidified with the equivalent quantity of 1N hydrochloric acid, and the dioxane is largely evaporated off. The residue is extracted several times with ethyl acetate, and, after the solvent has been stripped off, the organic phase is subjected to chromatography over a cation exchanger (DOWEX 50). Yield: 630 mg

EXAMPLE 5

N-(1-Carboethoxy-3-aminopropyl)-L-alanyl-1,2,3,4-tetrahydroisoquinoline-3-carboxylic acid 1.1 g of N-(1-carboethoxy-3-benzoxycarbonylaminopropyl)-L-alanyl-1,2,3,4-tetrahydroisoquinoline-3-carboxylic acid are dissolved in 150 ml of methanol and are hydrogenated in the presence of 100 mg of palladium-/active charcoal (10% strength) at 40° C. under normal pressure. After the end of the reaction, the solution is filtered off from the catalyst and the solvent is stripped off in vacuo. Yield: 0.79 g

EXAMPLE 6

N-(1-Carboxy-3-phenyl-3-thiapropyl)-alanyl-1,2,3,4-tetrahydroisoquinoline-3-carboxylic acid a.)
2-(2-Oxo-propionyl)-1,2,3,4-tetrahydroisoquinoline-3-carboxylic acid tertiary-butyl ester A cooled and freshly distilled solution of 270 mg of pyruvic acid in 5 ml of chloroform is rapidly stirred into a solution of 700 mg of Tic-OBut and 630 mg of dicyclohexylcarbodiimide in 15 ml of anhydrous chloroform, the latter solution having been cooled to −50° C. The mixture is left for 16 hours in a deep-freezing cabinet (−20° C.), and the precipitated dicyclohexylurea is filtered off. The solution is washed with KHSO$_4$ solution and then with KHCO$_3$ solution, dried over Na$_2$SO$_4$, and concentrated in vacuo. The compound (oil) contains a little dicyclohexylurea, and was analyzed by chromatography over silica gel in the system CHCl$_3$/CH$_3$OH 15:1.

The following condensation products from Tic, Idc and the corresponding α-ketocarboxylic acid are prepared analogously to the condensation of pyruvic acid with Tic-OBut.

| Structure | NMR signals |
|---|---|
| indoline-N(CO-CO-CH$_3$)-COO-t-C$_4$H$_9$ | 7.3-6.5m(4H); 2.4s(3H); 1.4s(9H) |
| tetrahydroisoquinoline-N(CO-R)-COO-t-C$_4$H$_9$ | the following signals are observed consistently for the basic structure in the compounds below 7.2s(4H); 5.1-4.3m(3H); 3.9-3.0m(2H); 1.4s(9H) |
| —CH$_2$-imidazole | 13.1s(1H); 7.5s(1H); 6.8s(1H); 3.9-3.0m(4H) |
| —CH$_2$—CH(CH$_3$)$_2$ | 2.4-1.0m+d(9H) |
| —CH$_2$—S—C$_6$H$_5$ | 7.2-7.0m(9H); 2.5m(2H) |
| —CH$_2$F | 4.4s(2H) |
| —CH$_2$—C$_6$H$_5$ | 7.15s(5H); 3.0s(2H) |
| —CH$_2$—CH(CH$_3$)—CH$_2$—CH$_3$ | 2.4-1.9m(3H); 1.5-1.0m (8H) |

| | |
|---|---|
| 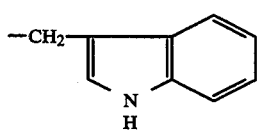 —CH₂— [indole] | 7.8–6.4m(9H); 3.9–2.9m (4H) | b.)
N-(1-Carboxy-3-phenyl-3-thiapropyl)-alanyl-1,2,3,4-tetrahydroisoquinoline-3-carboxylic acid tertiary-butyl ester 1.52 g of pyruvyl-Tic-OBut and 394 mg of S-phenylcysteine are dissolved in 5 ml of methanol, and the solution is adjusted to pH 7.0 with 1N NaOH (aqueous). 400 mg of sodium cyanoborohydride are added to the solution and it is left for 24 hours at room temperature. The mixture is concentrated in vacuo, taken up in chloroform, dried over sodium sulfate and concentrated. The product is obtained in pure form by silica gel chromatography (system CHCl₃/CH₃OH/CH₃COOH/H₂O 50/20/5/1). NMR: 7.3–7.0 m (9H); 5.1–4.3 m (3H); 3.9–3.0 m (4H); 2.5 m (2H)

c.)
N-(1-Carboxy-3-phenyl-3-thiapropyl)-alanyl-1,2,3,4-tetrahydroisoquinoline-3-carboxylic acid 1 g of the butyl ester from example 6b is dissolved in 5 ml of trifluoroacetic acid. After 30 minutes, the solution is concentrated in vacuo, and the residue is digested with diisopropyl ether and dried over potassium hydroxide. Yield: 0.95 g of trifluoroacetate (hygroscopic) NMR: 7.4–7.1 m (9H); 5.2–4.4 m (3H); 3.9–3.0 m (4H); 2.5 m (2H); 1.25 m (3H)

EXAMPLE 7
N-(1-Carboethoxy-2-benzylsulfinylethyl)-L-alanyl-L-1,2,3,4-tetrahydroisoquinoline-3-carboxylic acid 1.3 g of N-(1-carboethoxy-2-benzylthioethyl)-L-alanyl-L-1,2,3,4-tetrahydroisoquinoline-3-carboxylic acid, dissolved in 20 ml of methanol, are added to a mixture of 0.64 g of sodium periodate and 20 ml of water, the mixture being stirred whilst cooled with ice. The reaction mixture is stirred for 24 hours at 0° C., and is then filtered off from the sodium iodate. The filtrate is extracted several times with methylene chloride. 1.1 g of the sulfoxide is obtained after the solvent has been removed. The following signals are observed in the NMR spectrum: 7.3–7.0 m (9H); 5.1–4.3 m (3H); 4.1 s (2H); 3.9–3.0 m (4H); 2.6 m (2H); 1.2 d (3H)

EXAMPLE 8
N-(1-Carboethoxy-3-phenylsulfonyl-propyl)-L-alanyl-1,2,3,4-tetrahydroisoquinoline-3-carboxylic acid 260 mg of N-(1-carboethoxy-3-phenylthio-propyl)-L-alanyl-1,2,3,4-tetrahydroisoquinoline-3-carboxylic acid and 20 mg of sodium tungstate dihydrate are introduced into 50 ml of water, and 1 ml of perhydrol (30% strength) is added dropwise to the mixture. The mixture is warmed to 80° C. for 30 minutes and is then stirred for one hour at room temperature. The excess peroxide is then destroyed with palladium on barium sulfate, and, after the evolution of oxygen has ended, the solution is filtered off from the palladium catalyst and is concentrated. The crude product is purified by ion exchange chromatography over DOWEX 50 H⁺ form. Yield: 220 mg NMR: 7.7 m (9H); 5.1–4.3 m (3H); 3.9–3.0 m (4H); 2.8 m (2H)1 1.5 m (2H); 1.2 d (3H)

EXAMPLE 9
N-(2-Amino-1-carboxypropyl)-L-alanyl-1,2,3,4-tetrahydroisoquinoline-3-carboxylic acid 2.2 g of $N^\beta$-Boc-$\alpha,\beta$-diaminobutyric acid, prepared according to Coll. czech. chem. Commun. 31, 2955 (1966) analogously to the $N^\gamma$-Boc compound, are reacted, in the manner described in Example 6b), with 2.4 g of pyruvyl-Tic-OBut, prepared according to Example 6 a). The Boc protective group is then split off in the manner described in Example 3. Yield: 2.6 g.

EXAMPLE 10
N-(1-Carboxy-3-phenylpropyl)-L-alanyl-decahydroisoquinoline-3-carboxylic acid a. L-Decahydroisoquinoline-3-carboxylic acid (Dic)

250 g of L-1,2,3,4-tetrahydroisoquinoline-3-carboxylic acid are suspended in 2 l of 90 percent acetic acid. 10 g of rhodium on charcoal are added to the suspension, and the latter is hydrogenated for 24 hours at 60° to 80° C. and 120 bar. The filtered solution is concentrated, the residue is taken up in 200 ml of ethyl acetate, and this mixture is added dropwise to 2 l of diisopropyl ether, whilst stirring vigorously. The solution is decanted from the resinous residue and is concentrated in vacuo, and the same procedure is repeated with about ⅓ of the previously used quantity of solvent. The resinous deposits are combined and are treated with hot ethyl acetate, only a part of the solid going into solution. The solution is allowed to run into 3 l of diethyl ether/diisopropyl ether 1:1, whilst stirring vigorously, and a flocculant precipitate is formed, which is filtered off, washed with ether and dried. Yield: 234 g; not uniform by thin layer chromatography (diastereoisomer mixture). Aromatic no longer present according to UV spectrum and NMR. Elementary analysis correct.

The material is employed for the next stage, without further purification.

b. N-Benzyloxycarbonyl-L-decahydroisoquinoline-3-carboxylic acid (Z-Dic-OH)

58 g of L-decahydroisoquinoline-3-carboxylic acid are dissolved in 315 ml of 1N NaOH. 48 ml of benzyloxycarbonyl chloride and 370 ml of 1N NaOH are simultaneously added dropwise to the solution at 0°–5° C. during the course of one hour, whilst stirring vigorously. During this process, a dense precipitate separates out. The mixture is stirred for a further 2 hours after the addition is complete, and is then extracted with ether and the precipitate is filtered off (=sodium salt of a diastereoisomer "A"; yield: 43 g). The filtrate is adjusted to pH 1.5–2 with concentrated HCl, an oil being deposited. It is taken up in ethyl acetate. The aqueous phase is extracted with ethyl acetate, and the combined ethyl acetate solutions are washed with water, dried over sodium sulfate and concentrated to a small volume (approximately 200 ml). A precipitate separates out on addition of 15–18 ml of cyclohexylamine (CA), and this precipitate is filtered off, after cooling the mixture with ice-water, and is washed with a little cold ethyl acetate and then dried. Yield: 48 g (CA salt of the isomer mixture B).

The sodium salt of "A" is converted into the CA salt as follows: the compound is suspended in 500 ml of water, and the suspension is covered with a layer of 200 ml of ethyl acetate and acidified to pH 1.5–2 with concentrated HCl. After the mixture has been extracted by shaking, the ethyl acetate phase is separated off, washed with a little water and dried over sodium sulfate. It is concentrated as described above, and 16 ml of cyclohexylamine are added to it. The CA salt is isolated as described above.

The CA salt of "A" is purified by recrystallization from an eight-fold quantity of ethyl acetate. Melting point: 197°–198° C., $[\alpha]_D = 7.5°$ (c=1, in methanol). Elementary analysis correct.

The CA salt of "B" is recrystallized from a four-fold quantity of ethyl acetate. Melting point: 190° (sinters from 187°) $[\alpha]_D = +14.6°$ (c=1, in methanol). Elementary analysis correct.

The free acids are obtained in a known manner by suspending the CA salts in water/ethyl acetate and acidifying the suspension with citric acid. The ethyl acetate phases are washed with a little water, and concentrated. Z-Dic-OH is obtained as an oily residue.

c. Benzyloxycarbonyl-L-decahydroisoquinoline-3-carboxylic acid tertiary-butyl ester (Z-Dic-OBu$^t$).

41 g of Z-Dic-OH ("A") are dissolved in 350 ml of methylene chloride. 52 ml of t-butanol and 1.3 g of 4-dimethylaminopyridine are added to the solution, the mixture is cooled to 0° C., and a solution of 29 g of dicyclohexylcarbodiimide (DCC) in 60 ml of methylene chloride is added dropwise, whilst stirring. The mixture is then stirred for a further 20 minutes at 0° C. and for 5 hours at room temperature, and the precipititated dicyclohexylurea is filtered off. The filtrate is evaporated in vacuo, the residue is taken up in ethyl acetate, and the solution is washed successively with KHSO$_4$/K$_2$SO$_4$ solution, sodium bicarbonate (unreacted Na salt of Z-Dic-OH is precipitated and is filtered off) and water, and is dried and dried in vacuo. Oily residue. Yield: 38.5 g $[\alpha]_D = -17.3°$ (c=1, in methanol). To obtain the analogous compound of "B", the same procedure is followed. Yield: 38.1 g, $[\alpha]_D = +6.7°$ (c=1, in methanol).

d. L-Decahydroisoquinoline-3-carboxylic acid tertiary-butyl ester tosylate (H-Dic-OBu$^t$.TosOH).

27 g of the compound of "A", prepared according to Example 10c, are catalytically hydrogenated over Pd/charcoal in 250 ml of methanol, with dropwise addition of 4N TosOH in methanol, at pH 4.5 (pH-stat). The filtered solution is then concentrated in vacuo, and the crystalline residue is digested with ether and dried. Yield: 22.6 g. The product is recrystallized from ethyl acetate for the purpose of analysis. Melting point: 159°–160° C.; $[\alpha]_D = -6.5°$ (C=1, in methanol). Elementary analysis correct. The compound is uniform according to thin layer chromatography.

An analogous procedure is followed with the compound of the isomer mixture "B", prepared according to Example 10c. In this process, a substance of melting point 162°–164° C., $[\alpha]_D = +4.4°$ (c=1, in methanol) is obtained after recrystallization from ethyl acetate. Elementary analysis correct.

e. N-Benzyloxycarbonyl-L-alanyl-L-decahydroisoquinoline-3-carboxylic acid tertiary-butyl ester (Z-Ala-Dic-OBu$^t$)

12.4 g of H-Dic-OBu$^t$.TosOH, prepared according to Example 10d using compound "A", are dissolved in 250 ml of methylene chloride. 6.7 g of Z-Ala-OH and 4.05 g of 1-hydroxybenzotriazole (HOBt) are added to the solution, followed by 4.2 ml of N-ethylmorpholine, and a solution of 6.6 g of dicyclohexylcarbodiimide (DCC) in 30 ml of methylene chloride are added dropwise, whilst stirring, at 0° to 4° C. After 5 hours, the mixture is filtered, the filtrate is evaporated to dryness, and the residue is taken up in ethyl acetate. The ethyl acetate solution is washed below 5° C. with 10 percent strength KHSO$_4$/K$_2$SO$_4$ (1:2), 1M sodium bicarbonate and water, and is dried over sodium sulfate and the solvent is distilled off. Resin, readily soluble in all organic solvents. Yield: 15.2 g. An analogous procedure is followed with the isomer mixture "B", which can be separated at this stage by means of preparative HPLC over silica gel in a chloroform/cyclohexane (9:1) eluant.

f. L-Alanyl-L-decahydroisoquinoline-3-carboxylic acid tertiary-butyl ester tosylate (H-Ala-Dic-OBu$^t$.TosOH)

8.5 g of the Z compound are catalytically hydrogenated analogously to Example 10d. The residue, which is at first resinous after the solvent has been distilled off, crystallizes after some time, or on trituration with ethyl acetate, and is recrystallized from ethyl acetate for analysis. Melting point: 151°–153° (decomposition), $[\alpha]_D = -28.8°$ (c=1, in methanol). Elementary analysis correct. An analogous process is followed with the isomer mixture "B". A resin which does not crystallize is obtained; correct elementary analysis.

Alanyl-octahydroindole-2-carboxylic acid t-butyl ester (H-Ala-Oic-OBu$^t$) and the compounds which follow are prepared analogously to H-Ala-Dic-OBu$^t$, and are preferably isolated as the tosylates (NMR data relative to the base):

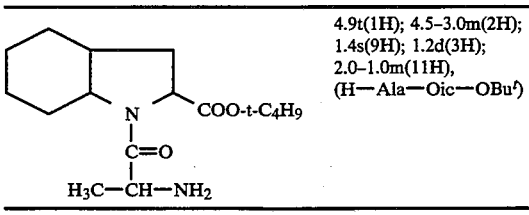

4.9t(1H); 4.5–3.0m(2H); 1.4s(9H); 1.2d(3H); 2.0–1.0m(11H), (H—Ala—Oic—OBu$^t$)

The aminocarboxylic acid starting compound, namely octahydroindole-2-carboxylic acid, is prepared as follows:

45 g of indole-2-carboxylic acid are dissolved in 500 ml of 4 percent sodium hydroxide solution. 20 g of Raney nickel are added to the solution, and hydrogenation is carried out for 24 hours at 40° C. The mixture is filtered, acidified with concentrated HCl and filtered off from undissolved material, and the aqueous phase is extracted several times with butanol. The organic phase is concentrated and subjected to chromatography. (CHCl$_3$/methanol/glacial acetic acid 50:20:5). Yield: 22 g Melting point: 260° C.

The compounds which follow are prepared analogously. The compounds have the following NMR signals:

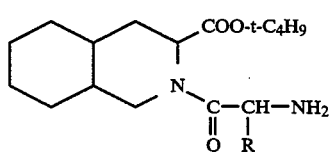  5.1–4.3m(2H); 3.9–3.0m(2H); 1.4s(9H); 2.0–1.0m(12H)
for R:H  3.9–3.0m(4H)
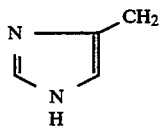  13.1s(1H); 7.5s(1H); 6.8s(1H); 2.8m(2H)
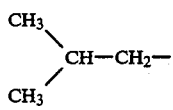  1.0–2.0m(15H); 0.9d(6H)
—CH₂F  5.1–4.3m(4H)
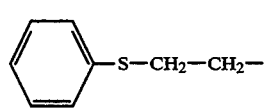  7.2s(5H); 2.7–2.0m(4H)
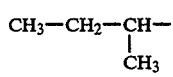  1.0–2.0m(21H)
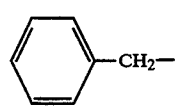  7.1s(5H); 2.7d(2H)
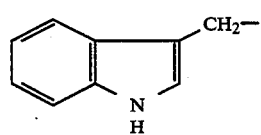  7.8–6.4m(5H); 2.8m(2H)
HO—CH₂—  3.7d(2H)
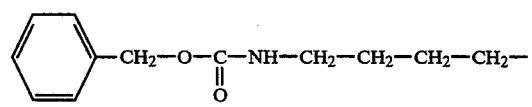  7.1s(5H); 5.0s(2H); 2.4m(2H); 2.0–1.0m(18H)
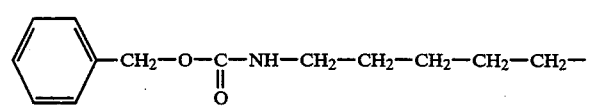  7.1s(5H); 5.0s(2H); 2.4m(2H); 2.0–1.0m(20H)
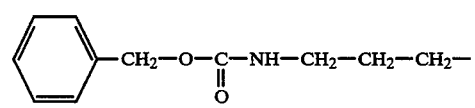  7.1s(5H); 5.0s(2H); 2.4m(2H); 2.0–1.0m(16H)
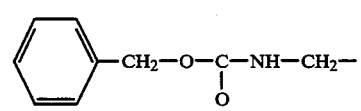  7.1s(5H); 5.0s(2H); 2.3m(2H)
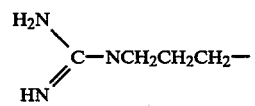  8.3–7.6m(2H); 2.9–1.0m(18H)

| Structure | NMR |
|---|---|
| H₂N–C(=NH)–NH–CH₂– (guanidino-methyl) | 8.3–7.6m(2H); 2.9–2.5m(2H) |
| C₆H₅–CH₂–O–C(=O)–NH–CH₂CH₂– | 7.1s(5H); 5.0s(2H); 2.4m(2H); 2.0–1.0m(14H) |
| 4,6-dimethylpyrimidin-2-yl–NH–CH₂–CH₂–CH₂– | 7.4s(1H); 2.5m(2H); 2.3s(6H); 2.0–1.0m(16H) |
| 4,6-dimethylpyrimidin-2-yl–NH–CH₂– | 7.4s(1H); 2.5m(2H); 2.3s(6H) |
| octahydroindole-2-COO-t-C₄H₉ with N–C(=O)–CH(NH₂)–R | 4.9m(1H); 4.5–3.0m(2H); 1.4s(9H); 2.0–1.0m(11H) |
| for R:H | 3.9–3.0m(4H) |
| imidazol-4-yl–CH₂– | 13.1s(1H); 7.5s(1H); 6.8s(1H); 2.8m(2H) |
| (CH₃)₂CH–CH₂– | 1.0–2.0m(14H); 0.9d(6H) |
| –CH₂F | 5.1–4.3m(4H) |
| C₆H₅–S–CH₂–CH₂– | 7.2–7.0m(5H); 2.7–2.0m(4H) |
| CH₃–CH₂–CH(CH₃)– | 1.0–2.0m(20H) |
| C₆H₅–CH₂– | 7.1s(5H); 2.7d(2H) |
| indol-3-yl–CH₂– | 7.8–6.4m(5H); 2.8m(2H) |
| HO–CH₂– | 3.7d(2H) |

| Structure | NMR |
|---|---|
| Ph-CH₂-O-C(=O)-NH-CH₂-CH₂-CH₂-CH₂- | 7.1s(5H); 5.0s(2H); 2.4m(2H); 2.0-1.0m(17H) |
| Ph-CH₂-O-C(=O)-NH-CH₂-CH₂-CH₂-CH₂-CH₂- | 7.1s(5H); 5.0s(2H); 2.4m(2H); 2.0-1.0m(19H) |
| Ph-CH₂-O-C(=O)-NH-CH₂-CH₂-CH₂- | 7.1s(5H); 5.0s(2H); 2.4m(2H); 2.0-1.0m(15H) |
| Ph-CH₂-O-C(=O)-NH-CH₂- | 7.1s(5H); 5.0s(2H); 2.3m(2H) |
| H₂N-C(=NH)-NH-CH₂CH₂CH₂- | 8.3-7.6m(2H); 2.9-1.0m(17H) |
| H₂N-C(=NH)-NH-CH₂- | 8.3-7.6m(2H); 2.9-2.5m(2H) |
| Ph-CH₂-O-C(=O)-NH-CH₂CH₂- | 7.1s(5H); 5.0s(2H); 2.4m(2H); 2.0-1.0m(13H) |
| 4,6-dimethylpyrimidin-2-yl-NH-CH₂CH₂CH₂- | 7.4s(1H); 2.5m(2H); 2.3s(6H); 2.0-1.0m(15H) |
| 4,6-dimethylpyrimidin-2-yl-NH-CH₂- | 7.4s(1H); 2.5m(2H); 2.3s(6H) | g.
N-(1-Carboxy-3-phenylpropyl)-L-alanyl-L-decahydroisoquinoline-3-carboxylic acid tertiary-butyl ester 305 mg of alanyl-decahydroisoquinoline-3-carboxylic acid t-butyl ester (Ala-Dic-OBut) and 445 mg of 4-phenyl-2-oxo-butyric acid are dissolved in 4 ml of methanol, and the solution is adjusted to pH 7.5 with aqueous 1N NaOH. 200 mg of sodium cyanoborohydride are added to the solution, and the mixture is allowed to react for 36 hours. The mixture is evaporated to dryness, and the substance is obtained by column chromatography over silica gel (eluant system: chloroform/methanol/water/glacial acetic acid 20+15+2+1). Yield: 376 mg. Melting point: decomposition from 123° h.
N-(1-Carboxy-3-phenylpropyl)-L-alanyl-L-decahydroisoquinoline-3-carboxylic acid 350 mg of N-(1-carboxy-3-phenylpropyl)-Ala-Dic-OBut are dissolved in 3 ml of anhydrous trifluoroacetic acid, and the solution is left for 30 minutes at room temperature. The solution is concentrated in vacuo, and the residual oil is triturated with cold diisopropyl ether and petroleum ether. Yield: 226 mg of an amorphous substance. NMR: 7.10 (s); 3.0-3.9 (m, broad); 1.23 and 1.15 (d); 2.0-1.0 (m, broad)

EXAMPLE 11

N-(1-Carboethoxy-3-phenylpropyl)-L-alanyl-L-decahydroisoquinoline-3-carboxylic acid 4.83 g of H-Ala-Dic-OBu$^t$.TosOH are dissolved in 40 ml of absolute ethanol, the solution is adjusted to pH 7 with KOH in ethanol, 6.2 g of ethyl 2-oxo-4-phenylbutyrate are added, and the mixture is stirred in the presence of 9 g of powdered molecular sieve of 4 Å, whilst a solution of 2 g of sodium cyanoborohydride in 15 ml of absolute ethanol is slowly added. After about 20 hours, the mixture is filtered and the solvent is distilled off in vacuo. The residue is distributed between ethyl acetate and water, and the ethyl acetate phase is separated off and dried in vacuo. The residue is subjected to chromatography over silica gel in an ethyl acetate/cyclohexane (1:2 to 1:4) eluant.

The product is dissolved in 20 ml of trifluoroacetic acid for 30 minutes. The trifluoroacetic acid is distilled off in vacuo, and the product is further distilled with toluene and is subjected to chromatography over silica gel in methylene chloride/methanol (10:1). Yield: 1.8 g.

EXAMPLE 12

N-(1-Carboxy-3-phenyl-3-thiapropyl)-alanyl-L-decahydroisoquinoline-3-carboxylic acid a.) 2-(2-Oxopropionyl)-L-decahydroisoquinoline-3-carboxylic acid tert.-butyl ester A cooled freshly distilled solution of 270 mg of pyruvic acid in 5 ml of chloroform is rapidly stirred into a solution of 700 mg of Dic-OBut and 630 mg of dicyclohexylcarbodiimide in 15 ml of anhydrous chloroform, the latter solution being cooled to −50° C. The mixture is left for 16 hours in a deep-freezing cabinet (−20° C.), and the precipitated dicyclohexylurea is filtered off. The solution is washed with KHSO$_4$ solution and then with KHCO$_3$ solution, and is dried over Na$_2$SO$_4$ and concentrated in vacuo. The compound (oil) contains some dicyclohexylurea; it was subjected to chromatography over silica gel in the system CHCl$_3$/CH$_3$OH 15:1 for the purpose of analysis.

The following condensation products are prepared analogously to the condensation of pyruvic acid with Dic-OBut, using the corresponding α-ketocarboxylic acid.

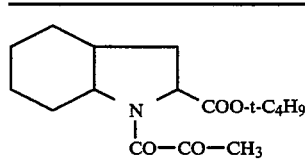

4.9m(1H); 4.2–3.5m(1H); 3.0–1.2m(11H); 2.4s(3H); 1.4s(9H)

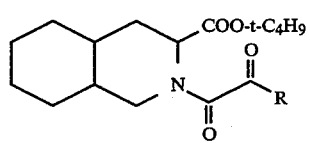

the following signals are consistently observed for the basic structure in the compounds below: 5.1–4.8m(1H); 3.9–3.0m (2H); 1.4s(9H); 2.0–1.0m (12H)

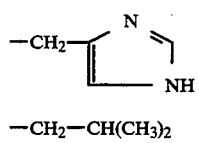

13.1s(1H); 7.5s(1H); 6.8s(1H); 3.9–3.0m(4H)

—CH$_2$—CH(CH$_3$)$_2$     2.4–1.0m(21H)

| | |
|---|---|
| —CH$_2$—S—C$_6$H$_5$ | 7.2–7.0m(5H); 2.5m(2H) |
| —CH$_2$F | 4.4s(2H) |
| —CH$_2$—C$_6$H$_5$ | 7.15(5H); 3.0s(2H) |
| —CH$_2$—CH(CH$_3$)—CH$_2$—CH$_3$ | 2.4–1.0m(23H) |
| —CH$_2$-(indolyl) | 7.8–6.4m(5H); 3.9–2.9m(4H) | b.) N-(1-Carboxy-3-phenyl-3-thiapropyl)-alanyl-L-decahydroisoquinoline-3-carboxylic acid tert.-butyl ester 1.52 g of pyruvyl-Dic-OBut and 394 mg of S-phenylcysteine are dissolved in 5 ml of methanol, and the solution is adjusted to pH 7.0 with 1N NaOH (aqueous). 400 mg of sodium cyanoborohydride are added to the solution, and the mixture is left for 24 hours at room temperature. The mixture is concentrated in vacuo, taken up in chloroform, dried over sodium sulfate, and concentrated. The product is obtained in pure form by silica gel chromatography (system CHCl$_3$/CH$_3$OH/CH$_3$COOH/H$_2$O 50/20/5/1). NMR: 7.3 m (5H); 5.1-4.8 m (1H); 3.9-3.0 m (4H); 2.5 m (2H)

c.) N-(1-Carboxy-3-phenyl-3-phenyl-3-thiapropyl)-alanyl-L-decahydroisoquinoline-3-carboxylic acid 1 g of the butyl ester from Example 12b is dissolved in 5 ml of trifluoroacetic acid. The solution is concentrated in vacuo after 30 minutes, and the residue is digested with diisopropyl ether and dried over potassium hydroxide. Yield: 0.95 g of trifluoroacetate (hygroscopic) NMR: 7.3 m (5H); 5.2-4.8 m (1H); 3.9-3.0 m (4H); 2.5 m (2H); 1.25 m (3H)

EXAMPLE 13

N-(1-Carboxy-3-phenylpropyl)-L-alanyl-L-decahydroisoquinoline-3-carboxylic acid 880 mg of N-(1-carbethoxy-3-phenylpropyl)-L-alanyl-L-decahydroisoquinoline-3-carboxylic acid are dissolved in 20 ml of dioxane/water (9:1), and are hydrolyzed at room temperature with 4.5 ml of 1N sodium hydroxide solution. After one hour, the solution is acidified with the equivalent amount of 1N hydrochloric acid, and the dioxane is largely evaporated off. The residue is extracted several times with ethyl acetate, and, after the solvent has been stripped off, the organic phase is subjected to chromatography over a cation exchanger (DOWEX 50). Yield: 630 mg.

EXAMPLE 14

N-(1-Carboxy-5-aminopentyl)-L-alanyl-L-decahydroisoquinoline-3-carboxylic acid 10 ml of ice-cold trifluoroacetic acid is poured over 1.2 g of N-(1-carboxy-5-Boc-aminopentyl)-L-alanyl-L-decahydroisoquinoline-3-carboxylic acid, and the mixture is stirred for one hour at room temperature. The mixture is then evaporated in vacuo. The residue is dissolved in water and is subjected to a freeze-drying process. Yield: 0.90 g.

EXAMPLE 15

N-(1-Carboethoxy-3-aminopropyl)-L-alanyl-L-decahydroisoquinoline-3-carboxylic acid 1.1 g of N-(1-carboethoxy-3-benzoxycarbonylaminopropyl)-L-alanyl-L-decahydroisoquinoline-3-carboxylic acid are dissolved in 150 ml of methanol, and are hydrogenated in the presence of 100 mg of palladium/active charcoal (10% strength) at 40° C. under normal pressure. After the reaction has ended, the solution is filtered off from the catalyst, and the solvent is stripped off in vacuo. Yield: 0.79 g. NMR: 5.1-4.8 m (1H); 3.9-2.5 m (6H); 2.0-1.0 m (14H); 1.2 d (3H).

EXAMPLE 16

N-(1-Carboethoxy-2-benzylsulfinylethyl)-L-alanyl-L-decahydroisoquinoline-3-carboxylic acid 1.3 g of N-(1-carboethoxy-2-benzylthioethyl)-L-alanyl-L-decahydroisoquinoline-3-carboxylic acid, dissolved in 20 ml of methanol, are added to a mixture of 0.64 g of sodium periodate and 20 ml of water, the mixture being stirred whilst cooled with ice. The reaction mixture is stirred for 24 hours at 0° C., and is then filtered off from the sodium iodate. The filtrate is extracted several times with methylene chloride. After the solvent has been removed, 1.1 g of the sulfoxide is obtained. The following signals are observed in the NMR spectrum: 7.3 m (5.1-4.8 m (1H); 4.1 s (1H); 3.9-3.0 m (4H); 2.6 m (2H); 1.2 d (3H).

EXAMPLE 17

N-(1-Carboethoxy-3-phenylsulfonyl-propyl)-L-alanyl-L-decahydroisoquinoline-3-carboxylic acid 260 mg of N-(1-carboethoxy-3-phenylthio-propyl)-L-alanyl-L-decahydroisoquinoline-3-carboxylic acid and 20 mg of sodium tungstate dihydrate are introduced into 50 ml of water, and 1 ml of perhydrol (30% strength) is added dropwise. The mixture is warmed to 80° C. for 30 minutes, and is then stirred for one hour at room temperature. The excess peroxide is then destroyed with palladium on barium sulfate, and, after the evolution of oxygen has ended, the solution is filtered off from the palladium catalyst and is concentrated. The crude product is purified by ion exchange chromatography over DOWEX 50 H+ form. Yield: 220 mg NMR: 7.7 m (5H); 5.1-4.8 m (1H); 3.9-3.0 m (4H); 2.8 m (2H); 1.5 m (2H); 1.2 d (3H).

EXAMPLE 18

N-(2-Amino-1-carboxypropyl)-L-alanyl-L-decahydroisoquinoline-3-carboxylic acid 2.2 g of N$^\beta$-Boc-$\alpha,\beta$-diaminobutyric acid, prepared analogously to Coll. Czech. chem. Commun. 31, 2955 (1966), are reacted, in the manner described in Example 12b, with 2.4 g of pyruvyl-Dic-OBut, prepared according to Example 12a. The Boc protective group is then split off according to the manner described in Example 14. Yield: 2.6 g. NMR: 5.1-4.8 m (1H); 3.9-3.0 m (5H); 2.0-1.0 m (15H); 1.2 d (3H).

EXAMPLE 19

L-N-(1-Carboethoxy-5-aminopentyl)-L-alanyl-L-decahydroisoquinoline-3-carboxylic acid a) 35 g of N$^\epsilon$-benzyloxycarbonyl-L-lysine ethyl ester hydrochloride and 30.6 g of $\alpha$-bromopropionic acid are dissolved in a mixture of 350 ml of dioxane, 50 ml of ethanol and 75 ml of 4N NaOH. The mixture is stirred overnight at room temperature, keeping the pH constant at 8.8-9 with an autotitrator, and is then adjusted to pH 7-8 with a little HCl, and the solvent is distilled off in vacuo. The residue is dissolved in as little water as possible, and the solution is adjusted to pH 5-6 with hydrochloric acid. The solution is cooled with ice, and the precipitate is filtered off after standing for a short time, washed with a little ice-cold water and ether, and dried in vacuo. The aqueous solution can also be converted into the zwitterion over a weakly basic ion exchanger, and can be purified. The filtrate is then simply lyophilized. Yield: 12.9 g (52%).

b) The compound is dissolved in 100 ml of dimethyl formamide, and 23 g of H-Dic-OBzl. TosOH prepared in the usual manner from the aminoacid by boiling under reflux in benzyl alcohol/toluene/toluenesulfonic acid, and separation of water, 6.5 ml of N-ethylmorpholine, 6.8 g of 1-hydroxybenzotriazole and 11 g of dicyclohexylcarbodiimide are added successively to the solution at room temperature. After 4 hours' stirring, the solution is filtered off from the urea, the solvent is distilled off in vacuo, and the residue is subjected to chromatography over silica gel, in cyclohexane/ethyl acetate (4:1). Separation of the diastereoisomers occurs in this process. The uniform fractions, which contain the title compound, are collected, and the solvent is distilled off in vacuo.

c) The residue is taken up in methanol, catalytically hydrogenated over Pd/charcoal, and, if appropriate, converted into the hydrochloride by adjusting the pH to 3, after the catalyst has been filtered off. The solvent is distilled off and the residue is dried in vacuo.

EXAMPLE 20

L-N-(1-Carboethoxy-3-phenylpropyl)-L-alanyl-L-octahydroindoline-2-carboxylic acid a) 55 g of 2-bromo-4-phenyl-n-butyric acid ethyl ester, 14.5 g of L-alanine-t-butyl ester and 45 ml of triethylamine are kept for 24 hours in tetrahydrofuran. The solvent is distilled off in vacuo, the residue is distributed between water and ethyl acetate, and the ethyl acetate layer is separated off and dried over sodium sulfate, and the solvent is distilled off in vacuo. The residue is subjected to chromatography over silica gel, in cyclohexane/ethyl acetate (4:1), separation of the diastereomers occurring, in addition to the purification. After the appropriate fractions have been concentrated, the t-butyl ester is split off by keeping the compound for 20 minutes in trifluoroacetic acid. The trifluoroacetic acid is distilled off in vacuo, and the product is further distilled in vacuo with toluene.

b) 3.2 ml of N-ethylmorpholine, 3.3 g of 1-hydroxybenzotriazole and 5.5 g of dicyclohexylcarbodiimide are now reacted with 11 g of octahydroindole-2-carboxylic acid benzyl ester tosylate in dimethylformamide, analogously to Example 19b, the reaction mixture is worked up as described in the example, and the diastereomers are separated by chromatography over silica gel in the system cyclohexane/ethyl acetate (4:1). The benzyl ester is split off from the chromatographically uniform compound by means of catalytic hydrogenation.

EXAMPLE 21

L-N-[1-Carboethoxy-4-(4,6-dimethyl-pyrimidyl-2-amino)-butyl]-L-alanyl-L-decahydroisoquinoline-3-carboxylic acid a) 15.3 g of α-bromopropionic acid and 41.1 g of H-Dic-OBut.TosOH are condensed, using 22 g of dicyclohexylcarbodiimide, in 300 ml of tetrahydrofuran in the presence of 12.8 ml of N-ethylmorpholine and 1.35 g of 1-hydroxybenzotriazole. The urea is filtered off after 4 hours, and the solvent is distilled off in vacuo. The residue is taken up in ethyl acetate, the solution is washed with sodium bicarbonate solution and citric acid solution and with water, the ethyl acetate solution is dried over sodium sulfate, and the solvent is distilled off in vacuo.

b) 3.75 g of α-bromopropionyl-Dic-OBut are reacted at room temperature with 2.5 g of $N^\delta$-(4,6-dimethyl-pyrimidin-2-yl-L-ornithin ethyl ester in 20 ml of tetrahydrofuran, with the addition of 1 ml of diisopropylethylamine. The solvent is distilled off in vacuo after 24 hours, the residue is taken up in ethyl acetate, and the solution is washed with water, dried over sodium sulfate and concentrated in vacuo. The residue is subjected to chromatography analogously to Example (20b), with separation of the diastereoisomers. The t-butyl ester is cleaved by dissolving the compound in dioxane/HCl. After 10–15 minutes, the solvent is distilled off, and the residue is dried in vacuo over KOH at a high temperature. The compound is present as the hydrochloride.

EXAMPLE 22

N-(1-S-Carboethoxy-3-phenylpropyl)-S-alanyl-cis-octahydroindole-2-S-carboxylic acid a) N-(1-S-Carboethoxy-3-phenylpropyl)-alanine benzyl ester The free base is obtained from 70 g of alanine benzyl ester toluenesulfonate in an aqueous sodium carbonate solution by extraction with ethyl acetate. 200 ml of dimethylacetamide (DMA) are added to the organic phase which has been dried over anhydrous sodium sulfate, and the mixture is concentrated at room temperature in the vacuum from a water jet. After 90 g of ethyl α-bromophenyl butyrate and 40 ml of N-ethylmorpholine have been added to the solution, it is left for 4 days at room temperature. The reaction is monitored by means of thin layer chromatography on silica gel plates (system: cyclohexane/ethyl acetate 2:1). The mixture is evaporated almost to dryness in vacuo and is adjusted to pH 3 with 2N methanolic hydrochloric acid, and 10 ml of water are added. Excess bromine esters and lipophilic products are extracted in petroleum ether, the methanolic phase is concentrated, 3% sodium carbonate solution (250 ml) is added, and the reaction products are extracted in an ethyl acetate/ether mixture (1:1). After drying over solid sodium sulfate, the extracts are concentrated, and a purification and separation of the diastereomers is undertaken with the aid of a silica gel chromatography (system: cyclohexane/ethyl acetate 4:1). The S,S compound has a low $R_f$ value and is produced in the predominant quantity (48%). The oily substance is immediately further processed.

b) N-(1-S-Carboethoxy-3-phenylpropyl)-S-alanine 37 g of the benzyl ester are taken up in 250 ml of ethanol, and are hydrogenolytically debenzylated using 1 g of Pd/charcoal (10% Pd) under normal pressure during the course of 2 hours. The catalyst is filtered off, the solution is concentrated almost to dryness in vacuo, and the product is precipitated by the addition of petroleum ether. Yield: 33 g; amorphous; NMR: 1.18 (d, 3H); 1.18 (t, 3H); 1.5-2.1 (m, 2H); 2.4-2.8 (m, 2H); 3.0-3.4 (2 m, each 1H); 4.07 (q, 2H); 4.3-5.5 (b, 2H); 7.17 (s, 5H). DMSO-$d_6$ c) N-(1-S-Carboethoxy-3-phenylpropyl)-S-alanyl-cis-octahydroindole-2-R,S-carboxylic acid benzyl ester 5 g of N-(1-S-carboethoxy-3-phenylpropyl)-S-alanine are dissolved in 20 ml of dimethylformamide. 2.45 g of 1-hydroxybenzotriazole, 5.1 g of cis-octahydroindole-R,S-carboxylic acid benzyl ester hydrochloride, 2.5 ml of N-ethylmorpholine and 4 g of dicyclohexylcarbodiimide are added to the solution, and the mixture is stirred for 3 hours at room temperature. The mixture is diluted with 30 ml of ethyl acetate and is filtered off under suction from the urea. After the solution has been concentrated in vacuo, it is taken up in 100 ml of ether and extracted twice with aqueous bicarbonate solution. The organic phase, which has been dried over sodium sulfate and evaporated to dryness, is subjected to chromatography over silica gel. Elution is carried out using ethyl acetate/petroleum ether 4:3, and 2 fractions are obtained, from which colorless oils are obtained by concentration in vacuo.

| Elementary analysis: | C | H | N | |
|---|---|---|---|---|
| calculated for $C_{31}H_{40}N_2O_5$ | 71.5 | 7.7 | 5.4 | yield |
| Fraction 1 | 71.3 | 7.3 | 5.3 | 3.3 g |
| Fraction 2 | 71.6 | 7.6 | 5.6 | 3.9 g | d) N-(1-S-Carboethoxy-3-phenylpropyl)-S-alanyl-cis-octahydroindole-2-S-carboxylic acid 3 g of the benzyl ester (fraction 2) are dissolved in ethanol and are hydrogenolytically debenzylated using 200 mg of 10% Pd/charcoal, under normal pressure. After the absorption of hydrogen has ended (about 1 hour), the solution is filtered off from the catalyst and is concentrated in vacuo. A little pentane is added to the solution, and it is warmed to about 45° C. and a high vacuum is established. An amorphous, solid foam is formed. Yield: 2.4 g. NMR (CDCl$_3$): 1.20 (d, 3H); 1.23 (t, 3H); via multiplet 1.0-2.9 (11H); 3.0-4.5 (m, 3H); 4.12 (q, 2H); 4.65 (b, 2H); 7.13 (s, 5H).

EXAMPLE 23

N-(1-Carboethoxy-3-phenylpropyl)-alanyl-octahydroindole-2-carboxylic acid benzyl ester a) N-tertiary-Butyloxycarbonyl-alanyl-octahydroindole-2-carboxylic acid benzyl ester (Boc-Ala-Oic-OBzl)

19 g of Boc-Ala-OH are dissolved in 100 ml of dimethylformamide, and 13 ml of N-ethylmorpholine, 13.5 g of HOBt and 29.6 g of octahydroindole-2-carboxylic acid benzyl ester hydrochloride are added to the solution. The mixture is cooled in an ice bath, 21 g of dicyclohexylcarbodiimide are added to it, and it is stirred for 15 hours at room temperature. The precipitated urea is filtered off under suction, and the filtrate is concentrated in vacuo and taken up in ethyl acetate. The solution is extracted 3 times in each case with aqueous $KHSO_4$ solution, $KHCO_3$ solution and saturated NaCl solution and the organic phase is concentrated in vacuo. Yield: 38.5 g. NMR: 1.26 (d, 3H); 1.40 (s, 9H); 1,1-2,4 (m, 12H); 3.2-3.9 (m, 2H); 5.28 (s, 2H); 7.31 (s, 5H).

b) Alanyloctahydroindol-2-carboxylic acid benzyl ester trifluoroacetate 21.5 g of Boc-Ala-Oic-OBzl are dissolved in 50 ml of trifluoroacetic acid. The solution is concentrated in vacuo, and the residue is digested several times with diisopropyl ether and is dried in vacuo. Yield: 21 g. The proton signal for the tertiary-butyl group is completely absent in the NMR spectrum.

C) N-(1-Carboethoxy-3-phenylpropyl)-alanyloctahydroindole-2carboxylic acid benzyl ester 11.1 g of Ala-Oic-OBzl.TFA, 7 g of α-bromophenylbutyric acid ethyl ester and 3.3 ml of N-ethylmorpholine are stirred in 20 ml of dimethylacetamide for 4 days at room temperature. The mixture is concentrated to a large extent in vacuo, the residue is dissolved in methanol, the methanolic solution is adjusted to pH 2 with aqueous 2N HCl, and lipophilic compounds are extracted with petroleum ether. The methanolic phase is concentrated and 5% sodium carbonate solution is added to it, and the reaction product is extracted in ethyl acetate. Chromatography over silica gel (system ethyl acetate/petroleum ethe 5:3) yields the title compound as a colorless oil.

The examples listed below are prepared according to one of the following methods A-H, the designated methods being characterized as follows:

Method A: Reductive amination of a condensation product of Tic or Dic $OtC_4H_9$ ester or benzyl ester, or Oic $OtC_4H_9$ ester or benzyl ester, and an appropriate α-ketocarboxylic acid, prepared according to example (6a or 12a), using an appropriate aminoacid derivative according to example (6b), elimination of the protective groups according to example (6c or 12c or 22d), and, if appropriate, hydrolysis according to example (13).

Method B: Reductive amination of a dipeptide t-butyl ester, prepared according to example (1e or 10e, f), using an appropriate α-ketocarboxylic acid derivative according to example (1f, 10g, 11) and, if appropriate, cleavage of the protective group according to example (10h or 11) and/or, if appropriate, according to example (13).

Method C: Reductive amination according to method A and with an ω-protected bifunctional aminoacid cleavage of a protective group from the aminoacid derivative employed, according to Example 3 or 14.

Method D: Oxidation of the basic sulfur compound to the sulfoxide, according to Example 7 or 16.

Method E: Oxidation of the basic sulfur compound to the sulfone, according to example (8) or (17).

Method F: Condensation of an appropriate N-alylated α-aminoacid (prepared according to Example 19a) with an aminoacid ester (for example Dic-OBu$^t$ or Dic-OBzl or Oic-Obu$^t$ or Oic-OBzl) according to Example 19b or 22c, and cleavage of the protective group according to Example 19c or 22d.

Method G: Reaction of an N-acylated aminoacid ester, which carries a nucleofugic group in the acyl part in the α-position to the amide function (such as, for example, halogen, arylsulfonyl or alylsulfonyl) and which is prepared according to Example 21a, with an appropriate aminoacid or an appropriate aminoacid ester according to Example 21b, and cleavage of the protective groups.

Method H: Reaction of a dipeptid benzyl ester, prepared according to Example 23a or 23b, with an appropriately substituted α-arylsulfonyl or α-alkylsulfonyl or α-halogenocarboxylic acid or carboxylic acid ester, prepared according to Example 23c, and cleavage of the benzyl ester to give compounds of the formula I, according to the manner indicated in Example 22d.

If not otherwise indicated, the following NMR data apply for the compounds below (δ values in ppm; TMS as the standard):

A=benzene ring:
for n=1 7.3s (4H), 5.1-4.3 m (3H) 3.9-3.0 m (4H)
n=0 7.2-6.5 m (4H); 4.9 t (1H) 3.6-3.0 m (4H)
A=cyclohexane ring:
n=1 5.1-4.3 m (2H); 3.9-3.0 m (3H); 2.0-1.0 m (12H)
n=0 4.9 m (1H); 4.5-3.0 m (3H), 2.0-1.0 m (11H)
The following signals also occur for the ethyl ester:
4.2 q 7 Hz (2H)
1.2 t 7 Hz (3H)

| No. | n | R¹ | R² | R³ | Method | NMR |
|---|---|---|---|---|---|---|
| 1 | 1 | CH₃ | H–N–CHO<br>\|<br>CH₂ | C₂H₅ | A | 8.3s(1H); 2.9m(2H); 1.2d(3H) |
| 2 | 1 | CH₃ | H–N–COCH₃<br>\|<br>CH₂ | C₂H₅ | A | 2.9m(2H); 2.1s(3H); 1.2d(3H) |
| 3 | 1 | CH₃ | H–N–CO–CH₂–C₆H₅<br>\|<br>CH₂ | C₂H₅ | A | 3.9–3.0m(6H); 2.9m(2H); 1.2d(3H) |
| 4 | 1 | H | H–N–CO–(2-OH-C₆H₄)<br>\|<br>CH₂ | C₂H₅ | A | 7.2–6.8m(8H); 3.9–3.0m(5H); 2.9m(2H) |
| 5 | 1 | H | H–N–CO–(2-COOH-C₆H₄)<br>\|<br>CH₂ | C₂H₅ | A | 7.9–7.0m(8H); 3.9–3.0m(5H); 2.9m(2H) |
| 6 | 1 | CH₃ | H–N–CO–CH₂–(3-Cl-C₆H₄)<br>\|<br>CH₂ | C₂H₅ | A | 7.65–7.1m(8H); 3.9–3.0m(6H); 2.9m(2H); 1.2d(3H) |
| 7 | 1 | CH₃ | H–N–CO–CH₂–(3-Cl-C₆H₄)<br>\|<br>CH₂ | H | A | 7.65–7.1m(8H); 3.9–3.0m(6H); 2.9m(2H); 1.2d(3H) |

-continued
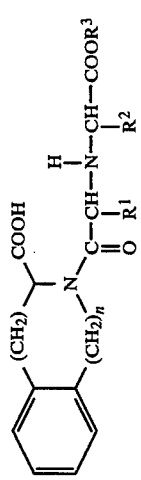
| No. | R¹ | n | R² | R³ | Method | NMR |
|---|---|---|---|---|---|---|
| 8 | CH₃ | 1 | (3-nitrophenyl)-NH-CO-CH₂- | C₂H₅ | A | 8.2–7.1m(8H); 2.9m(2H); 1.2d(3H) |
| 9 | CH₃ | 1 | (3-aminophenyl)-NH-CO-CH₂- | C₂H₅ | A | 7.2–6.8m(8H); 2.9m(2H); 1.2d(3H) |
| 10 | imidazolylmethyl | 1 | (4-methoxyphenyl)-NH-CO-CH₂- | C₂H₅ | A | 13.0s(1H); 7.5–6.8m(10H); 3.9s(3H); 2.9–2.6m(4H) |
| 11 | CH₃ | 1 | (3,4-dimethoxyphenyl)-NH-CO-CH₂- | C₂H₅ | A | 7.5–6.9m(7H); 3.9s(6H); 2.9m(2H); 1.2d(3H) |
| 12 | CH₃ | 1 | (3,4,5-trimethoxyphenyl)-NH-CO-CH₂- | C₂H₅ | A | 7.3–6.8m(6H); 3.9s(9H); 2.9m(2H); 1.2d(3H) |

-continued
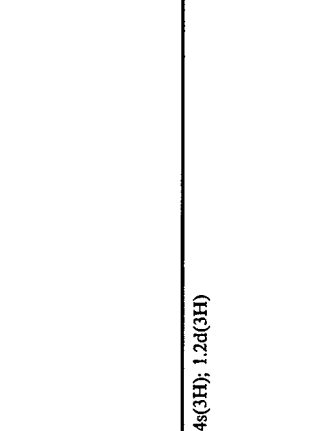
| No. | n | R¹ | R² | R³ | Method | NMR |
|---|---|---|---|---|---|---|
| 13 | 1 | CH₃ | ![o-tolyl-NHCO-CH₂-] (CH₂-NH-CO- attached to 2-methylphenyl) | $C_2H_5$ | A | 7.4–7.0m(8H); 2.9m(2H) 2.4s(3H); 1.2d(3H) |
| 14 | 1 | CH₃ | ![o-tolyl-NHCO-CH₂-] | H | A | 7.4–7.0m(8H); 2.9m(2H); 2.4s(3H); 1.2d(3H) |
| 15 | 1 | CH₃ | CH₂—CH₂—N(CH₃)₂ | $C_2H_5$ | A | 2.4m(2H); 2.2s(6H); 1.7m(2H); 1.2d(3H) |
| 16 | 1 | CH₃ | ![phenyl-NHCO-CH₂-] | $C_2H_5$ | A | 7.3–7.0m(9H); 2.9m(2H); 1.2d(3H) |
| 17 | 1 | CH₃ | ![4-Cl-phenyl-NHCO-CH₂-] | $C_2H_5$ | A | 8.0–7.0m(8H); 2.9m(2H); 1.2d(3H) |
| 18 | 1 | CH₃ | ![3-NO₂-phenyl-NHCO-CH₂-] | $C_2H_5$ | A | 8.3–7.1m(8H); 2.9m(2H); 1.2d(3H) |
| 19 | 1 | (CH₃)₂CH—CH₂ | ![p-tolyl-NHCO-CH₂-] | $C_2H_5$ | A | 7.4–7.0m(8H); 2.9m(2H); 2.3s(3H) 1.0d(6H) |

-continued structure header:
```
        COOH
         |
    (CH2) 
        \
         N—CH—COOH... 
        /      |
  (CH2)n      R²
    |     H
  [phenyl]  N—CH—COOR³
              |
              R²
         C—CH—N—CH—COOR³
         ‖  |   H
         O  R¹
```

| No. | n | R¹ | R² | R³ | Method | NMR |
|---|---|---|---|---|---|---|
| 20 | 1 | CH₃ | H-N-CO-N-(2-OCH₃-C₆H₄) on CH₂ | C₂H₅ | A | 7.3–6.7m(8H); 3.8s(3H); 2.9m(2H); 1.2d(3H) |
| 21 | 1 | CH₃ | H-N-CO-N-(3-Cl-5-CH₃-C₆H₃) on CH₂ | C₂H₅ | A | 7.6–6.9m(7H); 2.9m(2H); 2.4s(3H); 1.2d(3H) |
| 22 | 1 | SCH₂-C₆H₅ | H-N-CO-N-CH₃ on CH₂ | C₂H₅ | A | 7.3–7.0m(9H); 3.0–2.6m+s(7H) |
| 23 | 1 | SCH₂-C₆H₅ | H-N-CO-N-C₄H₉ on CH₂ | H | A | 7.3–7.0m(9H); 3.0–2.6m+s(7H) |
| 24 | 1 | CH₂F | H-N-CO-N-CH₃ on CH₂ | C₂H₅ | A | 5.1–4.3m(5H); 2.9m(2H); 1.0t(3H) |
| 25 | 1 | CH₃ | H-N-C(O)-cyclohexyl on CH₂ | C₂H₅ | A | 3.2–2.9m(3H); 2.4–1.0m(10H); 1.2d(3H) |
| 26 | 1 | CH₃ | H-N-C(O)-O-CH₂-C₆H₅ on CH₂ | C₂H₅ | A | 7.1s(5H); 5.0s(2H); 2.9m(2H); 1.2d(3H) |

-continued

| No. | n | R¹ | R² | R³ | Method | NMR |
|---|---|---|---|---|---|---|
| 27 | 1 | CH₃ | CH₂—N(H)—C(=O)—O—C₂H₅ | C₂H₅ | A | 4.2q(4H); 2.9m(2H); 1.2t+d(9H) |
| 28 | 1 | CH₃ | CH₂—CH₂—N(H)—N—CHO | C₂H₅ | A | 8.2 2s(1H); 2.9m(2H); 1.5m(2H); 1.2d(3H) |
| 29 | 1 | H | CH₂—CH₂—N(H)—N—COOCH₃ | C₂H₅ | A | 3.9–3.0m(5H); 2.9m(2H); 2.1s(3H); 1.5m(2H) |
| 30 | 1 | CH₃ | CH₂—CH₂—N(H)—CO—C₆H₅ | C₂H₅ | A | 7.6–7.0m(9H); 2.9m(2H); 1.5m(2H); 1.2d(3H) |
| 31 | 1 | CH₃ | CH₂—CH₂—N(H)—CO—(2-HO-C₆H₄) | C₂H₅ | A | 7.2–6.8m(8H); 2.9m(2H); 1.5m(2H); 1.2d(3H) |
| 32 | 1 | CH₂-C₆H₅ | CH₂—CH₂—N(H)—CO—(2-COOH-C₆H₄) | C₂H₅ | A | 7.9–7.0m(13H); 2.9–2.7m(4H); 1.5m(2H) |
| 33 | 1 | CH₃ | CH₂—CH₂—N(H)—CO—(4-Cl-C₆H₄) | C₂H₅ | A | 8.0–7.1m(8H); 2.9m(2H); 1.5m(2H); 1.2d(3H) |

-continued

Structure: phenyl ring with two ortho substituents -(CH$_2$)- and -(CH$_2$)$_n$-; the first connects to CH(COOH), the second to N; N is bonded to C(=O)-CH(R$^1$)-NH-CH(R$^2$)-COOR$^3$.

| No. | n | R$^1$ | R$^2$ | R$^3$ | Method | NMR |
|---|---|---|---|---|---|---|
| 34 | 1 | CH$_3$ | -CH$_2$-CH$_2$-NH-C(=O)-(4-Cl-C$_6$H$_4$) | H | A | 8.0–7.1m(8H); 2.9m(2H) 1.5m(2H); 1.2d(3H) |
| 35 | 1 | CH$_3$ | -CH$_2$-CH$_2$-NH-C(=O)-(3-NO$_2$-C$_6$H$_4$) | C$_2$H$_5$ | A | 8.3–7.0m(8H); 2.9m(2H) 1.5m(2H); 1.2d(3H) |
| 36 | 1 | CH$_3$ | -CH$_2$-CH$_2$-NH-C(=O)-(3-NH$_2$-C$_6$H$_4$) | C$_2$H$_5$ | A | 7.2–6.8m(8H); 2.9m(2H); 1.5m(2H); 1.2d(3H) |
| 37 | 1 | CH$_3$ | -CH$_2$-CH$_2$-NH-C(=O)-(4-OCH$_3$-C$_6$H$_4$) | C$_2$H$_5$ | A | 7.5–6.8m(8H); 3.8s(3H); 2.9m(2H); 1.5m(2H); 1.2d(3H) |
| 38 | 1 | CH$_3$ | -CH$_2$-CH$_2$-NH-C(=O)-(3,4-(OCH$_3$)$_2$-C$_6$H$_3$) | C$_2$H$_5$ | A | 7.5–6.9m(7H); 3.9s(6H); 2.9m(2H); 1.5m(2H); 1.2d(3H) |
| 39 | 1 | CH$_3$-CH$_2$-CH(CH$_3$)-CH$_2$ | -CH$_2$-CH$_2$-NH-C(=O)-(3,4,5-(OCH$_3$)$_3$-C$_6$H$_2$) | C$_2$H$_5$ | A | 7.2–6.8m(6H); 3.9s(9H); 2.9m(2H); 1.5–1.0m(13H) |

-continued structure: (CH₂)- phenyl ring with (CH₂)ₙ, COOH, N-C(=O)-CH(R¹)-NH-CH(R²)-COOR³

| No. | n | R¹ | R² | R³ | Method | NMR |
|---|---|---|---|---|---|---|
| 40 | 1 | CH₃ | CH₂-CH₂-N(H)-C(=O)-(2-CH₃-phenyl) | C₂H₅ | A | 7.4–7.0m(8H); 2.9m(2H); 2.3s(3H); 1.5m(2H); 1.2d(3H) |
| 41 | 1 | CH₃ | CH₂-CH₂-N(H)-C(=O)-(2-CH₃-phenyl) | H | A | 7.4–7.0m(8H); 2.9m(2H); 2.3s(3H); 1.5m(2H); 1.2d(3H) |
| 42 | 1 | CH₃ | CH₂-CH₂-CH₂-N(C₂H₅)₂ | C₂H₅ | A | 2.6–2.4m(6H); 1.5m(4H); 1.2d(3H 0.9t(6H) |
| 43 | 1 | CH₃ | CH₂-CH₂-N(H)-CO-N(H)-phenyl | C₂H₅ | A | 7.5–7.0m(9H); 2.9m(2H); 1.5m(2H); 1.2d(3H) |
| 44 | 1 | CH₃ | CH₂-CH₂-N(H)-CO-N(H)-(4-Cl-phenyl) | C₂H₅ | A | 7.5–7.0m(8H); 2.9m(2H); 1.5m(2H 1.2d(3H) |
| 45 | 1 | CH₃ | CH₂-CH₂-N(H)-CO-N(H)-(3-NO₂-phenyl) | C₂H₅ | A | 8.3–7.1m(8H); 2.9m(2H); 1.5m(2H 1.2d(3H) |
| 46 | 1 | CH₃ | CH₂-CH₂-N(H)-CO-N(H)-(2-CH₃-phenyl) | C₂H₅ | A | 7.4–7.0m(8H); 2.9m(2H); 2.3s(3H 1.5m(2H); 1.2d(3H) |

-continued

| No. | n | R¹ | R² | R³ | Method | NMR |
|---|---|---|---|---|---|---|
| 47 | 1 | CH₃ | CH₂—CH₂—N(H)—CO—N(H)—⟨C₆H₄-OCH₃⟩ | C₂H₅ | A | 7.2–6.5m(8H); 3.9s(3H); 2.9m(2H); 1.5m(2H); 1.2d(3H) |
| 48 | 1 | CH₃ | CH₂—CH₂—N(H)—CO—N(H)—⟨C₆H₃(F)(CH₃)⟩ | C₂H₅ | A | 7.3–6.9m(7H); 2.9m(2H); 2.3s(3H); 1.5m(2H); 1.2d(3H) |
| 49 | 1 | (CH₃)₂CH—CH₂ | CH₂—CH₂—N(H)—CO—N(H)—CH₃ | C₂H₅ | A | 3.0–2.6m(5H); 1.7–1.3m(5H); 1.0d(6H) |
| 50 | 1 | (CH₃)₂CH—CH₂ | CH₂—CH₂—N(H)—CO—N(H)—C₄H₉ | C₂H₅ | A | 3.0–2.6m(4H); 1.7–1.2m(9H); 0.9d+t(9H) |
| 51 | 1 | (CH₃)₂CH—CH₂ | CH₂—CH₂—N(H)—CO—N(H)—C₄H₉ | H | A | 3.0–2.6m(4H); 1.7–1.2m(9H); 0.9d+t(9H) |
| 52 | 1 | CH₂F | CH₂—CH₂—N(H)—CO—N(H)—⟨cyclohexyl⟩ | C₂H₅ | A | 5.1–4.3m(5H); 2.9m(3H); 2.0–1.0m(12H) |
| 53 | 1 | CH₃ | CH₂—CH₂—N(H)—CO—O—CH₂—⟨C₆H₅⟩ | C₂H₅ | A | 7.1s(5H); 5.0s(2H); 2.9m(2H); 1.5m(2H); 1.2d(3H) |
| 54 | 1 | CH₃ | CH₂—CH₂—N(H)—CO—O—C₂H₅ | C₂H₅ | A | 4.2q(4H); 2.9m(2H); 1.5m(2H); 1.2d+t(9H) |
| 55 | 1 | CH₃ | CH₂—CH₂—N(H)—CH₃ | C₂H₅ | A | 2.4m(2H); 2.3s(3H); 1.5m(2H); 1.2d(3H) |

-continued
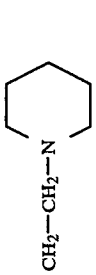
| No. | n | R¹ | R² | R³ | Method | NMR |
|---|---|---|---|---|---|---|
| 56 | 1 | CH₃ | 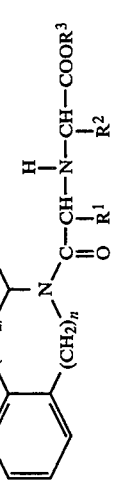 CH₂—CH₂—N | C₂H₅ | A | 2,4m(6H); 1,8–1,2m(8H); 1.2d(3H) |
| 57 | 1 | CH₃ | 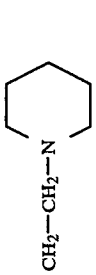 CH₂—CH₂—N(H)—Ph | C₂H₅ | A | 7,2–6,5m(9H); 2,5m(2H); 1,5m(2H); 1.2d(3H) |
| 58 | 1 | (CH₃)₂CH—CH₂ | 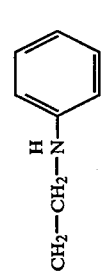 CH₂—CH₂—N(H)—C₆H₄Cl | C₂H₅ | A | 7,2–6,6m(8H); 2,4m(2H); 1,5m(5H); 1.0d(6H) |
| 59 | 1 | 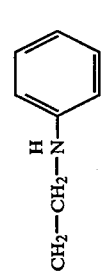 S—CH₂—Ph | 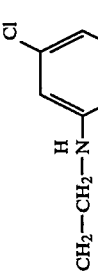 CH₂—CH₂—N(H)—C₆H₄OCH₃ | C₂H₅ | A | 7,3–6,4m(13H); 3.8s(3H); 2.5–2.2m(4H); 1.5m(2H) |
| 60 | 1 | CH₂F | 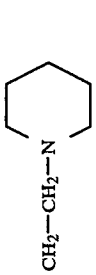 CH₂—CH₂—N(H)—C₆H₃(Cl)(CH₃) | C₂H₅ | A | 7,2–6,6m(7H); 5.1–4.3m(5H); 2.4m(2H); 2.3s(3H); 1.5m(2H) |
| 61 | 1 | CH₃ | 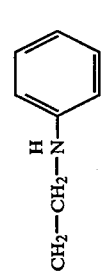 CH₂—N(H)—C₆H₄OCOCH₃ | C₂H₅ | A | 7,3–6,5m(8H); 2,5m(2H); 2.1s(3H); 1.2d(3H) |

-continued $$\begin{array}{c}\text{structure with (CH}_2\text{) groups, COOH, and }-\text{C}(=\text{O})-\text{N(H)}-\text{CH(R}^1\text{)}-\text{C}(=\text{O})-\text{N(H)}-\text{CH(R}^2\text{)}-\text{COOR}^3\end{array}$$

| No. | n | $R^1$ | $R^2$ | $R^3$ | Method | NMR |
|---|---|---|---|---|---|---|
| 62 | 1 | $CH_3$ | 3-$NO_2$-C$_6$H$_4$-NH-CH$_2$- | $C_2H_5$ | A | 7.7–7.0m(8H); 2.5m(2H); 1.2d(3H) |
| 63 | 1 | $CH_3$ | 2-OH,6-CONH$_2$-C$_6$H$_3$-NH-CH$_2$- | $C_2H_5$ | A | 7.6–6.7m(7H); 2.4m(2H); 1.2d(3H) |
| 64 | 1 | $CH_3$ | 4-COOC$_2$H$_5$-C$_6$H$_4$-NH-CH$_2$- | $C_2H_5$ | A | 7.6–6.8m(8H); 4.2q(4H); 2.5m(2H) 1.2d+t(9H) |
| 65 | 1 | $CH_3$ | 3,4-methylenedioxy-C$_6$H$_3$-NH-CH$_2$- | $C_2H_5$ | A | 7.2–6.2m(7H); 5.0s(2H); 2.5m(2H) 1.2d(3H) |
| 66 | 1 | $CH_3$ | 3-NH$_2$-C$_6$H$_4$-NH-CH$_2$- | $C_2H_5$ | A | 7.2–6.7m(8H); 2.5m(2H); 1.2d(3H) |
| 67 | 1 | $CH_3$ | $-CH_2-N(H)-CH_2-CH_2-COOC_2H_5$ | $C_2H_5$ | A | 4.2q(4H); 2.6–2.3m(6H); 1.2d+t(9H) |
| 68 | 1 | $CH_3$ | $CH_2-CH_2-CH_2-NH_2$ | H | C | 2.3m(2H); 1.5m(4H); 1.2d(3H) |
| 69 | 1 | $CH_3$ | $CH_2-N(H)-CH_2-CH_2-N(C_2H_5)_2$ | $C_2H_5$ | A | 2.6–2.4m(10H); 1.2d+t(9H) |

-continued
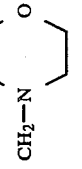
| No. | n | R¹ | R² | R³ | Method | NMR |
|---|---|---|---|---|---|---|
| 70 | 1 | CH₃ | 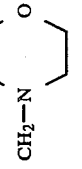 | C₂H₅ | A | 3.9–3.0m(12H); 2.3m(2H); 1.2d(3H) |
| 71 | 1 | CH₃ | 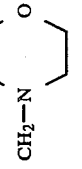 | C₂H₅ | A | 2.6–2.3m(6H); 1.6–1.4m(4H); 1.2d(3H) |
| 72 | 1 | CH₃ | CH₂—N(H)—CH₂—CH₂—CONH₂ | C₂H₅ | A | 2.6–2.2m(6H); 1.2d(3H) |
| 73 | 1 | CH₃ | CH₂—CH₂—CH₂—N(CH₃)₂ | C₂H₅ | A | 2.4m(2H); 2.2s(6H); 1.5m(4H) 1.2d(3H) |
| 74 | 1 | CH₃ | CH₂—N(H)—CH₂—CH₂—CONH₂ | C₂H₅ | A | 3.9–3.0m(6H); 2.4m(2H); 1.2d(3H) |
| 75 | 1 | CH₃ | (CH₂)₅—NH₂ | H | C | 2.3m(2H); 1.6–1.2m(8H); 1.2d(3H) |
| 76 | 1 | H₂N—(CH₂)₄ | (CH₂)₄—NH₂ | H | C | 2.4m(4H); 1.6–1.2m(12H) |
| 77 | 1 | CH₃ | CH₂—CH₂—NH—CH₃ | C₂H₅ | A | 2.4m(2H); 2.2s(3H); 1.5m(2H); 1.2d(3H) |
| 78 | 1 | CH₃ | CH₂—NH—CH₃ | C₂H₅ | A | 2.4m(2H); 2.1s(3H); 1.2d(3H) |
| 79 | 0 | CH₃ | CH₂—N(H)—CO—CH₂—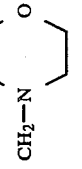 | C₂H₅ | A | 7.2–6.5m(9H); 3.8–3.0m(6H); 2.9m(2H); 1.2d(3H) |
| 80 | 0 | CH₃ | CH₂—N(H)—CO—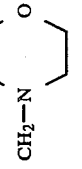 | C₂H₅ | A | 7.8–6.5m(9H); 2.9m(2H); 1.2d(3H) |

-continued
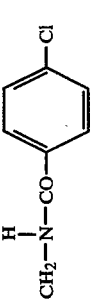
| No. | n | R¹ | R² | R³ | Method | NMR |
|---|---|---|---|---|---|---|
| 81 | 0 | CH₃ | 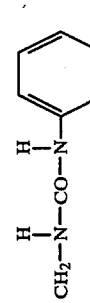 | C₂H₅ | A | 7.8-6.5m(8H); 2.9m(2H); 1.2d(3H) |
| 82 | 0 | CH₃ | 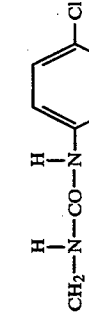 | C₂H₅ | A | 7.4-6.5m(9H); 2.9m(2H); 1.2d(3H) |
| 83 | 0 | CH₃ | 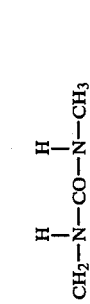 | C₂H₅ | A | 7.7-6.5m(8H); 2.9m(2H); 1.2d(3H) |
| 84 | 0 | CH₃ | 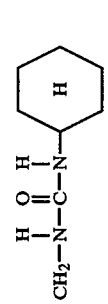 | C₂H₅ | A | 3.0-2.6m+s(5H); 1.2d(3H) |
| 85 | 0 | CH₃ | 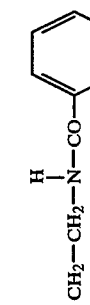 | C₂H₅ | A | 3.2-2.9m(3H); 2.4-1.2m(10H) 1.2d(3H) |
| 86 | 0 | CH₃ |  | C₂H₅ | A | 7.6-6.5m(9H); 2.9m(2H); 1.5m(2H); 1.2d(3H) |
| 87 | 0 | CH₃ | (4-Cl-C₆H₄)NHCONHCH₂CH₂— | C₂H₅ | A | 7.6-6.5m(8H); 2.9m(2H); 1.5m(2H); 1.2d(3H) |

-continued
| No. | n | R¹ | R² | R³ | Method | NMR |
|---|---|---|---|---|---|---|
| 88 | 0 | CH₃ |  | H | A | 7.6–6.5m(8H); 2.9m(2H); 1.5m(2H); 1.2d(3H) |
| 89 | 0 | CH₃ | CH₂—CH₂—CH₂—N(C₂H₅)₂ | C₂H₅ | A | 2.6–2.4m(6H); 1.5m(4H); 1.2d(3H); 1.0t(6H) |
| 90 | 0 | CH₃ |  | C₂H₅ | A | 7.4–6.5m(9H); 2.9m(2H); 1.5m(2H); 1.2d(3H) |
| 91 | 0 | CH₃ |  | C₂H₅ | A | 7.5–6.5m(8H); 2.9m(2H); 1.5m(2H); 1.2d(3H) |
| 92 | 0 | CH₃ |  | C₂H₅ | A | 7.8–6.5m(8H); 2.9m(2H); 1.5m(2H); 1.2d(3H) |
| 93 | 0 | CH₃— |  | C₂H₅ | A | 3.0–2.6m+s(5H); 1.5m(2H); 1.2d, (3H) |
| 94 | 0 | CH₃ |  | C₂H₅ | A | 2.6–2.3m(6H); 1.8–1.2m(8H 1.2d(3H) |
| 95 | 0 | CH₃ |  | C₂H₅ | A | 7.2–6.5m(9H); 2.4m(2H); 1.5m(2H); 1.2d(3H) |

-continued

Structure: a compound with (CH$_2$)$_n$ and (CH$_2$) linkers off a benzene ring, connecting to N-CH(COOH)-... and -C(=O)-CH(R$^1$)-NH-CH(R$^2$)-COOR$^3$

| No. | n | R$^1$ | R$^2$ | R$^3$ | Method | NMR |
|---|---|---|---|---|---|---|
| 96 | 0 | CH$_3$ | CH$_2$-CH$_2$-NH-(3-Cl-C$_6$H$_4$) | C$_2$H$_5$ | A | 7.6–6.5m(8H); 2.4m(2H); 1.5m(2H); 1.2d(3H) |
| 97 | 0 | CH$_3$ | CH$_2$-CH$_2$-NH-(4-OCH$_3$-C$_6$H$_4$) | C$_2$H$_5$ | A | 7.2–6.4m(8H); 3.9s(3H); 2.4m(2H); 1.5m(2H); 1.2d(3H) |
| 98 | 0 | CH$_3$ | (CH$_2$)$_5$-NH$_2$ | H | C | 2.4m(2H); 1.8–1.2m(8H); 1.2d(3H) |
| 99 | 0 | CH$_3$ | (CH$_2$)$_4$-NH$_2$ | H | C | 2.4m(2H); 1.8–1.2m(6H); 1.2d(3H) |
| 100 | 1 | CH$_3$ | CH$_2$-S-C$_6$H$_5$ | C$_2$H$_5$ | A | 7.4–7.0m(9H); 2.7m(2H); 1.2d(3H) |
| 101 | 1 | CH$_3$ | CH$_2$-S-(4-F-C$_6$H$_4$) | C$_2$H$_5$ | A | 7.3–6.8m(8H); 2.7m(2H); 1.2d(3H) |
| 102 | 1 | CH$_3$ | CH$_2$-SH | C$_2$H$_5$ | A | 2.4m(2H); 1.2d(3H) |
| 103 | 1 | CH$_3$ | CH$_2$-S-(4-SO$_2$NH$_2$-C$_6$H$_4$) | C$_2$H$_5$ | A | 8.1–7.1m(8H); 6.5bs(2H); 2.7m(2H); 1.3d(3H) |
| 104 | 1 | (CH$_3$)$_2$CH-CH$_2$ | CH$_2$-S-(3-OCH$_3$-C$_6$H$_4$) | C$_2$H$_5$ | A | 7.2–6.7m(8H); 3.8s(3H); 2.7m(2H); 1.6–1.2m(3H); 1.0d(6H) |

-continued

Structure:

$$\text{Ar} - (CH_2)_n - N(H) - C(=O) - CH(R^1) - N(H) - CH(R^2) - COOR^3$$

where Ar is a 2-(CH₂-)phenyl group bearing a CH(COOH) substituent (as shown in the header structure).

| No. | n | R¹ | R² | R³ | Method | NMR |
|-----|---|----|----|----|--------|-----|
| 105 | 1 | CH₂-(imidazol-like: CH=C-NH-CH=N) | 3-(CONH₂)-C₆H₄-S-CH₂- | C₂H₅ | A | 13.0s(1H); 7.8–6.8m(10H); 6.0bs(2H); 2.9–2.6m(4H) |
| 106 | 1 | 3-indolyl-CH₂- | 3-(NO₂)-C₆H₄-S-CH₂- | C₂H₅ | A | 8.2–6.4m(14H); 2.9–2.6m(4H) |
| 107 | 1 | 3-indolyl-CH₂- | 3-(NH₂)-C₆H₄-S-CH₂- | C₂H₅ | A | 7.8–6.4m(14H); 2.9–2.6m(4H) |
| 108 | 1 | (CH₃)₂CH-CH₂- | 2-(CH₃)-C₆H₄-S-CH₂- | C₂H₅ | A | 7.3–7.0m(8H); 2.7m(2H); 2.3s(3H); 1.9–1.4m(3H); 1.0d(6H) |
| 109 | 1 | CH₃ | -CH₂-S-CH₂-C₆H₅ | C₂H₅ | A | 7.3–7.0m(9H); 3.9–3.0m+s(6H); 2.4m(2H); 1.2d(3H) |
| 110 | 1 | C₆H₅-CH₂- | -CH₂-S-CH(CH₃)₂ | C₂H₅ | A | 7.3–6.9m(9H); 2.6–2.3m(5H); 0.9d(6H) |

| No. | n | R¹ | R² | R³ | Method | NMR |
|---|---|---|---|---|---|---|
| 111 | 1 | $CH_3$ | $-CH_2-S-CH_2-CH_2-N(CH_3)_2$ | $C_2H_5$ | A | 2.6-2.2m+s(12H); 1.2d(3H) |
| 112 | 1 | $CH_2F$ | $-CH_2-S-CH_2-CH_2-CONH_2$ | $C_2H_5$ | A | 5.1-4.3m(5H); 2.5-2.2m(6H) |
| 113 | 1 | $CH_3$ | $-CH_2-S-CH_2-CH_2-COOC_2H_5$ | $C_2H_5$ | A | 4.2q(4H); 2.5-2.2m(6H); 1.2d+t(9H) |
| 114 | 1 | $CH_3$ | $-CH_2-S-CH_2-CH_2-OC_2H_5$ | $C_2H_5$ | A | 3.9-3.0q+m(8H); 2.4-2.2m(4H); 1.2d+t(6H) |
| 115 | 1 | $CH_3$ | $-CH_2-CH_2-S-\text{C}_6\text{H}_5$ | $C_2H_5$ | A | 7.3-7.0m(9H); 2.7m(2H); 1.5m(2H); 1.2d(3H) |
| 116 | 1 | $CH_3$ | $-CH_2-CH_2-S-\text{C}_6\text{H}_4\text{-Cl}$ | $C_2H_5$ | A | 7.5-7.0m(8H); 2.7m(2H); 1.5m(2H); 1.2d(3H) |
| 117 | 1 | $CH_3$ | $-CH_2-CH_2-S-\text{C}_6\text{H}_4\text{-COOH}$ | $C_2H_5$ | A | 7.9-6.9m(8H); 2.7m(2H); 1.5m(2H); 1.2d(3H) |
| 118 | 1 | $CH_3$ | $-CH_2-CH_2-S-\text{C}_6\text{H}_4\text{-SO}_2\text{NH}_2$ | $C_2H_5$ | A | 8.0-6.9m(8H); 6.5bs(2H); 2.6m(2H); 1.5m(2H); 1.2d(3H) |
| 119 | 1 | $CH_3$ | $-CH_2-CH_2-S-\text{C}_6\text{H}_4\text{-OCH}_3$ | $C_2H_5$ | A | 7.3-6.4m(8H); 3.8s(3H); 2.7m(2H); 1.5m(2H); 1.2d(3H) |
| 120 | 1 | $CH_3$ | $-CH_2-CH_2-S-\text{C}_6\text{H}_4\text{-CONH}_2$ | $C_2H_5$ | A | 7.8-6.9m(8H); 6.0bs(2H); 2.6m(2H); 1.5m(2H); 1.2d(3H) |

-continued

General structure:

$$\begin{array}{c} (CH_2) \quad COOH \\ | \\ (CH_2)_n \quad | \\ \diagdown N \diagup \\ | \\ C-CH-N-CH-COOR^3 \\ \| \quad | \quad | \quad | \\ O \quad R^1 \quad H \quad R^2 \end{array}$$

with phenyl ring fused to the (CH₂)/(CH₂)ₙ system.

| No. | n | R¹ | R² | R³ | Method | NMR |
|---|---|---|---|---|---|---|
| 121 | 1 | CH₃ | CH₂—CH₂—S—⟨3-NO₂-C₆H₄⟩ | C₂H₅ | A | 8.1–6.9m(8H); 2.7m(2H); 1.5m(2H); 1.2d(3H) |
| 122 | 1 | H₂N—(CH₂)₄ | CH₂—CH₂—S—⟨4-CH₃-C₆H₄⟩ | C₂H₅ | B | 7.3–6.8m(8H); 2.7–2.3m+s(7H); 1.7–1.3m(8H) |
| 123 | 1 | CH₃ | CH₂—CH₂—S—CH₂—C₆H₅ | C₂H₅ | A | 7.4–7.0m(9H); 3.9–3.0m+s(6H); 2.4m(2H); 1.5m(2H); 1.2d(3H) |
| 124 | 1 | CH₃ | CH₂—CH₂—S—CH(CH₃)₂ | C₂H₅ | A | 2.6–2.3m(3H); 1.5m(2H); 1.2d(3H); 1.0d(6H) |
| 125 | 1 | CH₃ | CH₂—CH₂—S—CH₂—CH₂—N(CH₃)₂ (with indol-3-ylmethyl substituent) | C₂H₅ | A | 7.8–6.5m(10H); 2.8–2.3m(14H); 1.5m(2H) |
| 126 | 1 | CH₃ | CH₂—CH₂—S—CH₂—CH₂—CONH₂ | C₂H₅ | A | 6.0bs(2H); 2.5–2.2m(6H); 1.5m(2H); 1.2d(3H) |
| 127 | 1 | CH₃ | CH₂—S(=O)—C₆H₅ | C₂H₅ | D | 7.5–7.0m(9H); 2.6m(2H); 1.2d(3H) |
| 128 | 1 | CH₃ | CH₂—S(=O)—⟨4-F-C₆H₄⟩ | C₂H₅ | D | 7.4–6.9m(8H); 2.6m(2H); 1.2d(3H) |

| No. | n | R¹ | R² | R³ | Method | NMR |
|---|---|---|---|---|---|---|
| 129 | 1 | CH₃ | −CH₂−S(O)−C₆H₅ | C₂H₅ | D | 7.3–7.0m(9H); 4.1s(2H); 2.6m(2H); 1.2d(3H) |
| 130 | 1 | CH₃ | −CH₂−S(O)−CH(CH₃)₂ | C₂H₅ | D | 2.8–2.5m(3H); 1.2d(3H); 1.0d(6H) |
| 131 | 1 | CH₃ | −CH₂−CH₂−S(O)−C₆H₅ | C₂H₅ | D | 7.4–7.0m(9H); 2.6m(2H); 1.5m(2H); 1.2d(3H) |
| 132 | 1 | CH₃ | −CH₂−CH₂−S(O)−C₆H₄−Cl | C₂H₅ | D | 7.5–6.9m(8H); 2.6m(2H); 1.5m(2H); 1.2d(3H) |
| 133 | 1 | CH₃ | −CH₂−CH₂−S(O)−C₆H₄−CH₃ | C₂H₅ | D | 7.6–6.9m(8H); 2.6m(2H); 2.3s(3H); 1.5m(2H); 1.2d(3H) |
| 134 | 1 | CH₃ | −CH₂−CH₂−S(O)−CH₂−C₆H₅ | C₂H₅ | D | 7.3–7.0m(9H); 4.1s(2H); 2.7m(2H); 1.5m(2H); 1.2d(3H) |
| 135 | 1 | CH₃ | −CH₂−CH₂−S(O)−CH(CH₃)₂ | C₂H₅ | D | 2.8–2.5m(3H); 1.5m(2H); 1.2d(3H); 0.9d(6H) |
| 136 | 1 | CH₃ | −CH₂−CH₂−S(O)−CH₂−CH₂−N(CH₃)₂ | C₂H₅ | D | 2.8–2.2m+s(12H); 1.5m(2H); 1.2d(3H) |

-continued
| No. | n | R¹ | R² | R³ | Method | NMR |
|---|---|---|---|---|---|---|
| 137 | 1 | CH₂ |  | C₂H₅ | E | 7.8–7.1m(9H); 2.8m(2H); 1.2d(3H) |
| 138 | 1 | CH₃ |  | C₂H₅ | E | 7.7–6.9m(8H); 2.8m(2H); 1.2d(3H) |
| 139 | 1 | CH₃ | —CH₂—S(=O)₂—CH₂—  | C₂H₅ | E | 7.6–7.0m(9H); 5.0–4.3m(5H); 2.8m(2H); 1.2d(3H) |
| 140 | 1 | CH₃ | —CH₂—S(=O)₂—CH(CH₃)₂ | C₂H₅ | E | 3.0–2.7m(3H); 1.2d+t(9H) |
| 141 | 1 | CH₃ | —CH₂—CH₂—S(=O)₂—  | C₂H₅ | E | 7.7–7.2m(9H); 2.8m(2H); 1.5m(2H); 1.2d(3H) |
| 142 | 1 | CH₃ | —CH₂—CH₂—S(=O)₂—  | C₂H₅ | E | 8.0–7.1m(8H); 2.8m(2H); 1.5m(2H); 1.2d(3H) |
| 143 | 1 | CH₃ | —CH₂—CH₂—S(=O)₂—  | C₂H₅ | E | 7.6–6.9m(8H); 2.8m(2H); 2.3s(3H); 1.5m(2H); 1.2d(3H) |

-continued

Structure: benzene-fused ring with (CH2) and (CH2)n branches, attached to N-C(=O)-CH(R1)-NH-CH(R2)-COOR3, with COOH group.

| No. | n | R¹ | R² | R³ | Method | NMR |
|-----|---|-----|-----|-----|--------|-----|
| 144 | 1 | CH₃ | CH₂—CH₂—S(=O)(=O)—C₆H₅ | C₂H₅ | E | 7.2–6.9m(9H); 4.2s(2H); 2.8m(2H); 1.5m(2H); 1.2d(3H) |
| 145 | 1 | CH₃ | CH₂—CH₂—S(=O)(=O)—CH(CH₃)₂ | C₂H₅ | E | 3.0–2.7m(3H); 1.5m(2H); 1.1d+t(9H) |
| 146 | 1 | CH₃ | CH₂—CH₂—S(=O)(=O)—CH₂—CH₂—N(CH₃)₂ | C₂H₅ | E | 3.0–2.2m+s(12H); 1.5m(2H); 1.2d(3H) |
| 147 | 0 | CH₃ | CH₂—S—C₆H₅ | C₂H₅ | A | 7.4–6.5m(9H); 2.5m(2H); 1.2d(3H) |
| 148 | 0 | CH₃ | CH₂—S—(4-Cl-C₆H₄) | C₂H₅ | A | 7.4–6.4m(8H); 2.5m(2H); 1.2d(3H) |
| 149 | 0 | CH₃ | CH₂—S—(2-CH₃-C₆H₄) | C₂H₅ | A | 7.5–6.5m(8H); 2.5m(2H); 2.3s(3H); 1.2d(3H) |
| 150 | 0 | CH₃ | —CH₂—S—CH₂—C₆H₅ | C₂H₅ | A | 7.3–6.5m(9H); 3.6–3.0m+s(6H); 2.4m(2H); 1.2d(3H) |
| 151 | 0 | CH₃ | —CH₂—S—CH—(CH₃)₂ | C₂H₅ | A | 2.7–2.3m(3H); 1.2d(3H); 0.9d(6H) |

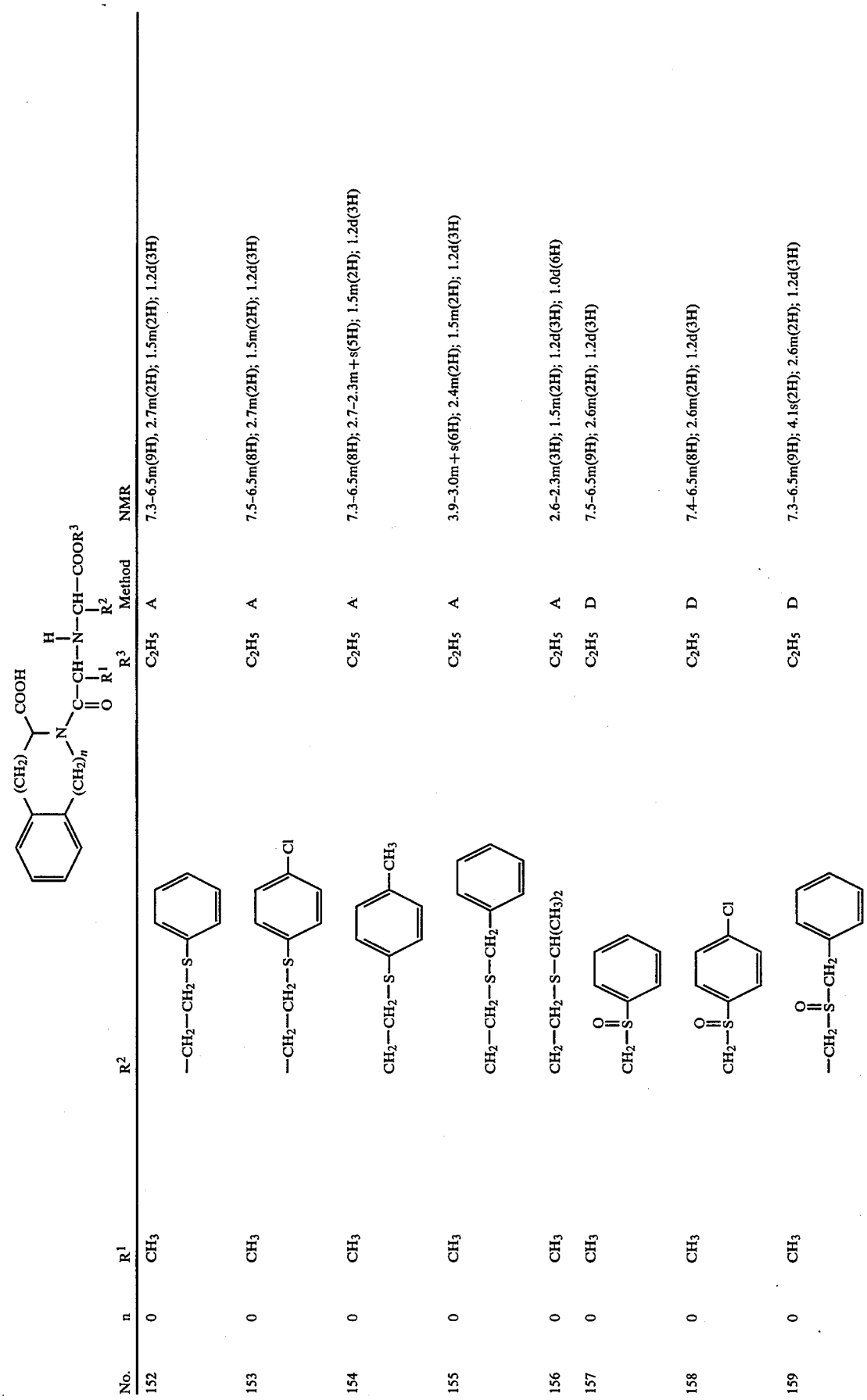

-continued

| No. | n | R[1] | R[2] | R[3] | Method | NMR |
|---|---|---|---|---|---|---|
| 160 | 0 | CH$_3$ | —CH$_2$—S(O)—CH(CH$_3$)$_2$ | C$_2$H$_5$ | D | 2.8–2.5m(3H); 1.2d(3H); 1.0d(6H) |
| 161 | 0 | CH$_3$ | —CH$_2$—S(O)—C$_6$H$_5$ | C$_2$H$_5$ | D | 7.4–6.5m(9H); 2.6m(2H); 1.5m(2H); 1.2d(3H) |
| 162 | 0 | CH$_3$ | —CH$_2$—S(O)—C$_6$H$_4$-Cl | C$_2$H$_5$ | D | 7.5–6.5m(8H); 2.6m(2H); 1.5m(2H); 1.2d(3H) |
| 163 | 0 | CH$_3$ | —CH$_2$—CH$_2$—S(O)—C$_6$H$_4$-CH$_3$ | C$_2$H$_5$ | D | 7.6–6.5m(8H); 2.6m(2H); 2.3s(3H); 1.5m(2H); 1.2d(3H) |
| 164 | 0 | CH$_3$ | —CH$_2$—CH$_2$—S(O)—C$_6$H$_5$ | C$_2$H$_5$ | D | 7.3–6.5m(9H); 4.1s(2H); 2.7m(2H); 1.5m(2H); 1.2d(3H) |
| 165 | 0 | CH$_3$ | —CH$_2$—CH$_2$—S(O)—CH(CH$_3$)$_2$ | C$_2$H$_5$ | D | 2.8–2.5m(3H); 1.5m(2H); 1.2d(3H); 1.1d(6H) |
| 166 | 0 | CH$_3$ | —CH$_2$—SO$_2$—C$_6$H$_5$ | C$_2$H$_5$ | E | 7.8–6.5m(9H); 2.8m(2H); 1.2d(3H) |
| 167 | 0 | CH$_3$ | —CH$_2$—SO$_2$—C$_6$H$_4$-Cl | C$_2$H$_5$ | E | 7.7–6.5m(8H); 2.8m(2H); 1.2d(3H) |

-continued structure header:

![header structure: phenyl ring with (CH2)n and (CH2) substituents bearing N(COOH)CH(R1)-C(=O)-N(H)-CH(R2)-COOR3]

| No. | n | R¹ | R² | R³ | Method | NMR |
|---|---|---|---|---|---|---|
| 168 | 0 | CH₃ | —CH₂—S(O₂)—phenyl | C₂H₅ | E | 7.6–6.5m(9H); 4.3s(2H); 2.8m(2H); 1.2d(3H) |
| 169 | 0 | CH₃ | —CH₂—S(O₂)—CH(CH₃)₂ | C₂H₅ | E | 3.0–2.7m(3H); 1.2d+t(9H) |
| 170 | 0 | CH₃ | —CH₂—CH₂—S(O₂)—phenyl | C₂H₅ | E | 7.7–6.5m(9H); 2.8m(2H); 1.5m(2H); 1.2d(3H) |
| 171 | 0 | CH₃ | —CH₂—CH₂—S(O₂)—(4-Cl-phenyl) | C₂H₅ | E | 8.0–6.5m(8H); 2.8m(2H); 1.5m(2H); 1.2d(3H) |
| 172 | 0 | CH₃ | —CH₂—CH₂—S(O₂)—(4-CH₃-phenyl) | C₂H₅ | E | 7.7–6.5m(8H); 2.8m(2H); 2.3s(3H); 1.5m(2H); 1.2d(3H) |
| 173 | 0 | CH₃ | —CH₂—S(O₂)—CH₂—phenyl | C₂H₅ | E | 7.2–6.5m(9H); 4.2s(2H); 2.8m(2H); 1.5m(2H); 1.2d(3H) |
| 174 | 0 | CH₃ | —CH₂—CH₂—S(O₂)—CH(CH₃)₂ | C₂H₅ | E | 3.0–2.7m(3H); 1.5m(2H); 1.1d+t(9H) |
| 175 | 1 | CH₃ | —CH₂—OH | C₂H₅ | A | 3.9–3.0m(6H); 1.2d(3H) |

-continued

| No. | n | R¹ | R² | R³ | Method | NMR |
|---|---|---|---|---|---|---|
| 176 | 1 | CH₃ | -CH₂-O-C₆H₅ | C₂H₅ | A | 7.3–6.7m(9H); 3.9–3.0m(6H) 1.2d(3H) |
| 177 | 1 | CH₃ | -CH₂-O-C₆H₄-CH₃ (4-) | C₂H₅ | A | 7.3–6.6m(8H); 3.9–3.0m(6H); 2.3s(3H); 1.2d(3H) |
| 178 | 1 | CH₃ | -CH₂-O-C₆H₄-Cl (4-) | C₂H₅ | A | 7.3–6.7m(8H); 3.9–3.0m(6H); 1.2d(3H) |
| 179 | 1 | H₂N—(CH₂)₄ | -CH₂-O-C₆H₄-OCH₃ (3-) | C₂H₅ | B | 7.2–6.4m(8H); 3.9–3.0m+s(9H); 2.4m(2H); 1.7–1.3m(6H) |
| 180 | 1 | H₂N—(CH₂)₃ | -CH₂-O-C₆H₄-NO₂ (4-) | C₂H₅ | B | 8.2–6.8m(8H); 3.9–3.0m(6H); 2.4m(2H); 1.7–1.3m(4H) |
| 181 | 1 | (CH₃)₂—CH—CH₂— | -CH₂-O-C₆H₄-COOC₂H₅ (4-) | C₂H₅ | A | 7.6–6.8m(8H); 4.2q(4H); 3.9–3.0m(6H); 1.9–1.3m(3H); 1.2t(6H) 1.0d(6H) |
| 182 | 1 | CH₃ | -CH₂-O-C₆H₃(CH₃)(Cl) (2-CH₃, 5-Cl) | C₂H₅ | A | 7.2–6.0m(7H); 3.9–3.0m(6H); 2.3s(3H); 1.2d(3H) |

-continued
| No. | n | R¹ | R² | R³ | Method | NMR |
|---|---|---|---|---|---|---|
| 183 | 1 | $CH_3$ | $-CH_2-O-CH_2-$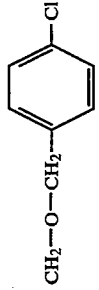 | $C_2H_5$ | A | 7.2-6.9m(9H); 4.0s(2H); 3.9-3.0m(6H); 1.3d(3H) |
| 184 | 1 | $CH_3$ | $CH_2-O-CH_2-$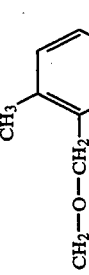(Cl) | $C_2H_5$ | A | 7.4-6.9m(8H); 4.0s(2H); 3.9-3.0m(6H); 1.2d(3H) |
| 185 | 1 | $H_2N-(CH_2)_4$ | $CH_2-O-CH_2-$($CH_3$) | $C_2H_5$ | B | 7.4-7.0m(8H); 4.0s(2H); 3.9-3.0m(6H); 2.5-2.2d+t(5H); 1.7-1.3m(6H) |
| 186 | 1 | (indol-3-ylmethyl) | $CH_2-O-CH_2-$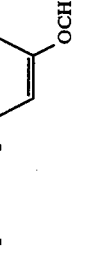($OCH_3$) | $C_2H_5$ | A | 7.8-6.4m(14H); 4.0s(2H); 3.8s(3H) 3.9-3.0m(6H); 2.7m(2H) |
| 187 | 1 | H | $CH_2-O-CH_2-$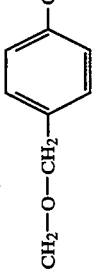($CONH_2$) | $C_2H_5$ | A | 7.8-7.0m(8H); 6.0bs(2H); 4.0s(2H); 3.9-3.0m(7H) |
| 188 | 1 | $HS-CH_2$ | $CH_2-O-CH_2-$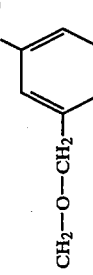($NO_2$) | $C_2H_5$ | B | 8.2-7.0m(8H); 4.0s(2H); 3.9-3.0m(6H); 2.3m(2H) |

-continued
Structure:
| No. | n | R¹ | R² | R³ | Method | NMR |
|-----|---|-----|-----|-----|--------|-----|
| 189 | 1 | HS—CH₂ | ![m-aminophenyl]  (3-NH₂-C₆H₄-) | C₂H₅ | B | 7.2–6.4m(8H); 4.0s(2H); 3.9–3.0m(6H); 2.3m(2H) |
| 190 | 1 | CH₃ | CH₂—O—CH(CH₃)₂ | C₂H₅ | A | 3.9–3.0m(7H); 1.2d(3H); 0.9d(6H) |
| 191 | 1 | CH₃ | CH₂—O—CH₂—CH₂—N(CH₃)₂ | C₂H₅ | A | 3.9–3.0m(8H); 2.4–2.1m+s(8H); 1.2d(3H) |
| 192 | 1 | CH₃ | —CH₂—O—C(=O)—NH—C₆H₅ | C₂H₅ | A | 7.6–6.9m(9H); 4.0m(2H); 1.2d(3H) |
| 193 | 1 | CH₃ | CH₂—COOH | H | A | 2.1m(2H); 1.2d(3H) |
| 194 | 1 | CH₃ | CH₂—CONH₂ | H | F | 6.5bs(2H); 2.1m(2H); 1.2d(3H) |
| 195 | 1 | CH₃ | CH₂—CON(CH₃)₂ | H | F | 3.9–3.0m+2s(10H); 2.1m(2H); 1.2d(3H) |
| 196 | 1 | CH₃ | 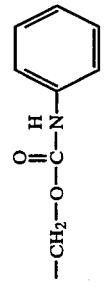 (indol-3-ylmethyl, CH₂-indole) | H | F | 7.8–6.4m(15H); 2.8–2.0m(4H) |
| 197 | 1 | CH₃ | CH₂—CONH—(3-CH₃-C₆H₄) 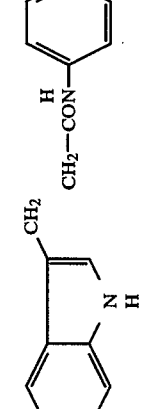 | H | F | 7.3–6.9m(8H); 2.3s(3H); 2.2m(2H); 1.2d(3H) |
| 198 | 1 | CH₃ | CH₂—CONH—(4-Cl-C₆H₄)  | H | F | 7.7–6.9m(8H); 2.3m(2H); 1.2d(3H) |

-continued

Structure:

Main scaffold: phenyl ring with two (CH₂)ₙ substituents — one bearing CH(COOH)— and the other bearing —N(H)—C(=O)—CH(R¹)—N(R²)—CH(R³)—COOR³

| No. | n | R¹ | R² | R³ | Method | NMR |
|---|---|---|---|---|---|---|
| 199 | 1 | ![imidazolyl-CH₂] (imidazol-4-yl-methyl: CH₂ attached to imidazole N=CH-NH) | 4-CH₃O-C₆H₄-NH-CO-CH₂- | H | F | 13.0s(1H); 7.5–6.3m(10H); 3.9s(3H); 2.7m(2H); 2.1m(2H) |
| 200 | 1 | CH₃ | 4-HOOC-C₆H₄-NH-CO-CH₂- | H | F | 7.7–6.6m(8H); 2.1m(2H); 1.2d(3H) |
| 201 | 1 | CH₃ | 4-H₂NOC-C₆H₄-N(H)-CO-CH₂- | H | F | 7.7–6.6m(8H); 2.1m(2H); 1.2d(3H) |
| 202 | 1 | CH₃ | 4-C₂H₅OOC-C₆H₄-N(H)-CO-CH₂- | H | F | 7.7–6.6m(8H); 4.2q(2H); 2.1m(2H); 1.2d+t(6H) |
| 203 | 1 | CH₃ | 4-C₂H₅O-C₆H₄-N(H)-CO-CH₂- | H | F | 7.2–6.2m(8H); 3.5q(2H); 2.1m(2H); 1.2d+t(6H) |
| 204 | 1 | CH₃ | (5-Cl-2-CH₃O-C₆H₃)-N(H)-CO-CH₂- | H | F | 7.2–6.4m(7H); 3.9s(3H); 2.1m(2H); 1.2d(3H) |

-continued

Structure:

[Phenyl ring with -(CH₂)- and -(CH₂)ₙ- substituents connecting to N; N bears -CH(COOH) group and -C(=O)-CH(R¹)-N(H)-CH(R²)-COOR³]

| No. | n | R¹ | R² | R³ | Method | NMR |
|---|---|---|---|---|---|---|
| 205 | 1 | CH₃ | CH₂-CO-NH-C₆H₃(OCH₃)₂(OCH₃) (3,4,-(OCH₃)₂ with NHCO at para; OCH₃ groups at positions shown) | H | F | 7.2–6.4m(7H); 3.8s(6H); 2.1m(2H); 1.2d(3H) |
| 206 | 1 | CH₃ | CH₂-CO-NH-C₆H₂(OCH₃)₃ | H | F | 7.2–6.2m(6H); 3.9s(9H); 2.1m(2H); 1.2d(3H) |
| 207 | 1 | CH₃ | CH₂-COOC₂H₅ | H | F | 4.2q(2H); 2.0m(2H); 1.2d+t(6H) |
| 208 | 1 | CH₃ | CH₂-CO-O-CH(CH₃)₂ | H | F | 4.8septett(1H); 2.1m(2H); 1.2d(3H); 0.9d(6H) |
| 209 | 1 | CH₃ | CH₂-CO-O-CH₂-C₆H₅ | H | F | 7.3–7.0m(9H); 5.3s(2H); 2.1m(2H); 1.2d(3H) |
| 210 | 1 | CH₃ | CH₂-CH₂-COOH | C₂H₅ | A | 2.1m(2H); 1.5m(2H); 1.2d(3H) |
| 211 | 1 | CH₃ | CH₂-CH₂-CONH₂ | C₂H₅ | A | 2.1m(2H); 1.5m(2H); 1.2d(3H) |
| 212 | 1 | CH₃ | CH₂-CH₂-CON(CH₃)₂ | C₂H₅ | A | 3.02s(6H); 1.5m(2H); 1.2d(3H) |
| 213 | 1 | CH₃ | CH₂-CH₂-CO-NH-C₆H₅ | C₂H₅ | A | 7.4–7.0m(9H); 2.1m(2H); 1.5m(2H); 1.2d(3H) |
| 214 | 1 | CH₃ | CH₂-CH₂-CO-NH-C₆H₄-F (4-F) | C₂H₅ | A | 7.3–6.9m(8H); 2.1m(2H); 1.5m(2H); 1.2d(3H) |

-continued

| No. | n | R¹ | R² | R³ | Method | NMR |
|---|---|---|---|---|---|---|
| 215 | 1 | H₂N—(CH₂)₄ | CH₂—CH₂—CONH—⟨C₆H₄⟩ (structure with phenyl) | C₂H₅ | B | 7.3–6.8m(8H); 2.4–2.1m(4H); 1.7–1.3m(8H) |
| 216 | 1 | CH₃ | CH₂—CH₂—CONH—⟨4-F-C₆H₄⟩ | C₂H₅ | A | 7.2–6.4m(8H); 3.9s(3H); 2.1m(2H); 1.5m(2H); 1.2d(3H) |
| 217 | 1 | CH₃ | CH₂—CH₂—CONH—⟨4-CH₃-C₆H₄⟩ | H | A | 7.3–6.3m(8H); 2.1m(2H); 1.5m(2H); 1.2d(3H) |
| 218 | 1 | CH₃ | CH₂—CH₂—CONH—⟨3-OH-C₆H₄⟩ | H | A | 7.3–6.4m(7H); 3.9s(3H); 2.1m(2H); 1.5m(2H); 1.2d(2H) |
| 219 | 1 | CH₃ | CH₂—CH₂—CONH—⟨2-OCH₃-5-Cl-C₆H₃⟩ | H | A | 7.7–7.0m(8H); 2.1m(2H); 1.5m(2H); 1.2d(3H) |
| 220 | 1 | CH₃ | CH₂—CH₂—CONH—⟨4-CONH₂-C₆H₄⟩ | H | A | 7.6–7.0m(8H); 4.2q(2H); 2.1m(2H); 1.5m(2H); 1.2d+t(6H) |
| 221 | 1 | CH₃ | CH₂—CH₂—CONH—⟨4-COOC₂H₅-C₆H₄⟩ | H | A | |
| | 1 | CH₃ | CH₂—CH₂—CONH—⟨4-OC₂H₅-C₆H₄⟩ | H | A | 7.3–6.4m(8H); 3.9–3.0m+q(6H); 2.1m(2H); 1.5m(2H); 1.2d+t(6H) |

-continued
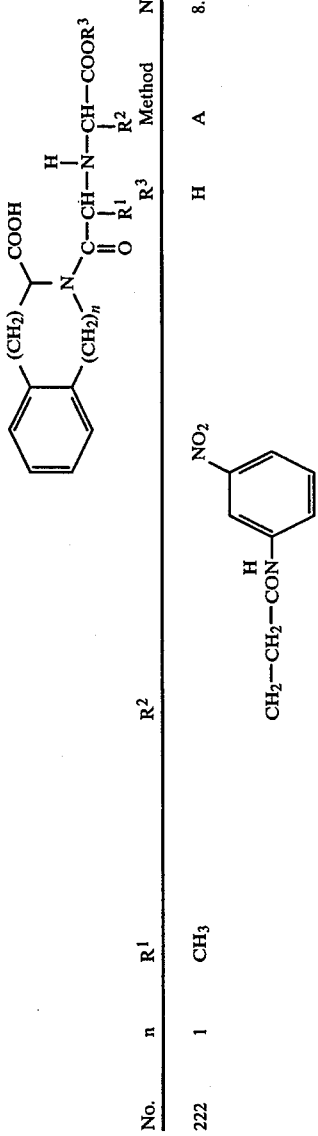
| No. | n | R¹ | R² | R³ | Method | NMR |
|---|---|---|---|---|---|---|
| 222 | 1 | $CH_3$ | 3-$NO_2$-C$_6$H$_4$-$CH_2$-$CH_2$-CONH- | H | A | 8.2–6.9m(8H); 2.1m(2H); 1.5m(2H); 1.2d(3H) |

| No. | n | R¹ | R² | R³ | Method | NMR |
|---|---|---|---|---|---|---|
| 223 | 1 | $CH_3$ | $CH_2-CH_2-CON(H)-$ (3-OCH$_3$, 4-OCH$_3$-phenyl) | $C_2H_5$ | A | 7.3–6.3m(7H); 3.8s(6H); 2.1m(2H); 1.5m(2H); 1.2d(3H) |
| 224 | 1 | $CH_3$ | $CH_2-CH_2-CON(H)-$ (3,4,5-tri-OCH$_3$-phenyl) | $C_2H_5$ | A | 7.3–6.2m(6H); 3.9s(9H); 2.1m(2H); 1.5m(2H); 1.2d(3H) |
| 225 | 1 | $CH_3$ | $CH_2-CH_2-CON(H)-CH(CH_3)_2$ | H | A | 2.8–2.2m(3H); 1.5m(2H); 1.2d(3H); 1.0d(6H) |
| 226 | 1 | $CH_3$ | $CH_2-CH_2-CON(H)-CH_2-$phenyl | H | A | 7.4–7.0m(9H); 5.1–4.3m+s(5H); 2.1m(2H); 1.5m(2H); 1.2d(3H) |
| 227 | 1 | $CH_3$ | $CH_2-CH_2-CON(H)-CH_2-$(3-OCH$_3$, 4-OCH$_3$-phenyl) | $C_2H_5$ | A | 7.3–6.2m(7H); 3.9s(6H); 2.9–2.1m(6H); 1.5m(2H); 1.2d(3H) |
| 228 | 0 | $CH_3$ | $CH_2-OH$ | $C_2H_5$ | A | 3.6–3.0m(6H); 1.2d(3H) |
| 229 | 0 | $CH_3$ | $-CH_2-O-$phenyl | $C_2H_5$ | A | 7.3–6.5m(9H); 3.9–3.0m(6H); 1.2d(3H) |

-continued

| No. | n | R¹ | R² | R³ | Method | NMR |
|---|---|---|---|---|---|---|
| 230 | 0 | CH₃ | —CH₂—O—CH₂—C₆H₅ | C₂H₅ | A | 7.2–6.5m(9H); 4.0s(2H); 3.9–3.0m(6H); 1.2d(3H) |
| 231 | 0 | CH₃ | —CH₂—O—CH₂—C₆H₄Cl (4-Cl) | C₂H₅ | A | 7.4–6.5m(8H); 4.0s(2H); 3.9–3.0m(6H); 1.2d(3H) |
| 232 | 0 | CH₃ | CH₂—O—CH(CH₃)₂ | C₂H₅ | A | 3.9–3.0m(7H); 1.2s(3H); 0.9d(6H) |
| 233 | 0 | CH₃ | CH₂—O—CH₂—CH₂—N(CH₃)₂ | C₂H₅ | A | 3.9–3.0m(8H); 2.4–2.1m+s(8H); 1.2d(3H) |
| 234 | 0 | CH₃ | —CH₂—O—C(O)—NH—C₆H₅ | C₂H₅ | A | 7.6–6.5m(9H); 4.0m(2H); 1.2d(3H) |
| 235 | 0 | CH₃ | CH₂—COOH | H | A | 2.1m(2H); 1.2d(3H) |
| 236 | 0 | CH₃ | CH₂—CONH₂ | H | F | 6.5bs(2H); 2.1m(2H); 1.2d(3H) |
| 237 | 0 | CH₃ | CH₂—CON(CH₃)₂ | H | F | 3.9–3.0m+2s(10H); 2.1m(2H); 1.2d(3H) |
| 238 | 0 | CH₃ | CH₂—CONH—C₆H₅ | H | F | 7.3–6.5m(9H); 2.1m(2H); 1.2d(3H) |
| 239 | 0 | CH₃ | CH₂—CONH—C₆H₄CH₃ (3-CH₃) | H | F | 7.3–6.5m(8H); 2.3s(3H); 2.2m(2H); 1.2d(3H) |

-continued $$\begin{array}{c} \text{structure with } (CH_2)_n \text{ and } (CH_2)_n \text{ substituents on benzene ring,} \\ \text{CH-COOH, N-C(=O)-CH(R}^1\text{)-N(H)-CH(R}^2\text{)-COOR}^3 \end{array}$$

| No. | n | $R^1$ | $R^2$ | $R^3$ | Method | NMR |
|---|---|---|---|---|---|---|
| 240 | 0 | $CH_3$ | $CH_2-CON(H)-$(4-Cl-C$_6$H$_4$) | H | F | 7.7–6.5m(8H); 2.3m(2H); 1.2d(3H) |
| 241 | 0 | $CH_3$ | $CH_2-COOC_2H_5$ | H | F | 4.2q(2H); 2.0m(2H); 1.2d+t(6H) |
| 242 | 0 | $CH_3$ | $CH_2-CH_2-COOH$ | $C_2H_5$ | A | 2.1m(2H); 1.5m(2H); 1.2d(3H) |
| 243 | 0 | $CH_3$ | $CH_2-CH_2-CONH_2$ | $C_2H_5$ | A | 2.1m(2H); 1.5m(2H); 1.2d(3H) |
| 244 | 0 | $CH_3$ | $CH_2-CH_2-CON(CH_3)_2$ | $C_2H_5$ | A | 3.02s(6H); 1.5m(2H); 1.2d(3H) |
| 245 | 0 | $CH_3$ | $CH_2-CH_2-CON(H)-C_6H_5$ | $C_2H_5$ | A | 7.4–6.5m(9H); 2.1m(2H); 1.5m(2H); 1.2d(3H) |
| 246 | 0 | $CH_3$ | $CH_2-CH_2-CON(H)-$(4-F-C$_6$H$_4$) | H | A | 7.3–6.5m(8H); 2.1m(2H); 1.5m(2H); 1.2d(3H) |
| 247 | 0 | $CH_3$ | $CH_2-CH_2-CON(H)-$(4-OC$_2$H$_5$-C$_6$H$_4$) | $C_2H_5$ | A | 7.3–6.4m(8H); 3.6q(3H); 2.1m(2H); 1.5m(2H); 1.2d+t(6H) |
| 248 | 0 | $CH_3$ | $CH_2-CH_2-CON(H)-CH(CH_3)_2$ | $C_2H_5$ | A | 2.8–2.2m(3H); 1.5m(2H); 1.2d(3H); 1.0d(6H) |
| 249 | 0 | $CH_3$ | $CH_2-CH_2-CON(H)-CH_2-C_6H_5$ | $C_2H_5$ | A | 7.4–6.5m(9H); 5.1–4.3m+s(5H); 2.1m(2H); 1.5m(2H); 1.2d(3H) |

-continued

Structure:
$(CH_2)_n$-N(-(CH_2)-COOH)-C(=O)-CH(R^1)-N(H)-CH(R^2)-COOR^3

| No. | n | R¹ | R² | R³ | Method | NMR |
|---|---|---|---|---|---|---|
| 250 | 0 | CH₃ | CH₂-CH₂-CON(H)-CH₂-CH₂-(3,4-dimethoxyphenyl) | C₂H₅ | A | 7.3–6.2m(7H); 3.9s(6H); 2.9–2.1m(6H); 1.5m(2H); 1.2d(3H) |
| 251 | 1 | CH₃ | CH₂-CH₂-phenyl | C₂H₅ | B | 7.2bs(9H); 2.6m(2H); 1.7m(2H); 1.2d(3H) |
| 252 | 1 | CH₃ | CH₂-CH₂-phenyl | H | B | 7.2bs(9H); 2.6m(2H); 1.7m(2H) |
| 253 | 1 | CH₃ | CH₂-CH₂-(2-methylphenyl) | C₂H₅ | B | 7.4–7.0m(8H); 2.6m(2H); 2.3s(3H); 1.7m(2H); 1.2d(3H) |
| 254 | 1 | HO-CH₂ | CH₂-CH₂-phenyl | C₂H₅ | B | 7.2bs(9H); 2.8–2.5m(4H); 1.7m(2H) |
| 255 | 1 | H₂N-(CH₂)₄- | CH₂-CH₂-phenyl | H | B | 7.2bs(9H); 2.8–2.3m(4H); 1.8–1.3m(8H) |
| 256 | 1 | H₂N(CH₂)₃- | CH₂-CH₂-(3-nitrophenyl) | H | B | 8.2–7.1m(8H); 2.8–2.3m(4H) 1.8–1.3m(6H) |

-continued
| No. | n | R¹ | R² | R³ | Method | NMR |
|---|---|---|---|---|---|---|
| 257 | 1 | CH₃ | 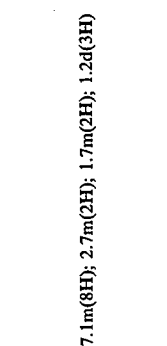 4-Cl-C₆H₄-CH₂-CH₂- | C₂H₅ | B | 7.5–6.9m(8H); 2.7m(2H); 1.7m(2H); 1.2d(3H) |
| 258 | 1 | CH₃ | 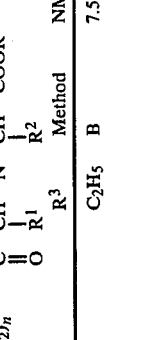 4-Cl-C₆H₄-CH₂-CH₂- | H | B | 7.5–6.9m(8H); 2.7m(2H); 1.7m(2H); 1.2d(3H) |
| 259 | 1 | CH₃ |  4-COOH-C₆H₄-CH₂-CH₂- | H | B | 7.8–7.1m(8H); 2.7m(2H); 1.7m(2H); 1.2d(3H) |
| 260 | 1 | HN=C(NH₂)-NH-(CH₂)₄- | 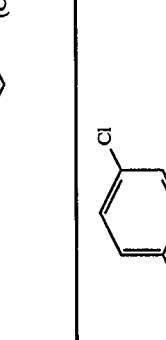 4-Cl-C₆H₄-CH₂-CH₂- | C₂H₅ | B | 7.5–7.0m(8H); 2.8–2.6(4H); 1.7–1.3m(6H) |
| 261 | 1 | H₂N-(CH₂)₂- | 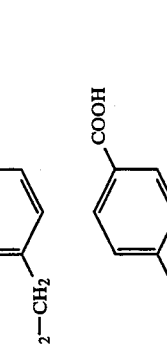 4-OH-C₆H₄-CH₂-CH₂- | H | B | 7.2–6.5m(8H); 2.8–2.3m(4H); 1.7–1.3m(4H) |
| 262 | 1 | H₂N-(CH₂)₅- | 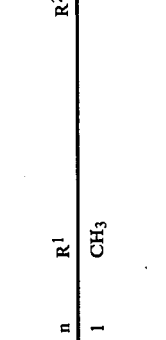 C₆H₅-CH₂-CH₂- | H | B | 7.2bs(9H); 2.7–2.3m(4H) 1.7–1.2m(10H) |
| 263 | 1 | H₂N-(CH₂)₄- |  4-CONH₂-C₆H₄-CH₂-CH₂- | H | B | 7.8–7.1m(8H); 2.7–2.3m(4H); 1.8–1.3m(8H) |

-continued

Structure:
$$\text{(CH}_2\text{)} - \text{CH(COOH)} - \text{N((CH}_2\text{)}_n\text{-aryl)} - \text{C(=O)} - \text{CR}^1\text{H} - \text{N(H)} - \text{CH(R}^2\text{)} - \text{COOR}^3$$

| No. | n | R¹ | R² | R³ | Method | NMR |
|---|---|---|---|---|---|---|
| 264 | 1 | H₂N—CH₂ | C₆H₅—CH₂—CH₂ | H | B | 7.2bs(9H); 2.7–2.3m(4H); 1.7m(2H) |
| 265 | 1 | CH₃ | 4-F-C₆H₄—CH₂—CH₂ | C₂H₅ | B | 7.2–6.8m(8H); 2.7m(2H); 1.7m(2H); 1.2d(3H) |
| 266 | 1 | CH₃ | 3,4-(OCH₃)₂-C₆H₃—CH₂—CH₂ | C₂H₅ | B | 7.2–6.3m(7H); 3.9s(6H); 2.7m(2H) 1.7m(2H); 1.2d(3H) |
| 267 | 1 | CH₃ | 4-Cl-2-OCH₃-C₆H₃—CH₂—CH₂ | C₂H₅ | B | 7.3–6.4m(7H); 3.8s(3H); 2.6m(2H) 1.7m(2H); 1.2d(3H) |
| 268 | 1 | CH₃ | 2,6-Cl₂-C₆H₃—CH₂—CH₂ | C₂H₅ | B | 7.4–6.8m(7H); 2.7m(2H); 1.7m(2H) 1.2d(3H) |
| 269 | 1 | imidazol-4-yl-CH₂ (HN=CH-N=CH-) | 3,4,5-(OCH₃)₃-C₆H₂—CH₂—CH₂ | C₂H₅ | B | 13.1s(1H); 7.5–6.2m(8H); 3.9s(9H) 2.8–2.3m(4H); 1.7m(2H) |

-continued
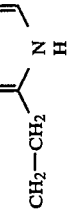
| No. | n | R¹ | R² | R³ | Method | NMR |
|---|---|---|---|---|---|---|
| 270 | 1 | CH₃ | 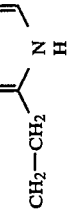 | C₂H₅ | B | 7.3–6.0m(7H); 2.8m(2H); 1.7m(2H); 1.2d(3H) |
| 271 | 1 | CH₃ | 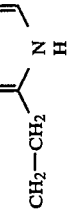 | C₂H₅ | B | 7.3–6.9m(7H); 2.9m(2H); 1.7m(2H); 1.2d(3H) |
| 272 | 1 | H₂N—(CH₂)₄ | 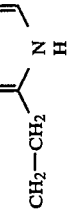 | H | B | 7.4–6.3m(7H); 2.8–2.3m(4H); 1.8–1.3m(8H) |
| 273 | 1 | CH₃ | 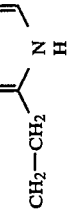 | C₂H₅ | B | 8.6–7.1m(8H); 2.9m(2H); 1.7m(2H); 1.2d(3H) |
| 274 | 1 | CH₃ | 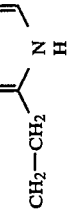 | C₂H₅ | B | 7.8–6.5m(10H); 2.9m(2H); 1.7m(2H); 1.2d(3H) |
| 275 | 1 | CH₃ |  | C₂H₅ | B | 7.4–7.0m(5H); 3.9–3.0m+s(7H); 2.8m(2H); 2.0s(3H); 1.7m(2H); 1.2d(3H) |

-continued

| No. | n | R¹ | R² | R³ | Method | NMR |
|---|---|---|---|---|---|---|
| 276 | 1 | CH₃ | ![structure: CH₃-N, C=O, N-CH₃, CH₂-CH₂ dimethyluracil-like] | C₂H₅ | B | 5.2s(1H); 3.2 2s(6H); 2.9m(2H); 1.7m(2H); 1.2d(3H) |
| 277 | 1 | CH₃ | ![structure: chloro-dimethyluracil with CH₂-CH₂] | C₂H₅ | B | 8.1s(1H); 3.2s(3H); 2.9m(2H); 1.7m(2H); 1.2d(3H) |
| 278 | 1 | CH₃ | ![structure: isoquinoline with CH₂-CH₂] | C₂H₅ | B | 8.5–7.5m(6H); 3.1m(2H); 1.8m(2H); 1.2d(3H) |
| 279 | 1 | CH₃ | ![structure: quinoline with CH₂-CH₂] | C₂H₅ | B | 8.8–7.4m(6H); 3.0m(2H); 1.7m(2H); 1.2d(3H) |
| 280 | 1 | CH₃ | ![structure: triazole HN-N=N with CH₂-CH₂] | C₂H₅ | B | 13.0s(1H); 2.9m(2H); 1.8m(2H); 1.2d(3H) |
| 281 | 1 | CH₃ | ![structure: oxazole with CH₂-CH₂] | C₂H₅ | B | 7.9–7.4 2s(2H); 2.8m(2H); 1.7m(2H); 1.2d(3H) |

-continued

Structure header:

$$\text{Ar}(CH_2)_n\text{-N} \begin{array}{c} \text{CH(COOH)-(CH}_2\text{)} \\ \text{C(=O)-CH(R}^1\text{)-NH-CH(R}^2\text{)-COOR}^3 \end{array}$$

(Table with columns: No. | n | R¹ | R² | R³ | Method | NMR)

| No. | n | R¹ | R² | R³ | Method | NMR |
|---|---|---|---|---|---|---|
| 282 | 1 | CH$_3$ | $H_2N$-thiazolyl-CH$_2$-CH$_2$- | C$_2$H$_5$ | B | 8.0s(1H); 2.8m(2H); 1.7m(2H); 1.2d(3H) |
| 283 | 1 | CH$_3$ | CH$_3$-N(C(=O))-N(CH$_3$)-C(Cl)=C-CH$_2$-CH$_2$- | C$_2$H$_5$ | B | 3.2 2s(6H); 3.1m(2H); 1.8m(2H) 1.2d(3H) |
| 284 | 1 | CH$_3$ | CH$_3$-CH(C$_6$H$_5$)- | C$_2$H$_5$ | B | 7.2bs(9H); 2.7m(2H); 2.2m(1H); 1.2d(3H); 1.0d(3H) |
| 285 | 1 | H$_2$N-(CH$_2$)$_4$- | 4-Cl-C$_6$H$_4$-CH$_2$-CH$_2$- | H | B | 7.4–7.0m(8H); 2.7–2.3m(4H); 1.8–1.3m(10H) |
| 286 | 1 | CH$_3$ | 4-OCH$_3$-C$_6$H$_4$-C(CH$_3$)$_2$-CH$_2$-CH$_2$- | C$_2$H$_5$ | B | 7.3–6.3m(8H); 3.9s(3H); 1.9–1.2m(4H); 1.2d(3H); 1.0s(6H) |
| 287 | 1 | HN=C(NH$_2$)-NH-(CH$_2$)$_3$- | C$_6$H$_5$-CH$_2$- | H | B | 7.2bs(9H); 2.9–2.6m(4H); 1.7–1.3m(4H); |
| 288 | 1 | H | 2-F-C$_6$H$_4$-CH$_2$- | H | B | 7.4–6.9m(8H); 3.9–3.0m(5H); 2.7m(2H) |

-continued

| No. | n | R¹ | R² | R³ | Method | NMR |
|-----|---|----|----|----|--------|-----|
| 289 | 1 | H | 4-COOH-benzyl (CH₂-C₆H₄-COOH) | H | B | 7.8–7.0m(8H); 3.9–3.0m(5H); 2.7m(2H) |
| 290 | 1 | H | —CH₂—CH₂—CH₂—(3-hydroxyphenyl) | H | B | 7.3–6.5m(8H); 3.9–3.0m(5H); 2.7m(2H); 1.8–1.3m(6H) |
| 291 | 1 | CH₃ | 4-CONH₂-benzyl | H | B | 7.8–7.0m(8H); 2.8m(2H); 1.2d(3H) |
| 292 | 1 | CH₃ | 4-NH₂-benzyl | H | B | 7.2–6.4m(8H); 2.7m(2H); 1.2d(3H) |
| 293 | 1 | CH₃ | 2,4-dimethoxybenzyl | H | B | 7.2–6.3m(7H); 3.9s(6H); 2.7m(2H); 1.2d(3H) |
| 294 | 1 | (CH₃)₂CH—CH₂ | 2-methoxy-4-chlorobenzyl | C₂H₅ | B | 7.2–6.4m(7H); 3.8s(3H); 2.8m(2H); 2.0–1.5m(5H); 0.9d(6H) |

-continued
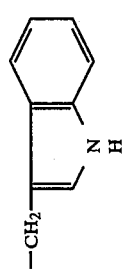
| No. | n | R¹ | R² | R³ | Method | NMR |
|---|---|---|---|---|---|---|
| 295 | 1 | CH₃ | 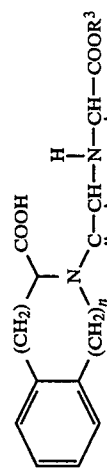 | C₂H₅ | B | 7.8–6.5m(10H); 2.9m (2H); 1.2d(3H) |
| 296 | 1 | (CH₃)₂CH—CH₂ | 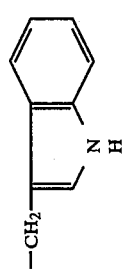 | H | B | 7.2–6.2m(6H); 3.9s(9H); 2.7m(2H); 1.9–1.3m(5H); 0.9d(6H) |
| 297 | 1 | CH₃ | 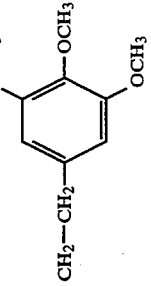 | H | B | 7.3–6.0m(7H); 2.8m(2H); 1.2d(3H) |
| 298 | 1 | CH₃ | 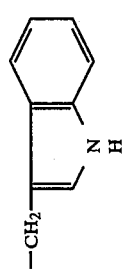 | H | B | 7.3–6.9m(7H); 2.9m(2H); 1.2d(3H) |
| 299 | 1 | CH₃ | 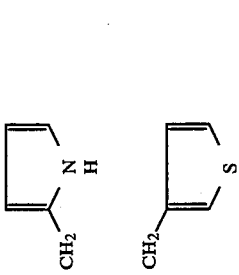 | H | B | 7.4–6.3m(7H); 2.8m(2H); 1.2d(3H) |
| 300 | 1 | CH₃ | 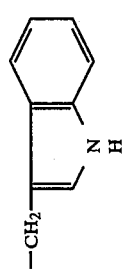 | H | B | 8.6–7.1m(8H); 2.9m(2H); 1.2d(3H) |

-continued
| No. | n | R¹ | R² | R³ | Method | NMR |
|---|---|---|---|---|---|---|
| 301 | 1 | CH₃ | 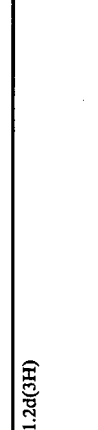 | H | B | 7.8–6.5m(10H); 2.9m(2H); 1.2d(3H) |
| 302 | 1 | (CH₃)₂CH—CH₂ |  | C₂H₅ | B | 7.4–7.0m(5H); 3.9–3.0m+s(7H); 2.8m(2H); 2.0s(3H); 1.8–1.3m(3H); 1.0d(6H) |
| 303 | 1 | H |  | C₂H₅ | B | 5.2s(1H); 3.2s(6H); 2.9m(2H) |
| 304 | 1 | CH₃ |  | H | B | 8.5–7.5m(6H); 3.1m(2H); 1.2d(3H) |
| 305 | 1 | CH₃ |  | H | B | 8.8–7.4m(6H); 3.0m(2H); 1.2d(3H) |
| 306 | 1 | CH₃ | (thiazole-CH₂—) | H | B | 8.0s(1H); 2.8m(2H); 1.2d(3H) |

-continued

Structure:

$$\text{Ph-ring with (CH}_2\text{)- and (CH}_2\text{)}_n\text{- substituents, where (CH}_2\text{)- attaches to CH(COOH)-N(H)-C(=O)-CH(R}^1\text{)-N(H)-CH(R}^2\text{)-COOR}^3$$

| No. | n | R¹ | R² | R³ | Method | NMR |
|---|---|---|---|---|---|---|
| 307 | 1 | CH₃ | CH₂– attached to 3-methoxy-4H-pyran-4-one (CH₃O, =O) | H | B | 8.1s(1H); 6.4s(1H); 3.7s(3H); 2.9m(2H); 1.2d(3H) |
| 308 | 1 | (CH₃)₂CH—CH₂ | CH₂—CH₂ attached to 3-methoxy-4H-pyran-4-one (CH₃O, =O) | H | B | 8.1s(1H); 6.4s(1H); 3.7s(3H); 2.9m(2H); 1.8–1.3m(5H); 1.0d(6H) |
| 309 | 1 | CH₃ | CH₂—CH₂– attached to 1H-imidazole | C₂H₅ | B | 7.7–7.1m(6H); 2.9m(2H); 1.7m(2H) 1.2d(3H) |
| 310 | 1 | CH₃ | CH₂– attached to 1H-imidazole | C₂H₅ | B | 7.7–7.1m(6H); 2.9m(2H), 1.2d(3H) |
| 311 | 0 | CH₃ | CH₂—CH₂– phenyl | C₂H₅ | B | 7.2–6.5m(9H); 2.7m(2H); 1.7m(2H); 1.2d(3H) |
| 312 | 0 | CH₃ | CH₂—CH₂– (4-chlorophenyl) | H | B | 7.5–6.5m(8H); 2.7m(2H); 1.7m(2H); 1.2d(3H) |

-continued

Structure:

$$\text{Ar-(CH}_2)\text{-CH(COOH)-N(H)-(CH}_2)_n\text{-C(=O)-CR}^1\text{H-N(H)-CHR}^2\text{-COOR}^3$$

where the Ar portion is a phenyl ring with ortho-substituted (CH₂) and (CH₂)ₙ linkers.

| No. | n | R¹ | R² | R³ | Method | NMR |
|-----|---|-----|-----|-----|--------|-----|
| 313 | 0 | CH₃ | 2,6-dichlorobenzyl (–CH₂–C₆H₃Cl₂) | H | B | 7.6–6.5m(7H); 2.8m(2H); 1.7m(2H); 1.2d(3H) |
| 314 | 0 | CH₃ | –CH₂–CH₂–(pyrrol-2-yl, NH) | H | B | 7.3–6.0m(7H); 2.8m(2H); 1.7m(2H); 1.2d(3H) |
| 315 | 0 | CH₃ | –CH₂–CH₂–(thien-2-yl) | H | B | 7.3–6.5m(7H); 2.9m(2H); 1.7m(2H); 1.2d(3H) |
| 316 | 0 | CH₃ | –CH₂–CH₂–(pyridin-3-yl) | H | B | 8.6–6.5m(8H); 2.9m(2H); 1.7m(2H); 1.2d(3H) |
| 317 | 0 | CH₃ | –CH₂–CH₂–(indol-3-yl) | C₂H₅ | B | 7.8–6.5m(10H); 2.9m(2H); 1.7m(2H); 1.2d(3H) |
| 318 | 0 | CH₃ | –CH(CH₃)–C₆H₅ | C₂H₅ | B | 7.2–6.5m(9H); 2.9m(2H); 1.8m(1H); 1.2d(3H); 1.1d(3H) |
| 319 | 0 | CH₃ | –CH₂–CH₂–CH₂–(4-chlorophenyl) | C₂H₅ | B | 7.4–6.5m(8H); 2.7–2.3m(2H); 1.8–1.3m(4H); 1.2d(3H) |

-continued

Structure:

(CH₂)ₙ—N—CH₂—COOH
         |
         C=O
         |
         CH—N—CH—COOR³
         |   H  |
         R¹    R² with phenyl ring bearing (CH₂)ₙ and (CH₂) substituents (ortho-disubstituted benzene)

| No. | n | R¹ | R² | R³ | Method | NMR |
|---|---|---|---|---|---|---|
| 320 | 0 | CH₃ | –CH₂–C(CH₃)₂–CH₂–C₆H₄–OCH₃ (p-methoxy, with gem-dimethyl) | C₂H₅ | B | 7.3–6.3m(8H); 3.9s(3H); 1.9–1.2m(4H 1.2d(3H); 1.0s(6H) |
| 321 | 0 | CH₃ | –CH₂–CH₂–C₆H₃(OCH₃)(?) | C₂H₅ | B | 7.2–6.3m(7H); 3.9s(3H); 2.7m(2H); 1.8m(2H); 1.2d(3H) |
| 322 | 0 | CH₃ | –CH₂– (indol-3-yl-methyl) | C₂H₅ | B | 7.8–6.5m(10H); 2.9m(2H); 1.2d(3H) |
| 323 | 0 | CH₃ | –CH₂–CH₂– (imidazol-4-yl) | C₂H₅ | B | 7.7–6.5m(6H); 2.9m(2H); 1.7m(2H); 1.2d(3H) |
| 324 | 0 | CH₃ | –CH₂– (imidazol-4-yl) | C₂H₅ | B | 7.7–6.5m(6H); 2.9m(2H); 1.2d(3H) |
| 325 | 1 | CH₃ | (CH₃)₂–CH–CH₂–CH₂–CH₂ | C₂H₅ | A | 1.9–1.3m(7H); 1.2d(3H); 0.9d(6H) |
| 326 | 1 | H₂N–(CH₂)₄ | (CH₃)₂CH–CH₂–CH₂ | C₂H₅ | B | 2.4m(2H); 1.9–1.3m(11H); 0.9d(6H) |
| 327 | 1 | H₂N–(CH₂)₃ | (CH₃)₂CH–CH₂ | C₂H₅ | B | 2.4m(2H); 1.9–1.3m(7H); 0.9d(6H) |
| 328 | 0 | FCH₃ | (CH₃)₂CH | C₂H₅ | B | 4.3dd(2H); 1.9m(1H); 0.9d(6H) |

-continued

Structural formula:

$$\text{Ar}[(CH_2)-CH(COOH)-N((CH_2)_n-)-C(=O)-CH(R^1)-NH-CH(R^2)-COOR^3]$$

where Ar is a 1,2-disubstituted benzene ring.

| No. | n | R¹ | R² | R³ | Method | NMR |
|-----|---|----|----|----|--------|-----|
| 329 | 1 | CH₃—CH₂—CH(CH₃)— | cyclohexyl-CH₂- (H) | H | A | 1.9-1.2m(16H); 1.0d+t(6H) |
| 330 | 1 | CH₃ | 2-naphthyl-CH₂-CH₂- | C₂H₅ | A | 7.8-7.0m(11H); 2.7m(2H); 1.5m(2H); 1.2d(3H) |
| 331 | 1 | CH₃ | 4-HO-C₆H₄-CH₂- | H | B | 7.3-6.5m(8H); 2.8m(2H); 1.2d(3H) |
| 332 | 1 | CH₃ | 4-CH₃O-C₆H₄-CH₂- | H | B | 7.3-6.4m(8H); 3.9s(3H); 2.9m(2H); 1.2d(3H) |
| 333 | 1 | CH₃ | 3-CH₃O-C₆H₄-CH₂- | C₂H₅ | B | 7.6-6.4m(8H); 3.8s(3H); 2.9m(2H); 1.2d(3H) |
| 334 | 1 | CH₃ | 4-Cl-C₆H₄-CH₂- | C₂H₅ | B | 7.6-7.0m(8H); 2.9m(5H); 1.2d(3H) |
| 335 | 1 | CH₃ | 3,4-Cl₂-C₆H₃-CH₂- | H | B | 7.8-7.0m(7H); 2.9m(2H); 1.2d(3H) |

-continued

| No. | n | R¹ | R² | R³ | Method | NMR |
|---|---|---|---|---|---|---|
| 336 | 1 | CH₃ | 4-NO₂-C₆H₄-CH₂ | H | B | 8.3–7.0m(8H); 2.9m(2H); 1.2d(3H) |
| 337 | 1 | CH₃ | 4-CH₃-C₆H₄-CH₂ | C₂H₅ | B | 7.4–7.0m(8H); 2.9m(2H); 2.3s(3H); 1.2d(3H) |
| 338 | 1 | CH₃ | cycloheptenyl | H | A | 5.3m(1H); 2.3m(4H); 1.8–1.3m(6H); 1.2d(3H) |
| 339 | 1 | CH₃ | cyclohexenyl | H | A | 5.4m(1H); 2.3m(4H); 1.8–1.4m(4H); 1.2d(3H) |
| 340 | 1 | CH₃ | thiopyranyl | H | A | 5.5m(1H); 3.9–3.0m(6H); 2.5–2.1m(4H) 1.2d(3H) |
| 341 | 1 | CH₃ | dithianyl | H | A | 5.9s(1H); 3.9–3.0m(8H); 1.2d(3H) |

-continued

Structure: Ar-(CH₂)-CH(COOH)-N((CH₂)ₙ-)-C(=O)-CH(R¹)-N(H)-CH(R²)-COOR³ where Ar is a phenyl ring with ortho-disubstitution forming a ring.

| No. | n | R¹ | R² | R³ | Method | NMR |
|---|---|---|---|---|---|---|
| 342 | 1 | CH₃ | 4,6-dimethylpyrimidin-2-yl-NH(CH₂)₃— | C₂H₅ | A | 7.4s(1H); 2.5m(2H); 2.3s(6H); 1.8-1.2m(4H) |
| 343 | 1 | CH₃ | benzimidazol-2-yl-CH₂CH₂— | C₂H₅ | A | 7.5-6.8m(8H); 2.8m(2H); 1.5m(2H) |
| 344 | 1 | CH₃ | benzimidazol-2-yl-CH₂CH₂— | H | A | 7.5-6.8m(8H); 2.8m(2H); 1.5m(2H) |

Structure:

$$\text{cyclohexane-CH}_2\text{-CH(COOH)-N((CH}_2)_n\text{)-C(=O)-CH(R}^1\text{)-NH-CH(R}^2\text{)-COOR}^3$$

| No. | n | R¹ | R² | R³ | Method | NMR |
|---|---|---|---|---|---|---|
| 345 | 1 | CH₃ | −CH₂−NH−CHO | C₂H₅ | A | 8.3s(1H); 2.9m((2H); 1.2d(3H) |
| 346 | 1 | CH₃ | −CH₂−NH−COCH₃ | C₂H₅ | A | 2.9m(2H); 2.1s(3H); 1.2d(3H) |
| 347 | 1 | CH₃ | −CH₂−NH−CO−CH₂−C₆H₅ | C₂H₅ | A | 3.9−3.0m(5H); 2.9m(2H); 1.2d(3H) |
| 348 | 1 | H | −CH₂−NH−CO−(2-OH-C₆H₄) | C₂H₅ | A | 7.2−6.8m(4H); 3.9−3.0m(4H); 2.9m(2H) |
| 349 | 1 | H | −CH₂−NH−CO−(2-COOH-C₆H₄) | C₂H₅ | A | 7.9−7.4m(4H); 3.9−3.0m(4H); 2.9m(2H) |
| 350 | 1 | CH₃ | −CH₂−NH−CO−CH₂−(3-Cl-C₆H₄) | C₂H₅ | A | 7.65−7.1m(4H); 3.9−3.0m(5H); 2.9m(2H); 1.2d(3H) |
| 351 | 1 | CH₃ | −CH₂−NH−CO−CH₂−(3-Cl-C₆H₄) | H | A | 7.65−7.1m(4H); 3.9−3.0m(5H); 2.9m(2H); 1.2d(3H) |

-continued

[Structure: cyclohexane with CH2-COOH and (CH2)n-N(C(=O)-CH(R1)-NH-CH(R2)-COOR3) substituents]

| No. | n | R¹ | R² | R³ | Method | NMR |
|---|---|---|---|---|---|---|
| 352 | 1 | CH₃ | CH₂-NH-CO-(3-NO₂-C₆H₄) | C₂H₅ | A | 8.2–7.6m(4H); 2.9m(2H); 1.2d(3H) |
| 353 | 1 | CH₃ | CH₂-NH-CO-(3-NH₂-C₆H₄) | C₂H₅ | A | 7.2–6.8m(4H); 2.9m(2H); 1.2d(3H) |
| 354 | 1 | CH₃ | CH₂-(imidazole) | C₂H₅ | A | 13.0s(1H); 7.5–7.0m(6H); 3.9s(3H); 2.9–2.6m(4H) |
| 355 | 1 | CH₃ | CH₂-NH-CO-(4-OCH₃-C₆H₄) | C₂H₅ | A | 7.5–6.9m(3H); 3.9s(6H); 2.9m(2H); 1.2d(3H) |
| 356 | 1 | CH₃ | CH₂-NH-CO-(3,4,5-tri-OCH₃-C₆H₂) | C₂H₅ | A | 7.3–6.8m(2H); 3.9s(9H); 2.9m(2H) 1.2d(3H) |

-continued

Structure: CH₂(cyclohexyl)-CH(COOH)-N((CH₂)ₙ-...)-C(=O)-CH(R¹)-NH-CH(R²)-COOR³

| No. | n | R¹ | R² | R³ | Method | NMR |
|---|---|---|---|---|---|---|
| 357 | 1 | CH₃ | CH₂-NH-CO-(2-CH₃-C₆H₄) | C₂H₅ | A | 7.6-7.0m(4H); 2.9m(2H); 2.4s(3H); 1.2d(3H) |
| 358 | 1 | CH₃ | CH₂-NH-CO-(2-CH₃-C₆H₄) | C₂H₅ | A | 7.4-7.0m(4H); 2.9m(2H); 2.4s(3H); 1.2d(3H) |
| 359 | 1 | CH₃ | CH₂-CH₂-N(CH₃)₂ | C₂H₅ | A | 2.4m(2H); 2.2s(6H); 2.1-1.0m(14H) 1.2d(3H) |
| 360 | 1 | CH₃ | CH₂-NH-CO-NH-C₆H₅ | C₂H₅ | A | 7.3-7.0m(5H); 2.9m(2H); 1.2d(3H) |
| 361 | 1 | CH₃ | CH₂-NH-CO-NH-(4-Cl-C₆H₄) | C₂H₅ | A | 8.0-7.0m(4H); 2.9m(2H); 1.2d(3H) |
| 362 | 1 | CH₃ | CH₂-NH-CO-NH-(3-NO₂-C₆H₄) | C₂H₅ | A | 8.3-7.1m(4H); 2.9m(2H); 1.2d(3H) |
| 363 | 1 | (CH₃)₂CH-CH₂ | CH₂-NH-CO-NH-(3-CH₃-C₆H₄) | C₂H₅ | A | 7.4-7.0m(4H); 2.9m(2H); 2.3s(3H) 1.0d(6H) |

-continued

[Structure: cyclohexyl-CH(CH₂-)-with (CH₂)ₙ chain to N(H)-C(=O)-CH(R¹)-N(H)-CH(R²)-COOR³, with COOH on the central carbon]

| No. | n | R¹ | R² | R³ | Method | NMR |
|---|---|---|---|---|---|---|
| 364 | 1 | CH₃ | CH₂—N(H)—CO—N(H)—(2-OCH₃-phenyl) | C₂H₅ | A | 7.3–6.7m(4H); 3.8s(3H); 2.9m(2H); 1.2d(3H) |
| 365 | 1 | CH₂—S—phenyl | CH₂—N(H)—CO—N(H)—(2-OCH₃-phenyl) | C₂H₅ | A | 7.3–6.7m(4H); 3.8s(3H); 2.9m(2H); 1.2d(3H) |
| 366 | 1 | CH₂—S—phenyl | CH₂—N(H)—CO—N(H)—CH₃ | C₂H₅ | A | 7.3–7.0m(5H); 3.0–2.6m+s(7H) |
| 367 | 1 | CH₂—S—phenyl | CH₂—N(H)—CO—N(H)—CH₃ | H | A | 7.3–7.0m(5H); 3.0–2.6m+s(7H) |
| 368 | 1 | CH₂F | CH₂—N(H)—CO—N(H)—C₄H₉ | C₂H₅ | A | 5.1–4.3m(4H); 2.9m(2H); 1.0t(3H) |
| 369 | 1 | CH₃ | CH₂—N(H)—C(=O)—N(H)—cyclohexyl | C₂H₅ | A | 3.2–2.9m(3H); 2.4–1.0m(22H); 1.2d(3H) |

-continued $$\text{structure with } CH_2\text{-cyclohexyl, COOH, }(CH_2)_n\text{, N-C(=O)-CH(R}^1\text{)-N(H)-CH(R}^2\text{)-COOR}^3$$

| No. | n | R¹ | R² | R³ | Method | NMR |
|---|---|---|---|---|---|---|
| 370 | 1 | CH₃ | CH₂—N(H)—C(=O)—O—CH₂—C₆H₅ | C₂H₅ | A | 7.1s(5H); 5.0s(2H); 2.9m(2H); 1.2d(3H) |
| 371 | 1 | CH₃ | CH₂—N(H)—C(=O)—O—C₂H₅ | C₂H₅ | A | 4.2q(4H); 2.9m(2H); 1.2t+d(9H) |
| 372 | 1 | CH₃ | CH₂—CH₂—N(H)—CHO | C₂H₅ | G | 8.2–2s(1H); 2.9m(2H); 2.0–1.0m(14H) |
| 373 | 1 | H | CH₂—CH₂—N(H)—COOCH₃ | C₂H₅ | G | 3.9–3.0m(5H); 2.9m(2H); 2.1s(3H); 1.5m(2H) |
| 374 | 1 | CH₃ | CH₂—CH₂—N(H)—CO—C₆H₅ | C₂H₅ | G | 7.6–7.0m(5H); 2.9m(2H); 2.0–1.0m(14H) |
| 375 | 1 | CH₂—C₆H₅ | CH₂—CH₂—N(H)—CO—(2-HO-C₆H₄) | C₂H₅ | G | 7.2–6.8m(4H); 2.9m(2H); 2.0–1.0m(14H) |
| 376 | 1 | CH₃ | CH₂—CH₂—N(H)—CO—(2-COOH-C₆H₄) | C₂H₅ | G | 7.9–7.4m(9H); 2.9–2.7m(4H); 2.0–1.0m(14H) |
| 377 | 1 | CH₃ | CH₂—CH₂—N(H)—CO—(4-Cl-C₆H₄) | C₂H₅ | G | 8.0–7.1m(4H); 2.9m(2H); 2.0–1.0m(14H) |

-continued

Structure:

$$\text{cyclohexyl-CH}_2\text{-CH(COOH)-N((CH}_2)_n\text{-R}^2)\text{-C(=O)-CH(R}^1)\text{-NH-CH(R}^2)\text{-COOR}^3$$

| No. | n | R¹ | R² | R³ | Method | NMR |
|---|---|---|---|---|---|---|
| 378 | 1 | CH₃ | CH₂–CH₂–NH–C(=O)–(4-Cl-C₆H₄) | H | G | 8.0–7.1m(4H); 2.9m(2H); 2.0–1.0m(14H) |
| 379 | 1 | CH₃ | CH₂–CH₂–NH–C(=O)–(3-NO₂-C₆H₄) | C₂H₅ | G | 8.3–7.6m(4H); 2.9m(2H) 2.0–1.0m(14H) |
| 380 | 1 | CH₃ | CH₂–CH₂–NH–C(=O)–(3-NH₂-C₆H₄) | C₂H₅ | G | 7.2–6.8m(4H); 2.9m(2H); 1.2d(3H); 2.0–1.0m(14H) |
| 381 | 1 | CH₃ | CH₂–CH₂–NH–C(=O)–(4-OCH₃-C₆H₄) | C₂H₅ | G | 7.5–6.8m(4H); 3.8s(3H); 2.9m(2H); 1.2d(3H); 2.0–1.0m(14H) |
| 382 | 1 | CH₃ | CH₂–CH₂–NH–C(=O)–(3,4-(OCH₃)₂-C₆H₃) | C₂H₅ | G | 7.5–6.9m(3H); 3.9s(6H); 2.9m(2H); 1.2d(3H); 2.0–1.0m(14H) |
| 383 | 1 | CH₃–CH₂–CH(CH₃)–CH₂ | CH₂–CH₂–NH–C(=O)–(3,4,5-(OCH₃)₃-C₆H₂) | C₂H₅ | G | 7.2–6.8m(6H); 3.9s(9H); 2.9m(2H); 2.0–1.0m(25H) |

-continued $$\begin{array}{c} CH_2 \\ | \\ CH \\ / \\ (CH_2)_n \end{array} \begin{array}{c} COOH \\ | \\ N-C-CH-N-CH-COOR^3 \\ | \\ O \ R^1 \ R^2 \end{array}$$
(with cyclohexyl ring)

| No. | n | R¹ | R² | R³ | Method | NMR |
|-----|---|-----|-----|-----|--------|-----|
| 384 | 1 | CH₃ | CH₂—CH₂—N(H)—CO—(2-methylphenyl) | C₂H₅ | G | 7.6–7.2m(4H); 2.9m(2H); 2.3s(3H); 1.2d(3H); 2.0–1.0m(14H) |
| 385 | 1 | CH₃ | CH₂—CH₂—N(H)—CO—(2-methylphenyl) | H | G | 7.6–7.2m(4H); 2.9m(2H); 2.3s(3H); 1.2d(3H); 2.0–1.0m(14H) |
| 386 | 1 | CH₃ | CH₂—CH₂—CH₂—N(C₂H₅)₂ | C₂H₅ | G | 2.6–2.4m(6H); 2.0–1.0m(14H); 1.2d(3H), 0.9t(6H) |
| 387 | 1 | CH₃ | CH₂—CH₂—N(H)—CO—phenyl | C₂H₅ | G | 7.5–7.0m(5H); 2.9m(2H); 2.0–1.0m(14H); 1.2d(3H) |
| 388 | 1 | CH₃ | CH₂—CH₂—N(H)—CO—(4-chlorophenyl) | C₂H₅ | G | 7.5–7.0m(4H); 2.9m(2H); 2.0–1.0m(14H); 1.2d(3H) |
| 389 | 1 | CH₃ | CH₂—CH₂—N(H)—CO—(3-nitrophenyl) | C₂H₅ | G | 8.3–7.3m(4H); 2.9m(2H); 2.2–1.0m(14H); 1.2d(3H) |

-continued

| No. | n | R¹ | R² | R³ | Method | NMR |
|---|---|---|---|---|---|---|
| 390 | 1 | CH₃ | CH₂—CH₂—N(H)—CO—N(H)—(2-methylphenyl) | C₂H₅ | G | 7.4-7.0m(4H); 2.9m(2H); 2.3s(3H); 2.1-1.0m(14H) 1.2d(3H) |
| 391 | 1 | CH₃ | CH₂—CH₂—N(H)—CO—N(H)—(4-methoxyphenyl) | C₂H₅ | G | 7.2-6.5m(4H); 3.9s(3H); 2.9m(2H); 2.0-1.0m(14H); 1.2d(3H) |
| 392 | 1 | CH₃ | CH₂—CH₂—N(H)—CO—N(H)—(3-fluoro-4-methylphenyl) | C₂H₅ | G | 7.3-6.9m(3H); 2.9m(2H); 2.3s(3H); 2.0-1.0m(14H) 1.2d(3H) |
| 393 | 1 | (CH₃)₂CH—CH₂ | CH₂—CH₂—N(H)—CO—N(H)—CH₃ | C₂H₅ | G | 3.0-2.6m(5H); 2.0-1.0m(17H); 1.0d (6H) |
| 394 | 1 | (CH₃)₂CH—CH₂ | CH₂—CH₂—N(H)—CO—N(H)—C₄H₉ | C₂H₅ | G | 3.0-2.6m(4H); 2.0-1.0m(21H); 0.9+t(9H) |
| 395 | 1 | (CH₃)₂CH—CH₂ | CH₂—CH₂—N(H)—CO—N(H)—C₄H₉ | H | G | 3.0-2.6m(4H); 2.0-1.0m(21H); 0.9+t(9H) |
| 396 | 1 | CH₂F | CH₂—CH₂—N(H)—CO—N(H)—cyclohexyl | C₂H₅ | G | 5.1-4.3m(4H); 2.9m(3H); 2.0-1.0m(24H) |
| 397 | 1 | CH₃ | CH₂—CH₂—N(H)—CO—O—CH₂—phenyl | C₂H₅ | G | 7.1s(5H); 5.0s(2H); 2.9m(2H); 2.0-1.0m(14H); 1.2d(3H) |

-continued

![structure: cyclohexyl-CH2-CH(COOH)-N((CH2)n-)-C(=O)-CH(R1)-NH-CH(R2)-COOR3]

| No. | n | R¹ | R² | R³ | Method | NMR |
|---|---|---|---|---|---|---|
| 398 | 1 | CH₃ | CH₂—CH₂—N(H)—CO—O—C₂H₅ | C₂H₅ | A | 4.2q(4H); 2.9m(2H); 2.0-1.0m(14H); 1.2+t(9H) |
| 399 | 1 | CH₃ | CH₂—CH₂—N(H)—CH₃ | C₂H₅ | A | 2.4m(2H); 2.3s(3H); 2.0-10m(14H); 1.2d(3H) |
| 400 | 1 | CH₃ | CH₂—CH₂—N(piperidine) | C₂H₅ | A | 2.4m(6H); 2.0-1.0m(20H); 1.2d(3H) |
| 401 | 1 | CH₃ | CH₂—CH₂—N(H)—C₆H₅ | C₂H₅ | A | 7.0-6.5m(5H); 2.5-1.0m(16H); 1.2d(3H) |
| 402 | 1 | (CH₃)₂CH—CH₂ | CH₂—CH₂—N(H)—(3-Cl-C₆H₄) | C₂H₅ | A | 7.2-6.6m(4H); 2.4-1.0m(19H); 1.0d(6H) |
| 403 | 1 | C₆H₅—S—CH₂ | CH₂—CH₂—N(H)—(4-OCH₃-C₆H₄) | C₂H₅ | A | 7.3-6.4m(9H); 2.5-2.2m(4H); 2.0-1.0m(14H) |
| 404 | 1 | CH₂F | CH₂—CH₂—N(H)—(2-Cl-4-CH₃-C₆H₃) | C₂H₅ | A | 7.0-6.6m(3H); 5.1-4.3m(4H); 2.4m(2H); 2.3s(3H); 2.0-1.0m(14H) |

-continued

| | | | | | | |
|---|---|---|---|---|---|---|
| No. | n | $R^1$ | $R^2$ | $R^3$ | Method | NMR |
| 405 | 1 | $CH_3$ | 3-(OCOCH$_3$)-C$_6$H$_4$-NH-CH$_2$- | $C_2H_5$ | A | 7.0–6.5m(4H); 2.5–1.0m(14H); 2.1s(3H); 1.2d(3H) |
| 406 | 1 | $CH_3$ | 3-(NO$_2$)-C$_6$H$_4$-NH-CH$_2$- | $C_2H_5$ | A | 7.7–7.0m(4H); 2.5m(2H); 1.2d(3H) |
| 407 | 1 | $CH_3$ | 2-(OH)-4-(CONH$_2$)-C$_6$H$_3$-NH-CH$_2$- | $C_2H_5$ | A | 7.6–6.7m(3H); 2.4m(2H); 1.2d(3H) |
| 408 | 1 | $CH_3$ | 4-(COOC$_2$H$_5$)-C$_6$H$_4$-NH-CH$_2$- | $C_2H_5$ | A | 7.6–6.8m(4H); 4.2q(4H); 2.5m(2H); 1.2d+t(9H) |
| 409 | 1 | $CH_3$ | 3,4-(OCH$_2$O)-C$_6$H$_3$-NH-CH$_2$- | $C_2H_5$ | A | 6.8–6.2m(3H); 5.0s(2H); 2.5m(2H); 1.2d(3H) |
| 410 | 1 | $CH_3$ | 3-(NH$_2$)-C$_6$H$_4$-NH-CH$_2$- | $C_2H_5$ | A | 7.0–6.5m(8H); 2.5m(2H); 1.2d(3H) |

-continued $$\text{structure: cyclohexane with CH}_2\text{-CH(COOH)-N(-(CH}_2)_n\text{-)-C(=O)-CH(R}^1\text{)-NH-CH(R}^2\text{)-COOR}^3$$

| No. | n | R¹ | R² | R³ | Method | NMR |
|---|---|---|---|---|---|---|
| 411 | 1 | CH₃ | —CH₂—N(H)—CH₂—CH₂—COOC₂H₅ | C₂H₅ | A | 4.2q(4H); 2.6–2.3m(6H); 1.2d+t(9H) |
| 412 | 1 | CH₃ | CH₂—CH₂—CH₂—NH₂ | H | C | 2.3m(2H); 2.0–1.0m(16H); 1.2d(3H) |
| 413 | 1 | CH₃ | CH₂—N(H)—CH₂—CH₂—N(C₂H₅)₂ | C₂H₅ | A | 2.6–1.0m(22H); 1.2d+t(9H) |
| 414 | 1 | CH₃ | CH₂—N(morpholine) | C₂H₅ | A | 3.9–3.0m(12H); 2.3m(2H); 1.2d(3H) |
| 415 | 1 | CH₃ | CH₂—N(pyrrolidine) | C₂H₅ | A | 2.6–2.3m(6H); 2.1–1.0m(16H); 1.2d(3H) |
| 416 | 1 | CH₃ | CH₂—N(H)—CH₂—CH₂—CONH₂ | C₂H₅ | A | 2.6–2.2m(6H); 1.2d(3H) |
| 417 | 1 | CH₃ | CH₂—CH₂—CH₂—N(CH₃)₂ | C₂H₅ | A | 2.4m(2H); 2.2s(6H); 2.0–1.0(16H); 1.2d(3H) |
| 418 | 1 | CH₃ | CH₂—N(H)—CH₂—CONH₂ | C₂H₅ | A | 3.9–3.0m(5H); 2.4m(2H); 1.2d(3H) |
| 419 | 1 | CH₃ | (CH₂)₅—NH₂ | H | C | 2.3m(2H); 2.1–1.0m(20H); 1.2d(3H) |
| 420 | 1 | H₂N—(CH₂)₄ | (CH₂)₄—NH₂ | H | C | 2.4m(4H); 2.1–1.0m(24H) |
| 421 | 1 | CH₃ | CH₂—CH₂—NH—CH₃ | C₂H₅ | A | 2.4m(2H); 2.2s(3H); 2.0–1.0m(14H); 1.2d(3H) |
| 422 | 1 | CH₃ | CH₂—NH—CH₃ | C₂H₅ | A | 2.4m(2H); 2.1s(3H); 1.2d(3H) |
| 423 | 0 | CH₃ | CH₂—N(H)—CO—CH₂—C₆H₅ | C₂H₅ | A | 7.0s(5H); 4.5–3.0m(5H); 2.9m(2H); 1.2d(3H) |

-continued

Structure:

$$\text{cyclohexane-CH}_2\text{-(CH}_2)_n\text{-N(-CH(COOH))-C(=O)-CH(R}^1\text{)-NH-CH(R}^2\text{)-COOR}^3$$

| No. | n | R¹ | R² | R³ | Method | NMR |
|---|---|---|---|---|---|---|
| 424 | 0 | CH₃ | -CH₂-NH-CO-C₆H₅ | C₂H₅ | A | 7.4-7.3m(5H); 2.9m(2H); 1.2d(3H) |
| 425 | 0 | CH₃ | -CH₂-NH-CO-C₆H₄-Cl (4-Cl) | C₂H₅ | A | 7.8-7.2m(4H); 2.9m(2H); 1.2d(3H) |
| 426 | 0 | CH₃ | -CH₂-NH-CO-NH-C₆H₅ | C₂H₅ | A | 7.4-6.8m(5H); 2.9m(2H); 1.2d(3H) |
| 427 | 0 | CH₃ | -CH₂-NH-CO-NH-C₆H₄-Cl (4-Cl) | C₂H₅ | A | 7.7-6.5m(4H); 2.9m(2H); 1.2d(3H) |
| 428 | 0 | CH₃ | -CH₂-NH-CO-NH-CH₃ | C₂H₅ | A | 3.0-2.6m+s(5H); 1.2d(3H) |
| 429 | 0 | CH₃ | -CH₂-NH-CO-C₆H₁₁ (cyclohexyl) | C₂H₅ | A | 4,5-2.9m(6H); 2.4-1.0m(21H); 1.2d(3H) |
| 430 | 0 | CH₃ | -CH₂-CH₂-NH-CO-C₆H₅ | C₂H₅ | A | 7.6-7.1m(5H); 2.9m(2H); 2.0-1.0m(13H); 1.2d(3H) |

-continued

![Structure: cyclohexyl-CH2-CH(COOH)-N((CH2)n-...)-C(=O)-CH(R1)-N(H)-CH(R2)-COOR3]

| No. | n | R¹ | R² | R³ | Method | NMR |
|---|---|---|---|---|---|---|
| 431 | 0 | CH₃ | CH₂—CH₂—N(H)—CO—(4-Cl-C₆H₄) | C₂H₅ | A | 7.6–7.2m(4H); 2.9m(2H); 2.0–1.0m(13H); 1.2d(3H) |
| 432 | 0 | CH₃ | CH₂—CH₂—N(H)—C(=O)—(4-Cl-C₆H₄) | H | A | 7.6–7.2m(4H); 2.9m(2H); 2.0–1.0m(13H); 1.2d(3H) |
| 433 | 0 | CH₃ | CH₂—CH₂—CH₂—N(C₂H₅)₂ | C₂H₅ | A | 2.6–2.4m(6H); 2.0–1.0m(15H); 1.2d(3H); 1.0t(6H) |
| 434 | 0 | CH₃ | CH₂—CH₂—N(H)—CO—N(H)—C₆H₅ | C₂H₅ | G | 7.4–6.5m(5H); 2.9m(2H); 2.0–1.0m(13H); 1.2d(3H) |
| 435 | 0 | CH₃ | CH₂—CH₂—N(H)—CO—N(H)—(4-Cl-C₆H₄) | C₂H₅ | G | 7.5–6.8m(4H); 2.9m(2H); 2.0–1.0m(13H); 1.2d(3H) |
| 436 | 0 | CH₃ | CH₂—CH₂—N(H)—CO—N(H)—(3-NO₂-C₆H₄) | C₂H₅ | G | 7.8–7.2m(4H); 2.9m(2H); 2.0–1.0m(13H); 1.2d(3H) |
| 437 | 0 | CH₃— | CH₂—CH₂—N(H)—CO—N(H)—CH₃ | C₂H₅ | G | 3.0–2.6m+s(5H); 2.0–1.0m(13H); 1.2d(3H) |
| 438 | 0 | CH₃ | CH₂—CH₂—N(piperidinyl) | C₂H₅ | A | 2.6–2.3m(6H); 2.0–1.0m(19H) 1.2d(3H) |

-continued
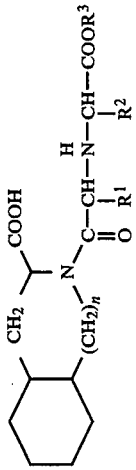
| No. | n | R¹ | R² | R³ | Method | NMR |
|---|---|---|---|---|---|---|
| 439 | 0 | CH₃ |  | C₂H₅ | A | 6.9–6.5m(5H); 2.4m(2H); 2.0–1.0m(13H); 1.2d(3H) |
| 440 | 0 | CH₃ |  | C₂H₅ | A | 6.9–6.5m(4H); 2.4m(2H); 2.0–1.0m(13H); 1.2d(3H) |
| 441 | 0 | CH₃ |  | C₂H₅ | A | 7.0–6.4m(4H); 3.9s(3H); 2.4m(2H); 2.0–1.0m(13H); 1.2d(3H) |
| 442 | 0 | CH₃ | (CH₂)₅—NH₂ | H | C | 2.4m(2H); 2.0–1.0m(19H); 1.2d(3H) |
| 443 | 0 | CH₃ | (CH₂)₄—NH₂ | H | C | 2.4m(2H); 2.0–1.0m(17H); 1.2d(3H) |
| 444 | 1 | CH₃ |  | C₂H₅ | A | 7.4–7.0m(5H); 2.7m(2H); 1.2d(3H) |
| 445 | 1 | CH₃ |  | C₂H₅ | A | 7.3–6.8m(4H); 2.7m(2H); 1.2d(3H) |
| 446 | 1 | CH₃ |  | C₂H₅ | A | 2.4m(2H); 1.2d(3H) |

-continued
| No. | n | R¹ | R² | R³ | Method | NMR |
|---|---|---|---|---|---|---|
| 447 | 1 | (CH₃)₂CH—CH₂ |  3-OCH₃-C₆H₄-CH₂-S- | C₂H₅ | A | 8.1–7.1m(4H); 6.5bs(2H); 2.7m(2H); 1.3d(3H) |
| 448 | 1 |  imidazol-4-yl-CH₂ |  3-CONH₂-C₆H₄-CH₂-S- | C₂H₅ | A | 7.0–6.7m(4H); 3.8s(3H); 2.7m(2H); 2.0–1.0m(15H); 1.0d(6H) |
| 449 | 1 | indol-3-yl-CH₂ | 3-NO₂-C₆H₄-CH₂-S- | C₂H₅ | A | 13.0s(1H); 7.8–6.8m(6H); 6.0bs(2H); 2.9–2.6m(4H) |
| 450 | 1 | indol-3-yl-CH₂ | 3-NH₂-C₆H₄-CH₂-S- | C₂H₅ | A | 8.2–6.4m(10H); 2.9–2.6m(4H) |
| 451 | 1 | (CH₃)₂CH—CH₂ | 2-CH₃-C₆H₄-CH₂-S- | C₂H₅ | A | 7.8–6.4m(10H); 2.9–2.6m(4H) |
| 452 | 1 | CH₃ | —CH₂—S—CH₂—C₆H₅ | C₂H₅ | A | 7.3–7.0m(4H); 2.7m(2H); 2.3s(3H); 2.0–1.0m(15H); 1.0d(6H) |

-continued
| No. | n | R¹ | R² | R³ | Method | NMR |
|---|---|---|---|---|---|---|
| 453 | 1 | CH₂–C₆H₅ | —CH₂—S—CH(CH₃)₂ | C₂H₅ | A | 7.3–7.0m(5H); 3.9–3.0+s(5H); 2.4m(2H); 1.2d(3H) |
| 454 | 1 | CH₃ | —CH₂—S—CH₂—CH₂—N(CH₃)₂ | C₂H₅ | A | 7.1s(5H); 2.6–2.3m(5H); 0.9d(6H) |

| No. | n | R¹ | R² | R³ | Method | NMR |
|---|---|---|---|---|---|---|
| 455 | 1 | $CH_2F$ | $-CH_2-S-CH_2-CH_2-CONH_2$ | $C_2H_5$ | A | 2.6-2.2m+s(12H); 1,2d(3H) |
| 456 | 1 | $CH_3$ | $-CH_2-S-CH_2-CH_2-COOC_2H_5$ | $C_2H_5$ | A | 5.1-4.3m(4H); 2.5-2.2m(6H) |
| 457 | 1 | $CH_3$ | $-CH_2-S-CH_2-CH_2-OC_2H_5$ | $C_2H_5$ | A | 4.2q(4H); 2.5-2.2m(6H); 1.2d+t(9H) |
| 458 | 1 | $CH_3$ | 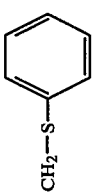 | $C_2H_5$ | A | 3.9-3.0q+m(7H); 2.4-2.2m(4H); 1.2d+t(6H) |
| 459 | 1 | $CH_3$ | 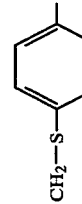 | $C_2H_5$ | A | 7.1s(5H); 2.7m(2H); 2.0-1.0m(14H); 1.2d(3H) |
| 460 | 1 | $CH_3$ | 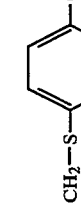 | $C_2H_5$ | A | 7.5-7.0m(4H); 2.7m(2H); 2.0-1.0m(14H); 1.2d(3H) |
| 461 | 1 | $CH_3$ | 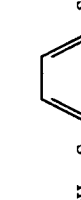 | $C_2H_5$ | A | 7.9-6.9m(4H); 2.7m(2H); 2.1-1.0m(14H); 1.2d(3H) |
| 462 | 1 | $CH_3$ | 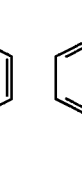 | $C_2H_5$ | A | 8.0-6.9m(4H); 6.5bs(2H); 2.6m(2H); 2.0-1.0m(14H); 1.2d(3H) |
| 463 | 1 | $CH_3$ | 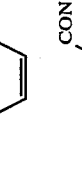 | $C_2H_5$ | A | 6.9-6.4m(4H); 3.8s(3H); 2.7m(2H); 2.1-1.0m(14H); 1.2d(3H) |

-continued

Structure:

$$\text{cyclohexyl-}(CH_2)_n\text{-N}(CH_2-CH(COOH))-C(=O)-CH(R^1)-N(H)-CH(R^2)-COOR^3$$

| No. | n | R¹ | R² | R³ | Method | NMR |
|---|---|---|---|---|---|---|
| 464 | 1 | CH₃ | CH₂—CH₂—S—(3-NO₂-C₆H₄) | C₂H₅ | A | 7.8–6.9m(4H); 6.0bs(2H); 2.6m(2H); 2.0–1.0m(14H); 1.2d(3H) |
| 465 | 1 | H₂N—(CH₂)₄ | CH₂—CH₂—S—(4-CH₃-C₆H₄) | C₂H₅ | B | 8.1–6.9m(4H); 2.7m(2H); 2.0–1.0m(14H); 1.2d(3H) |
| 466 | 1 | CH₃ | CH₂—CH₂—S—CH₂—C₆H₅ | C₂H₅ | A | 7.0–6.8m(4H); 2.7–2.3m+s(7H); 2.0–1.0m(20H) |
| 467 | 1 | CH₃ | CH₂—CH₂—S—CH(CH₃)₂ | C₂H₅ | A | 7.2s(5H); 3.9–3.0m+s(5H); 2.4m(2H); 2.0–1.0m 14H); 1.2d(3H) |
| 468 | 1 | CH₂-(indol-3-yl) | CH₂—CH₂—S—CH₂—CH₂—N(CH₃)₂ | C₂H₅ | A | 2.6–2.3m(3H); 2.1–1.0m(14H); 1.2d(3H); 1.0d(6H) |
| 469 | 1 | CH₃ | CH₂—CH₂—S—CH₂—CH₂—CONH₂ | C₂H₅ | A | 7.8–6.5m(6H); 2.8–2.3m(14H); 2.0–1.0m(14H) |
| 470 | 1 | CH₃ | CH₂—S(=O)—C₆H₅ | C₂H₅ | D | 6.0bs(2H); 2.5–2.2m(6H); 2.0–1.0m(14H); 1.2d(3H) |
| 471 | 1 | CH₃ | CH₂—S(=O)—(4-F-C₆H₄) | C₂H₅ | D | 7.5–7.0m(5H); 2.6m(2H); 1.2d(3H) |

-continued

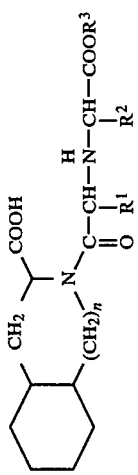

| No. | n | R¹ | R² | R³ | Method | NMR |
|---|---|---|---|---|---|---|
| 472 | 1 | CH₃ | −CH₂−S(=O)−C₆H₅ | C₂H₅ | D | 7.4-6.9m(4H); 2.6m(2H); 1.2d(3H) |
| 473 | 1 | CH₃ | −CH₂−S(=O)−CH(CH₃)₂ | C₂H₅ | D | 7.1s(5H); 4.1s(2H); 2.6m(2H); 1.2d(3H) |
| 474 | 1 | CH₃ | −CH₂−CH₂−S(=O)−C₆H₄−Cl (p) | C₂H₅ | D | 2.8-2.5m(3H); 1.2d(3H); 1.0d(6H) |
| 475 | 1 | CH₃ | −CH₂−CH₂−S(=O)−C₆H₄−CH₃ (p) | C₂H₅ | D | 7.4-7.0m(5H); 2.6m(2H); 2.0-1.0m(14H); 1.2d(3H) |
| 476 | 1 | CH₃ | −CH₂−CH₂−S(=O)−C₆H₅ | C₂H₅ | D | 7.5-6.9m(4H); 2.6m(2H); 2.0-1.0m(14H); 1.2d(3H) |
| 477 | 1 | CH₃ | −CH₂−CH₂−S(=O)−CH₂−C₆H₅ | C₂H₅ | D | 7.6-6.9m(4H); 2.6m(2H); 2.3s(3H); 2.0-1.0m(14H); 1.2d(3H) |
| 478 | 1 | CH₃ | −CH₂−CH₂−S(=O)−CH(CH₃)₂ | C₂H₅ | D | 7.1s(5H); 4.1s(2H); 2.7m(2H); 2.0-1.0m(14H)1.2d(3H) |
| 479 | 1 | CH₃ | −CH₂−CH₂−S(=O)−CH₂−CH₂−N(CH₃)₂ | C₂H₅ | D | 2.8-2.5m(3H); 2.0-1.0m(14H); 1.2d(3H); 0.9d(6H) |

-continued

[Structure: cyclohexyl-CH₂-CH(COOH)-N((CH₂)ₙ-)-C(=O)-CH(R¹)-NH-CH(R²)-COOR³]

| No. | n | R¹ | R² | R³ | Method | NMR |
|---|---|---|---|---|---|---|
| 480 | 1 | CH₂ | phenyl-SO₂-CH₂- | C₂H₅ | E | 2.8-2.2m+s(12H); 2.0 1.0m(14H); 1.2d(3H) |
| 481 | 1 | CH₃ | 4-F-phenyl-SO₂-CH₂- | C₂H₅ | E | 7.8-7.1m(5H); 2.8m(2H); 1.2d(3H) |
| 482 | 1 | CH₃ | phenyl-CH₂-SO₂- | C₂H₅ | E | 7.7-6.9m(4H); 2.8m(2H); 1.2d(3H) |
| 483 | 1 | CH₃ | (CH₃)₂CH-SO₂-CH₂- | C₂H₅ | E | 7.2s(5H); 5.1-4.3m(4H); 2.8m(2H); 1.2d(3H) |
| 484 | 1 | CH₃ | phenyl-SO₂-CH₂- | C₂H₅ | E | 3.0-2.7m(3H); 1.2d+t(9H) |
| 485 | 1 | CH₃ | 4-Cl-phenyl-SO₂-CH₂- | C₂H₅ | E | 7.7-7.2m(5H); 2.8m(2H); 2.0-1.0m(14H); 1.2d(3H) |
| 486 | 1 | CH₃ | 4-CH₃-phenyl-SO₂-CH₂-CH₂- | C₂H₅ | E | 8.0-7.1m(4H); 2.8m(2H); 2.0-1.0m(14H); 1.2d(3H) |

-continued

Structure:

$$\text{cyclohexyl-CH}_2\text{-CH(COOH)-N((CH}_2\text{)}_n\text{-C(=O)-CH(R}^1\text{)-NH-CH(R}^2\text{)-COOR}^3\text{)}$$

| No. | n | R$^1$ | R$^2$ | R$^3$ | Method | NMR |
|-----|---|-------|-------|-------|--------|-----|
| 487 | 1 | CH$_3$ | -CH$_2$-CH$_2$-S(=O)$_2$-C$_6$H$_5$ | C$_2$H$_5$ | E | 7.6-6.9m(4H); 2.8m(2H); 2.3s(3H); 2.0-1.0m(14H); 1.2d(3H) |
| 488 | 1 | CH$_3$ | -CH$_2$-CH$_2$-S(=O)$_2$-CH(CH$_3$)$_2$ | C$_2$H$_5$ | E | 7.1s(5H); 4.2s(2H); 2.8m(2H); 2.0-1.0m(14H); 1.2d(3H) |
| 489 | 1 | CH$_3$ | -CH$_2$-CH$_2$-S(=O)$_2$-CH$_2$-CH$_2$-N(CH$_3$)$_2$ | C$_2$H$_5$ | E | 3.0-2.7m(3H); 2.0-1.0m(14H); 1.1d+t(9H) |
| 490 | 0 | CH$_3$ | -CH$_2$-S-C$_6$H$_5$ | C$_2$H$_5$ | A | 3.0-2.2m+s(12H); 2.0-1.0m(14H); 1.2d(3H) |
| 491 | 0 | CH$_3$ | -CH$_2$-S-(4-Cl-C$_6$H$_4$) | C$_2$H$_5$ | A | 6.9s(5H); 2.5m(2H); 1.2d(3H) |
| 492 | 0 | CH$_3$ | -CH$_2$-S-(2-CH$_3$-C$_6$H$_4$) | C$_2$H$_5$ | A | 7.4-6.8m(4H); 2.5m(2H); 1.2d(3H) |
| 493 | 0 | CH$_3$ | -CH$_2$-S-CH$_2$-C$_6$H$_5$ | C$_2$H$_5$ | A | 7.5-6.8m(4H); 2.5m(2H); 2.3s(3H); 1.2d(3H) |
| 494 | 0 | CH$_3$ | -CH$_2$-S-CH-(CH$_3$)$_2$ | C$_2$H$_5$ | A | 7.2s(5H); 3.7-3.0m+s(5H); 2.4m(2H); 1.2d(3H) |

-continued

[Structure: cyclohexane with CH2 and (CH2)n substituents, bearing N connected to CH(COOH) and C(=O)-CH(R1)-NH-CH(R2)-COOR3]

| No. | n | R¹ | R² | R³ | Method | NMR |
|---|---|---|---|---|---|---|
| 495 | 0 | CH₃ | —CH₂—CH₂—S—C₆H₅ | C₂H₅ | A | 2.7–2.3m(3H); 1.2d(3H); 0.9d(6H) |
| 496 | 1 | CH₃ | 4-Cl-C₆H₄-CH₂ | C₂H₅ | B | 7.6–7.0m(4H); 3.9–2.9m(5H); 1.2d(3H) |
| 497 | 1 | CH₃ | 3,4-Cl₂-C₆H₃-CH₂ | H | B | 7.8–7.0m(3H); 3.9–2.9m(5H); 1.2d(3H) |
| 498 | 1 | CH₃ | 4-NO₂-C₆H₄-CH₂ | H | B | 8.3–7.0m(4H); 3.9–2.9m(5H); 1.2d(3H) |
| 499 | 1 | CH₃ | 4-CH₃-C₆H₄-CH₂ | C₂H₅ | B | 7.4–7.0m(4H); 3.9–2.9m(5H); 2.3s(3H); 1.2d(3H) |
| 500 | 1 | CH₃ | cycloheptenyl-CH₃ | H | A | 5.3m(1H); 2.3m(4H); 2.0–1.0m(18H); 1.2d(3H) |

-continued

Structure:
CH₂-COOH on N, with (CH₂)ₙ-cyclohexane group; N-C(=O)-CH(R¹)-N(H)-CH(R²)-COOR³

| No. | n | R¹ | R² | R³ | Method | NMR |
|---|---|---|---|---|---|---|
| 501 | 1 | CH₃ | cyclohexenyl-CH₂- | H | A | 5.4m(1H); 2.3m(4H); 2.0–1.0m(16H); 1.2d(3H) |
| 502 | 1 | CH₃ | (thiopyranyl)-CH₂- | H | A | 5.5m(1H); 3.9–3.0m(5H); 2.5–1.0m(16H); 1.2d(3H) |
| 503 | 1 | CH₃ | (dithianyl)-CH₂- | H | A | 5.9m(1H); 3.9–3.0m(7H); 1.2d(3H) |
| 504 | 1 | CH₃ | CH₃-C(=N-NH(CH₂)₃-)-C(CH₃)=N- | C₂H₅ | A | 7.4s(1H); 2.5m(2H); 2.3s(6H); 2.0–1.0m(16H) |
| 505 | 1 | CH₃ | benzimidazolyl-CH₂CH₂- | C₂H₅ | A | 7.5–6.8m(4H); 2.8m(2H); 2.0–1.0m(14H); |
| 506 | 1 | CH₃ | benzimidazolyl-CH₂-CH₂- | H | A | 7.5–6.8m(4H); 2.8m(2H); 2.0–1.0m(14H) |
| 507 | 0 | CH₃ | —CH₂—CH₂—S—C₆H₄—Cl | C₂H₅ | A | 7.0s(5H); 2.7m(2H); 2.0–1.0m(13H); 1.2d(3H) |

-continued

Structure:
$$\text{cyclohexyl-CH}_2\text{-CH(COOH)-N((CH}_2)_n\text{)-C(=O)-CH(R}^1)\text{-NH-CH(R}^2)\text{-COOR}^3$$

| No. | n | R¹ | R² | R³ | Method | NMR |
|---|---|---|---|---|---|---|
| 508 | 0 | CH₃ | CH₂—CH₂—S—(4-CH₃-C₆H₄) | C₂H₅ | A | 7.5-6.5m(4H); 2.7m(2H); 2.0-1.0m(13H); 1.2d(3H) |
| 509 | 0 | CH₃ | CH₂—CH₂—S—CH₂—C₆H₅ | C₂H₅ | A | 7.3-6.5m(4H); 2.7-2.3m+s(5H); 2.0-1.0m(13H); 1.2d(3H) |
| 510 | 0 | CH₃ | CH₂—CH₂—S—CH(CH₃)₂ | C₂H₅ | A | 4.5-3.0m+s(5H); 2.4m(2H); 2.0-1.0m(13H); 1.2d(3H) |
| 511 | 0 | CH₃ | CH₂—S(=O)—C₆H₅ | C₂H₅ | D | 2.6-2.3m(3H); 2.0-1.0m(13H); 1.2d(3H); 1.0d(6H) |
| 512 | 0 | CH₃ | CH₂—S(=O)—(4-Cl-C₆H₄) | C₂H₅ | D | 7.5-7.0m(5H); 2.6m(2H); 1.2d(3H) |
| 513 | 0 | CH₃ | —CH₂—S(=O)—CH₂—C₆H₅ | C₂H₅ | D | 7.4-7.0m(4H); 2.6m(2H); 1.2d(3H) |
| 514 | 0 | CH₃ | —CH₂—S(=O)—CH(CH₃)₂ | C₂H₅ | D | 7.1s(5H); 4.1s(2H); 2.6m(2H); 1.2d(3H) |
| 515 | 0 | CH₃ | —CH₂—CH₂—S(=O)—C₆H₅ | C₂H₅ | D | 2.8-2.5m(3H); 1.2d(3H); 1.0d(6h) |

-continued

| No. | n | R¹ | R² | R³ | Method | NMR |
|---|---|---|---|---|---|---|
| 516 | 0 | CH₃ | —CH₂—CH₂—S(O₂)—C₆H₄—Cl | C₂H₅ | D | 7.4-7.0m(5H); 2.6m(2H); 2.0-1.0m(13H); 1.2d(3H) |
| 517 | 0 | CH₃ | —CH₂—CH₂—S(O₂)—C₆H₄—CH₃ | C₂H₅ | D | 7.5-7.0m(4H); 2.6m(2H); 2.0-1.0m(13H); 1.2d(3H) |
| 518 | 0 | CH₃ | —CH₂—CH₂—S(O₂)—C₆H₅ | C₂H₅ | D | 7.6-7.0m(4H); 2.6m(2H); 2.3s(3H); 2.1-1.0m(13H); 1.2d(3H) |
| 519 | 0 | CH₃ | —CH₂—CH₂—S(O₂)—CH(CH₃)₂ | C₂H₅ | D | 7.1s(5H); 4.1s(2H); 2.7m(2H); 2.1-1.0m(13H); 1.2d(3H) |
| 520 | 0 | CH₃ | —CH₂—S(O₂)—C₆H₅ | C₂H₅ | E | 2.8-2.5m(3H); 2.0-1.0m(13H); 1.2d(3H); 1.1d(6H) |
| 521 | 0 | CH₃ | —CH₂—S(O₂)—C₆H₄—Cl | C₂H₅ | E | 7.8-7.3m(5H); 2.8m(2H); 1.2d(3H) |
| 522 | 0 | CH₃ | —CH₂—S(O₂)—CH₂—C₆H₅ | C₂H₅ | E | 7.7-7.2m(4H); 2.8m(2H); 1.2d(3H) |
| 523 | 0 | CH₃ | —CH₂—S(O₂)—CH(CH₃)₂ | C₂H₅ | E | 7.1s(5H); 4.3s(2H); 2.8m(2H); 1.2d(3H) |

-continued

Structure:

CH₂—COOH on N, with (CH₂)ₙ—cyclohexyl group; N—C(=O)—CH(R¹)—NH—CH(R²)—COOR³

| No. | n | R¹ | R² | R³ | Method | NMR |
|-----|---|-----|----|-----|--------|-----|
| 524 | 0 | CH₃ | —CH₂—CH₂—S(=O)₂—C₆H₅ | C₂H₅ | E | 3.0–2.7m(3H); 1.2d+t(9H) |
| 525 | 0 | CH₃ | —CH₂—CH₂—S(=O)₂—C₆H₄—Cl (4-Cl) | C₂H₅ | E | 7.7–7.2m(5H); 2.8m(2H); 2.0–1.0m(13H); 1.2d(3H) |
| 526 | 0 | CH₃ | —CH₂—CH₂—S(=O)₂—C₆H₄—CH₃ (4-CH₃) | C₂H₅ | E | 8.0–7.3m(4H); 2.8m(2H); 2.0–1.0m(13H); 1.2d(3H) |
| 527 | 0 | CH₃ | —CH₂—CH₂—S(=O)₂—CH₂—C₆H₅ | C₂H₅ | E | 7.1s(5H); 4.2s(2H); 2.8m(2H); 2.1–1.0m(13H) |
| 528 | 0 | CH₃ | —CH₂—CH₂—S(=O)₂—CH(CH₃)₂ | C₂H₅ | E | 3.0–2.7m(3H); 2.0–1.0m(13H); 1.1d+t(9H) |
| 529 | 1 | CH₃ | —CH₂—OH | C₂H₅ | A | 3.9–3.0m(5H); 1.2d(3H) |
| 530 | 1 | CH₃ | —CH₂—O—C₆H₅ | C₂H₅ | H | 7.0s(5H); 3.9–3.0m(5H); 1.2d(3H) |
| 531 | 1 | CH₃ | —CH₂—O—C₆H₄—CH₃ (4-CH₃) | C₂H₅ | H | 7.3–6.6m(4H); 3.9–3.0m(5H); 2.3s(3H); 1.2d(3H) |

-continued

Structure:

$$\text{cyclohexane-CH}_2\text{-CH(COOH)-N(-(CH}_2)_n\text{-R}^2)\text{-C(=O)-CH(R}^1)\text{-NH-CH(R}^2)\text{-COOR}^3$$

| No. | n | R¹ | R² | R³ | Method | NMR |
|---|---|---|---|---|---|---|
| 532 | 1 | CH₃ | −CH₂−O−(4-Cl-C₆H₄) | C₂H₅ | H | 7.3−6.7m(4H); 3.9−3.0m(5H); 1.2d(3H) |
| 533 | 1 | H₂N−(CH₂)₄ | −CH₂−O−(3-OCH₃-C₆H₄) | C₂H₅ | B | 6.8−6.3m(4H); 3.9−3.0m+s(8H); 2.4m(2H); 2.0−1.0m(18H) |
| 534 | 1 | H₂N−(CH₂)₃ | −CH₂−O−(4-NO₂-C₆H₄) | C₂H₅ | B | 8.2−6.8m(4H); 3.9−3.0m(5H); 2.4m(2H); 2.0−1.0m(16H) |
| 535 | 1 | (CH₃)₂−CH−CH₂− | −CH₂−O−(4-COOC₂H₅-C₆H₄) | C₂H₅ | A | 7.6−6.8m(4H); 4.2q(4H); 3.9−3.0m(5H); 2.0−1.0m(15H); 1.2t(6H); 1.0d(6H) |
| 536 | 1 | CH₃ | −CH₂−O−(2-CH₃-4-Cl-C₆H₃) | C₂H₅ | A | 7.2−6.8m(3H); 3.9−3.0m(5H); 2.3s(3H); 1.2d(3H) |
| 537 | 1 | CH₃ | −CH₂−O−CH₂−C₆H₅ | C₂H₅ | A | 7.0s(5H); 4.0s(2H); 3.9−3.0m(5H); 1.3d(3H) |
| 538 | 1 | CH₃ | −CH₂−O−CH₂−(4-Cl-C₆H₄) | C₂H₅ | A | 7.4−6.9m(4H); 4.0s(2H) 3.9−3.0m(5H); 1.2d(3H) |

-continued

Structure:

$$\text{R}^2\text{—CH}_2\text{—CH(COOH)—N((CH}_2)_n\text{-cyclohexyl-cyclohexyl)—C(=O)—CH(R}^1\text{)—NH—CH(R}^2\text{)—COOR}^3$$

| No. | n | R¹ | R² | R³ | Method | NMR |
|---|---|---|---|---|---|---|
| 539 | 1 | H₂N—(CH₂)₄ | CH₃ (o-tolyl with CH₂—O—CH₂) | C₂H₅ | B | 7.4–7.0m(4H); 4.0s(2H); 3.9–3.0m(5H); 2.5–2.2d+t(5H); 2.0–1.0m(18H) |
| 540 | 1 | indol-3-yl-CH₂ | 3-OCH₃-phenyl-CH₂—O—CH₂ | C₂H₅ | A | 7.8–6.4m(10H); 4.0s(2H); 3.8s(3H); 3.9–3.0m(5H); 2.7m(2H) |
| 541 | 1 | H | 4-CONH₂-phenyl-CH₂—O—CH₂ | C₂H₅ | A | 7.8–7.0m(4H); 6.0bs(2H); 4.0s(2H); 3.9–3.0m(6H) |
| 542 | 1 | HS—CH₂ | 3-NO₂-phenyl-CH₂—O—CH₂ | C₂H₅ | B | 8.2–7.0m(4H); 4.0s(2H); 3.9–3.0m(5H); 2.3m(2H) |
| 543 | 1 | HS—CH₂ | 3-NH₂-phenyl-CH₂—O—CH₂ | C₂H₅ | B | 7.2–6.4m(4H); 4.0s(2H); 3.9–3.0m(5H); 2.3m(2H) |
| 544 | 1 | CH₃ | CH₂—O—CH(CH₃)₂ | C₂H₅ | H | 3.9–3.0m(6H); 1.2d(3H); 0.9d(6H); |
| 545 | 1 | CH₃ | CH₂—O—CH₂—CH₂—N(CH₃)₂ | C₂H₅ | A | 3.9–3.0m(7H); 2.4–2.1m+s(8H); 1.2d(3H) |
| 546 | 1 | CH₃ | —CH₂—O—C(=O)—NH—phenyl | C₂H₅ | A | 7.6–6.9m(5H); 4.0m(2H); 1.2d(3H) |

-continued structure: cyclohexane-CH2-CH(COOH)-N((CH2)n-)-C(=O)-CH(R1)-NH-CH(R2)-COOR3

| No. | n | R² | R¹ | R³ | Method | NMR |
|---|---|---|---|---|---|---|
| 547 | 1 | CH₂—COOH | CH₃ | H | A | 2.1-1.0m(14H); 1.2d(3H) |
| 548 | 1 | CH₂—CONH₂ | CH₃ | H | A | 6.5bs(2H); 2.1-1.0m(14H); 1.2d(3H) |
| 549 | 1 | CH₂—CON(CH₃)₂ | CH₃ | H | A | 3.9-3.0m+2s(9H); 2.1-1.0m(14H); 1.2d(3H) |
| 550 | 1 | CH₂-(indol-3-yl)-CH₂—CONH—Ph | CH₃ | H | A | 7.8-6.4m(11H); 2.8-1.0m(16H) |
| 551 | 1 | CH₂—CONH—(3-CH₃-C₆H₄) | CH₃ | H | A | 7.3-6.9m(4H); 2.3s(3H); 2.2-1.0m(14H); 1.2d(3H) |
| 552 | 1 | CH₂—CONH—(4-Cl-C₆H₄) | CH₃ | H | F | 7.7-6.9m(4H); 2.3m(2H); 1.2d(3H) |
| 553 | 1 | CH₂—CONH—(4-OCH₃-C₆H₄) | CH₂-(imidazol-4-yl) | H | F | 13.0s(1H); 7.5-6.3m(6H); 3.9s(3H); 2.7m(2H); 2.1-1.0m(14H) |
| 554 | 1 | CH₂—CONH—(4-COOH-C₆H₄) | CH₃ | H | F | 7.7-6.6m(4H); 2.1-1.0m(14H); 1.2d(3H) |

-continued

Structure:

CH₂—[cyclohexyl]—(CH₂)ₙ—N(—CH—COOH / CH₂—)—C(=O)—CH(R¹)—N(H)—CH(R²)—COOR³

| No. | n | R¹ | R² | R³ | Method | NMR |
|---|---|---|---|---|---|---|
| 555 | 1 | CH₃ | CH₂—CO—NH—C₆H₄—CONH₂ | H | F | 7.7–6.6m(4H); 2.1–1.0m(14H); 1.2d(3H) |
| 556 | 1 | CH₃ | CH₂—CO—NH—C₆H₄—COOC₂H₅ | H | F | 7.7–6.6m(4H); 4.2q(2H); 2.1–1.0m(14H); 1.2d+t(6H) |
| 557 | 1 | CH₃ | CH₂—CO—NH—C₆H₄—OC₂H₅ | H | F | 7.3–6.4m(4H); 3.5q(2H); 2.1–1.0m(14H); 1.2d+t(6H) |
| 558 | 1 | CH₃ | CH₂—CO—NH—C₆H₃(Cl)(OCH₃) | H | F | 7.2–6.4m(3H); 3.9s(3H); 2.1–1.0m(14H); 1.2d(3H) |
| 559 | 1 | CH₃ | CH₂—CO—NH—C₆H₃(OCH₃)₂ | H | F | 7.1–6.3m(3H); 3.8s(6H); 2.1–1.0m(14H); 1.2d(3H) |
| 560 | 1 | CH₃ | CH₂—CO—NH—C₆H₂(OCH₃)₃ | H | F | 7.0–6.2m(2H); 3.9s(9H); 2.1–1.0m(14H); 1.2d(3H) |
| 561 | 1 | CH₃ | CH₂—COOC₂H₅ | H | F | 4.2q(2H); 2.0–1.0m(14H); 1.2d+t(6H) |

Structure:

$$\text{cyclohexyl-CH}_2\text{-CH(COOH)-N((CH}_2)_n\text{-...)-C(=O)-C(R}^1\text{)(R}^2\text{)-NH-CH(R}^2\text{)-COOR}^3$$

| No. | n | R¹ | R² | R³ | Method | NMR |
|---|---|---|---|---|---|---|
| 562 | 1 | CH₃ | CH₂—CO—O—CH(CH₃)₂ | H | F | 4.8septett(1H); 2.1–1.0m(14H); 1.2d(3H); 0.9d(6H) |
| 563 | 1 | CH₃ | CH₂—CO—O—CH₂—(C₆H₅) | H | F | 7.2s(5H); 5.3s(2H); 2.1–1.0m(14H); 1.2d(3H) |
| 564 | 1 | CH₃ | CH₂—CH₂—COOH | C₂H₅ | A | 2.1–1.0m(16H); 1.2d(3H) |
| 565 | 1 | CH₃ | CH₂—CH₂—CONH₂ | C₂H₅ | A | 2.1–1.0m(16H); 1.2d(3H) |
| 566 | 1 | CH₃ | CH₂—CH₂—CON(CH₃)₂ | C₂H₅ | A | 3.02s(6H); 2.0–1.0m(14H) 1.2d(3H) |
| 567 | 1 | CH₃ | CH₂—CH₂—CONH—CH₂—(C₆H₅) | C₂H₅ | A | 7.1s(5H); 2.1–1.0m(16H) 1.2d(3H) |
| 568 | 1 | CH₃ | CH₂—CH₂—CON(H)—(C₆H₅) | C₂H₅ | A | 7.3–6.9m(4H); 2.1–1.0m(16H); 1.2d(3H) |
| 569 | 1 | H₂N—(CH₂)₄— | CH₂—CH₂—CON(H)—(4-F-C₆H₄) | C₂H₅ | B | 7.3–6.8m(4H); 2.4–2.1m(4H); 2.0–1.0m(20H) |
| 570 | 1 | CH₃ | CH₂—CH₂—CON(H)—(4-CH₃-C₆H₄) | C₂H₅ | A | 7.2–6.4m(4H); 3.9s(3H); 2.1–1.0m(16H); 1.2d(3H) |
| 571 | 1 | CH₃ | CH₂—CH₂—CONH—(3-OH-C₆H₄) | H | A | 7.3–6.3m(4H); 2.1–1.0m(16H); 1.2d(3H) |

-continued

Structure:

$$\text{cyclohexyl-CH}_2\text{-CH(COOH)-N(-(CH}_2)_n\text{-)-C(=O)-CH(R}^1\text{)-NH-CH(R}^2\text{)-COOR}^3$$

| No. | n | R¹ | R² | R³ | Method | NMR |
|-----|---|-----|-----|-----|--------|-----|
| 572 | 1 | CH₃ | CH₂—CH₂—CON(H)—(2-OCH₃, 5-Cl-phenyl) | H | A | 7.2–6.4m(3H); 3.9s(3H); 2.1–1.0m(16H); 1.2d(3H) |
| 573 | 1 | CH₃ | CH₂—CH₂—C(=O)—N(H)—(4-CONH₂-phenyl) | H | A | 7.7–7.0m(4H); 2.1–1.0m(16H); 1.2d(3H) |
| 574 | 1 | CH₃ | CH₂—CH₂—C(=O)—N(H)—(4-COOC₂H₅-phenyl) | H | A | 7.6–7.0m(4H); 4.2q(2H); 2.1–1.0m(16H); 1.2d+t(6H) |
| 575 | 1 | CH₃ | CH₂—CH₂—C(=O)—N(H)—(4-OC₂H₅-phenyl) | H | A | 7.3–6.4m(4H); 3.9–3.0m+q(5H); 2.1–1.0m(16H); 1.2d+t(6H) |
| 576 | 1 | CH₃ | CH₂—CH₂—CON(H)—(3-NO₂-phenyl) | H | A | 8.2–6.9m(4H); 2.1–1.0m(16H); 1.2d(3H) |
| 577 | 1 | CH₃ | CH₂—CH₂—CON(H)—(3,4-diOCH₃-phenyl) | C₂H₅ | A | 7.1–6.3m(3H); 3.8s(6H); 2.1–1.0m(16H); 1.2d(3H) |

-continued

| No. | n | R¹ | R² | R³ | Method | NMR |
|---|---|---|---|---|---|---|
| 578 | 1 | CH₃ | -CH₂-CH₂-CON(H)- (3,4,5-trimethoxyphenyl) | C₂H₅ | A | 7.0–6.2m(2H); 3.9s(9H); 2.1–1.0m(16H); 1.2d(3H) |
| 579 | 1 | CH₃ | -CH₂-CH₂-CON(H)-CH(CH₃)₂ | H | A | 2.8–2.2m(3H); 2.0–1.0m(14H); 1.2d(3H); 1.0d(6H) |
| 580 | 1 | CH₃ | -CH₂-CH₂-CON(H)-CH₂-phenyl | H | A | 7.2s(5H); 5.1–4.3m(4H); 2.1–1.0m(16H); 1.2d(3H) |
| 581 | 1 | CH₃ | -CH₂-CH₂-CON(H)-CH₂-(3,4-dimethoxyphenyl) | C₂H₅ | A | 7.1–6.3m(3H); 3.9s(6H); 2.9–1.0m(20H); 1.2d(3H) |
| 582 | 0 | CH₃ | -CH₂-OH | C₂H₅ | A | 4.5–3.0m(5H); 1.2d(3H) |
| 583 | 0 | CH₃ | -CH₂-O-phenyl | C₂H₅ | A | 6.9s(5H); 4.5–3.0m(5H); 1.2d(3H) |
| 584 | 0 | CH₃ | -CH₂-O-CH₂-phenyl | C₂H₅ | A | 7.2s(5H); 4.0s(2H); 4.5–3.0m(5H); 1.2d(3H) |
| 585 | 0 | CH₃ | -CH₂-O-CH₂-(4-chlorophenyl) | C₂H₅ | A | 7.4–6.5m(4H); 4.0s(2H); 4.5–3.0m(5H); 1.2d(3H) |

-continued $$\text{cyclohexyl-}(CH_2)_n\text{-N}(CH_2COOH)\text{-C(=O)-CH}(R^1)\text{-NH-CH}(R^2)\text{-COOR}^3$$

| No. | n | R¹ | R² | R³ | Method | NMR |
|---|---|---|---|---|---|---|
| 586 | 0 | CH₃ | CH₂—O—CH(CH₃)₂ | C₂H₅ | A | 4.5-3.0m(6H); 1.2d(3H); 0.9d(6H) |
| 587 | 0 | CH₃ | CH₂—O—CH₂—CH₂—N(CH₃)₂ | C₂H₅ | A | 4.5-3.0m(7H); 2.4-2.1m+s(8H); 1.2d(3H) |
| 588 | 0 | CH₃ | —CH₂—O—C(=O)—NH—C₆H₅ | C₂H₅ | A | 7.3s(5H); 4.5-3.0m(5H) 1.2d(3H) |
| 589 | 0 | CH₃ | CH₂—COOH | H | A | 2.1-1.0m(13H); 1.2d(3H) |
| 590 | 0 | CH₃ | CH₂—CONH₂ | H | F | 6.5s(2H); 2.1-1.0m(13H) 1.2d(3H) |
| 591 | 0 | CH₃ | CH₂—CON(CH₃)₂ | H | F | 4.5-3.0m+2s(9H); 2.1-1.0m(13H); 1.2d(3H) |
| 592 | 0 | CH₃ | CH₂—C(=O)NH—C₆H₅ | H | F | 7.0s(5H); 2.1-1.0m(13H); 1.2d(3H) |
| 593 | 0 | CH₃ | CH₂—C(=O)NH—(3-CH₃-C₆H₄) | H | F | 7.3-6.5m(4H); 2.3s(3H); 2.2-1.0m(13H); 1.2d(3H) |
| 594 | 0 | CH₃ | CH₂—C(=O)NH—(4-Cl-C₆H₄) | H | F | 7.7-6.5m(4H); 2.3m(2H); 1.2d(3H) |
| 595 | 0 | CH₃ | CH₂—COOC₂H₅ | H | F | 4.2q(2H); 2.0-1.0m(13H) 1.2d+t(6H) |
| 596 | 0 | CH₃ | CH₂—CH₂—COOH | C₂H₅ | A | 2.1-1.0m(15H); 1.2d(3H) |
| 597 | 0 | CH₃ | CH₂—CH₂—CONH₂ | C₂H₅ | A | 2.1-1.0m(15H); 1.2d(3H) |
| 598 | 0 | CH₃ | CH₂—CH₂—CON(CH₃)₂ | C₂H₅ | A | 3.02s(6H); 2.0-1.0m(13H); 1.2d(3H) |

-continued
| No. | n | R¹ | R² | R³ | Method | NMR |
|---|---|---|---|---|---|---|
| 599 | 0 | $CH_3$ |  | $C_2H_5$ | A | 7.0s(5H); 2.1–1.0m(15H); 1.2d(3H) |
| 600 | 0 | $CH_3$ | 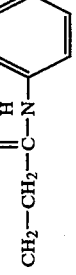 | H | A | 7.3–6.8m(4H); 2.1–1.0m(15H); 1.2d(3H) |
| 601 | 0 | $CH_3$ |  | $C_2H_5$ | A | 7.3–6.4m(4H); 3.6q(2H); 2.1–1.0m(15H); 1.2d+t(6H) |
| 602 | 0 | $CH_3$ | $CH_2-CH_2-CON-CH(CH_3)_2$ with H on N | $C_2H_5$ | A | 2.8–2.2m(3H); 2.0–1.0m(13H); 1.2d(3H); 1.0d(6H) |
| 603 | 0 | $CH_3$ |  | $C_2H_5$ | A | 7.0s(5H); 5.1–4.3m+s(5H); 2.1–1.0m(15H); 1.2d(3H) |
| 604 | 0 | $CH_3$ |  | $C_2H_5$ | A | 7.0–6.2m(3H); 3.9s(6H); 2.9–1.0m(19H); 1.2d(3H) |
| 605 | 1 | $CH_3$ | 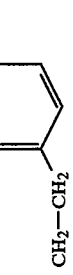 | $C_2H_5$ | B | 7.2s(5H); 2.6m(2H); 2.0–1.0m(14H); 1.2d(3H) |

-continued
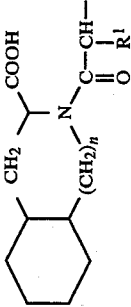
| No. | n | R¹ | R² | R³ | Method | NMR |
|---|---|---|---|---|---|---|
| 606 | 1 | CH₃ | 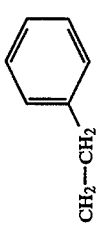 | H | B | 7.2s(5H); 2.6m(2H); 2.0–1.0m(14H); 1.2d(3H) |
| 607 | 1 | CH₃ | 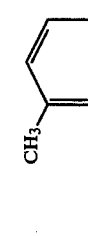 | C₂H₅ | B | 7.4–7.0m(4H); 2.6m(2H); 2.3s(3H); 2.0–1.0m(14H); 1.2d(3H) |
| 608 | 1 | HO—CH₂ | 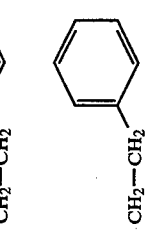 | C₂H₅ | B | 7.2s(5H); 2.8–2.5m(4H); 2.0–1.0m(14H) |
| 609 | 1 | H₂N—(CH₂)₄— | 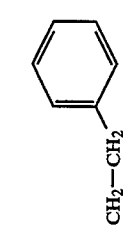 | H | B | 7.2s(5H); 2.8–2.3m(4H); 2.0–1.0m(20H) |
| 610 | 1 | H₂N(CH₂)₃— | 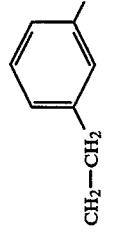 | H | B | 8.2–7.1m(4H); 2.8–2.3m(4H); 2.0–1.0m(18H) |
| 611 | 1 | CH₃ | 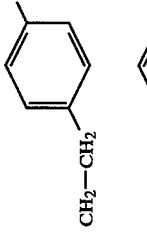 | C₂H₅ | B | 7.5–6.9m(4H); 2.7m(2H); 2.0–1.0m(14H); 1.2d(3H) |
| 612 | 1 | CH₃ | (4-Cl-C₆H₄)CH₂—CH₂ | H | B | 7.5–6.9m(4H); 2.7m(2H); 2.0–1.0m(14H); 1.2d(3H) |

-continued

[Structure: CH₂(cyclohexyl)—CH(COOH)—N((CH₂)ₙ)—C(=O)—CH(R¹)—NH—CH(R²)—COOR³]

| No. | n | R¹ | R² | R³ | Method | NMR |
|---|---|---|---|---|---|---|
| 613 | 1 | CH₃ | 4-COOH-C₆H₄-CH₂-CH₂- | H | B | 7.8–7.1m(4H); 2.7m(2H); 2.0–1.0m(14H); 1.2d(3H) |
| 614 | 1 | HN=C(NH₂)—NH—(CH₂)₄— | 4-Cl-C₆H₄-CH₂-CH₂- | C₂H₅ | B | 7.5–7.0m(4H); 2.8–2.6m(4H); 2.0–1.0m(20H) |
| 615 | 1 | H₂N—(CH₂)₂— | 4-OH-C₆H₄-CH₂-CH₂- | H | B | 7.2–6.5m(4H); 2.8–2.3m(4H); 2.0–1.0m(16H) |
| 616 | 1 | H₂N—(CH₂)₅— | C₆H₅-CH₂-CH₂- | H | B | 7.2bs(5H); 2.7–2.3m(4H); 2.0–1.0m(22H) |
| 617 | 1 | H₂N—(CH₂)₄— | 4-CONH₂-C₆H₄-CH₂-CH₂- | H | B | 7.8–7.1m(4H); 2.7–2.3m(4H); 2.0–1.0m(20H) |
| 618 | 1 | H₂N—CH₂— | C₆H₅-CH₂-CH₂- | H | B | 7.2bs(5H); 2.7–2.3m(4H); 2.0–1.0m(14H) |
| 619 | 1 | CH₃ | 4-F-C₆H₄-CH₂-CH₂- | C₂H₅ | B | 7.2–6.8m(4H); 2.7m(2H); 2.0–1.0m(14H); 1.2d(3H) |

-continued

Structure:

cyclohexane-CH₂-N[(CH₂)ₙ-with COOH branch]-C(=O)-CH(R¹)-NH-CH(R²)-COOR³

| No. | n | R¹ | R² | R³ | Method | NMR |
|---|---|---|---|---|---|---|
| 620 | 1 | CH₃ | -CH₂-CH₂-C₆H₃(OCH₃)(OCH₃) (3,4-dimethoxyphenyl) | C₂H₅ | B | 7.2–6.3m(3H); 3.9s(6H); 2.7m(2H); 2.0–1.0m(14H); 1.2d(3H) |
| 621 | 1 | CH₃ | -CH₂-CH₂-C₆H₃(Cl)(OCH₃) (5-chloro-2-methoxyphenyl) | C₂H₅ | B | 7.3–6.4m(3H); 3.8s(3H); 2.6m(2H); 2.0–1.0m(14H) |
| 622 | 1 | CH₃ | -CH₂-CH₂-C₆H₃(Cl)(Cl) (2,3-dichlorophenyl) | C₂H₅ | B | 7.4–6.8m(3H); 2.7m(2H); 2.0–1.0m(14H); 1.2d(3H) |
| 623 | 1 | -CH₂-(imidazol-4-yl) | -CH₂-CH₂-C₆H₂(OCH₃)(OCH₃)(OCH₃) (3,4,5-trimethoxyphenyl) | C₂H₅ | B | 13.1s(1H); 7.5–6.2m(4H); 3.9s(9H); 2.8–2.3m(4H); 2.0–1.0m(14H) |
| 624 | 1 | CH₃ | -CH₂-CH₂-(pyrrol-2-yl, NH) | C₂H₅ | B | 7.3–6.0m(3H); 2.8m(2H); 2.0–1.0m(14H); 1.2d(3H) |
| 625 | 1 | CH₃ | -CH₂-CH₂-(thiophen-2-yl, S) | C₂H₅ | B | 7.3–6.9m(3H); 2.9m(2H); 2.0–1.0m(14H); 1.2d(3H) |

-continued
| | | | | | R³ | Method | NMR |
|---|---|---|---|---|---|---|---|
| No. | n | R¹ | R² | | | | |
| 626 | 1 | H₂N—(CH₂)₄ | 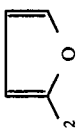 | | H | B | 7.4–6.3m(3H); 2.8–2.3m(4H); 2.0–1.0m(20H) |
| 627 | 1 | CH₃ | 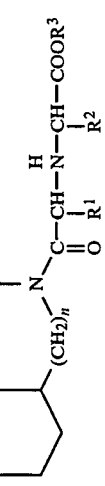 | | C₂H₅ | B | 8.6–7.1m(4H); 2.9m(2H); 2.0–1.0m(14H); 1.2d(3H) |
| 628 | 1 | CH₃ | 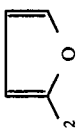 | | C₂H₅ | B | 7.8–6.5m(6H); 2.9m(2H); 2.0–1.0m(14H); 1.2d(3H) |
| 629 | 1 | CH₃ | 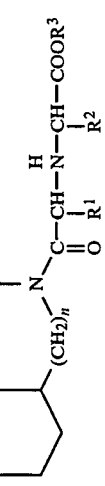 | | C₂H₅ | B | 6.7s(1H); 3.9–3.0m+s(6H); 2.8m(2H); 2.0s(3H); 2.0–1.0m(14H); 1.2d(3H) |
| 630 | 1 | CH₃ | 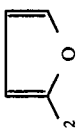 | | C₂H₅ | B | 5.2s(1H); 3.2 2s(6H); 2.9m(2H); 2.0–1.0m(14H) 1.2d(3H) |
| 631 | 1 | CH₃ | 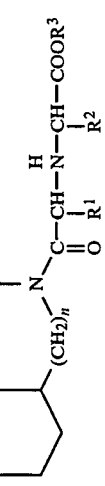 | | C₂H₅ | B | 8.1s(1H); 3.2s(3H); 2.9m(2H); 2.0–1.0m(14H); 1.2d(3H) |

-continued

Structure:

$$\text{cyclohexane-CH}_2\text{-(CH}_2)_n\text{-N(C(=O)-CH(R}^1\text{)-N(H)-CH(R}^2\text{)-COOR}^3\text{)-CH}_2\text{-COOH}$$

| No. | n | R¹ | R² | R³ | Method | NMR |
|---|---|---|---|---|---|---|
| 632 | 1 | CH₃ | 1-(CH₂CH₂)-isoquinoline | C₂H₅ | B | 8.5-7.5m(6H); 3.9-3.0m(5H); 2.0-1.0m(14H); 1.2d(3H) |
| 633 | 1 | CH₃ | 4-(CH₂CH₂)-quinoline | C₂H₅ | B | 8.8-7.4m(6H); 3.9-3.0m(5H); 2.0-1.0m(14H); 1.2d(3H) |
| 634 | 1 | CH₃ | CH₂CH₂-(1H-tetrazol-5-yl) | C₂H₅ | B | 13.0s(1H); 3.9-2.9m(5H) 2.0-1.0m(14H); 1.2d(3H) |
| 635 | 1 | CH₃ | CH₂CH₂-(isoxazol-4-yl) | C₂H₅ | B | 7.9-7.4 2s(2H); 2.8m(2H) 2.0-1.0m(14H); 1.2d(3H) |
| 636 | 1 | CH₃ | CH₂-(2-amino-thiazol-4-yl)-CH₂ | C₂H₅ | B | 8.0s(1H); 2.8m(2H); 2.0-1.0m(14H); 1.2d(3H) |
| 637 | 1 | CH₃ | CH₂CH₂-(5-chloro-1,3-dimethyl-2-oxo-2,3-dihydro-1H-imidazol-4-yl) | C₂H₅ | B | 3.2 2s(6H); 3.9-3.0m(5H); 2.0-1.0m(14H); 1.2d(3H) |

-continued

Structure: cyclohexane with CH2-CH(COOH)-N((CH2)n-...)- where N connects to C(=O)-CH(R1)-N(H)-CH(R2)-COOR3

| No. | n | R1 | R2 | R3 | Method | NMR |
|---|---|---|---|---|---|---|
| 638 | 1 | CH3 | CH3-CHCH2- (isobutyl) | C2H5 | B | 7.2bs(5H); 2.7m(2H); 2.2-1.0m(13H); 1.2d(3H); 1.0d(3H) |
| 639 | 1 | H2N—(CH2)4 | 4-Cl-C6H4-CH2-CH2- | H | B | 7.4-7.0m(4H); 2.7-2.3m(4H); 2.0-1.0m(22H) |
| 640 | 1 | CH3 | 4-OCH3-C6H4-C(CH3)2-CH2-CH2- | C2H5 | B | 7.3-6.3m(4H); 3.9s(3H); 2.0-1.0m(16H); 1.2d(3H); 1.0s(6H) |
| 641 | 1 | HN=C(NH2)-NH-(CH2)3 | C6H5-CH2- | H | B | 7.2bs(5H); 2.9-2.6m(4H); 2.0-1.0m(16H) |
| 642 | 1 | H | 2-F-C6H4-CH2- | H | B | 7.4-6.9m(4H); 3.9-3.0m(4H); 2.7m(2H) |
| 643 | 1 | H | 4-COOH-C6H4-CH2- | H | B | 7.8-7.0m(4H); 3.9-3.0m(4H); 2.7m(2H) |
| 644 | 1 | H | 3-OH-C6H4-CH2-CH2-CH2-CH2- | H | B | 7.3-6.5m(4H); 3.9-3.0m(4H); 2.7m(2H); 2.0-1.0m(18H) |

-continued

Structure:

$$\text{cyclohexane-CH}(CH_2)_n\text{-N}(CH_2\text{-COOH})\text{-C}(=O)\text{-CH}(R^1)\text{-NH-CH}(R^2)\text{-COOR}^3$$

| No. | n | $R^1$ | $R^2$ | $R^3$ | Method | NMR |
|---|---|---|---|---|---|---|
| 645 | 1 | $CH_3$ | $CH_2$-C$_6$H$_4$-CONH$_2$ (p) | H | B | 7.8–7.0m(4H); 2.8m(2H); 1.2d(3H) |
| 646 | 1 | $CH_3$ | $CH_2$-C$_6$H$_4$-NH$_2$ (p) | H | B | 7.2–6.4m(4H); 2.7m(2H); 1.2d(3H) |
| 647 | 1 | $CH_3$ | $CH_2$-C$_6$H$_3$(OCH$_3$)$_2$ | H | B | 7.2–6.3m(3H); 3.9s(6H); 2.7m(2H); 1.2d(3H) |
| 648 | 1 | $(CH_3)_2CH-CH_2$ | $CH_2CH_2$-C$_6$H$_3$(OCH$_3$)(Cl) | $C_2H_5$ | B | 7.2–6.4m(3H); 3.8s(3H); 2.8m(2H); 2.0–1.0m(17H); 0.9d(6H) |
| 649 | 1 | $CH_3$ | $-CH_2$-(indol-3-yl) | $C_2H_5$ | B | 7.8–6.5m(6H); 2.9m(2H); 1.2d(3H) |
| 650 | 1 | $(CH_3)_2CH-CH_2$ | $CH_2CH_2$-C$_6$H$_2$(OCH$_3$)$_3$ | H | B | 7.2–6.2m(3H); 3.9s(9H); 2.7m(2H); 2.0–1.0m(17H); 0.9d(6H) |

-continued

Structure:

CH₂-CH(COOH)-N((CH₂)ₙ-)-C(=O)-CH(R¹)-N(H)-CH(R²)-COOR³, with cyclohexane ring attached to the CH₂ groups.

| No. | n | R¹ | R² | R³ | Method | NMR |
|---|---|---|---|---|---|---|
| 651 | 1 | CH₃ | CH₂-(pyrrole, NH) | H | B | 7.3–6.0m(3H); 2.8m(2H); 1.2d(3H) |
| 652 | 1 | CH₃ | CH₂-(thiophene) | H | B | 7.3–6.9m(3H); 2.9m(2H); 1.2d(3H) |
| 653 | 1 | CH₃ | CH₂-(furan)-CH₃ | H | B | 7.4–6.3m(3H); 2.8m(2H); 1.2d(3H) |
| 654 | 1 | CH₃ | CH₂-(pyridine) | H | B | 8.6–7.1m(4H); 2.9m(2H); 1.2d(3H) |
| 655 | 1 | CH₃ | CH₂-(indole, NH) | H | B | 7.8–6.5m(6H); 2.9m(2H); 1.2d(3H) |
| 656 | 1 | (CH₃)₂CH—CH₂ | CH₂-(1,3-dimethylpyrazole) | C₂H₅ | B | 6.5s(1H); 3.9–3.0m+s(6H); 2.8m(2H); 2.0s(3H); 2.0–1.0m(15H); 1.0d(6H) |

-continued
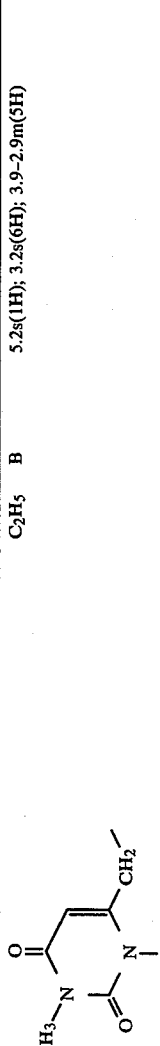
| No. | n | R¹ | R² | R³ | Method | NMR |
|---|---|---|---|---|---|---|
| 657 | 1 | H |  | $C_2H_5$ | B | 5.2s(1H); 3.2s(6H); 3.9–2.9m(5H) |
| 658 | 1 | $CH_3$ | 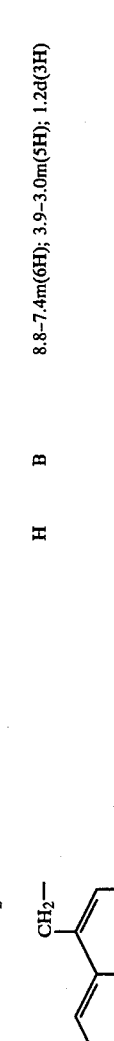 | H | B | 8.5–7.5m(6H); 3.9–3.0m(5H); 1.2d(3H) |
| 659 | 1 | $CH_3$ | 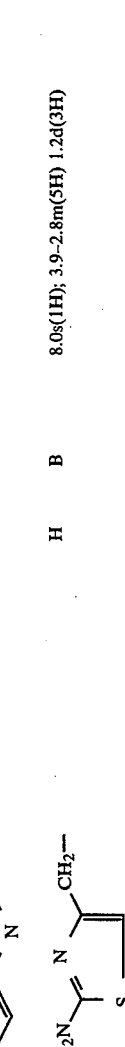 | H | B | 8.8–7.4m(6H); 3.9–3.0m(5H); 1.2d(3H) |
| 660 | 1 | $CH_3$ |  | H | B | 8.0s(1H); 3.9–2.8m(5H) 1.2d(3H) |
| 661 | 1 | $CH_3$ |  | H | B | 8.1s(1H); 6.4s(1H); 3.7s(3H); 3.9–2.9m(5H) 1.2d(3H) |
| 662 | 1 | $(CH_3)_2CH-CH_2$ |  | H | B | 8.1s(1H); 6.4s(1H); 3.7s(3H); 3.9–2.9m(5H); 2.0–1.0m(17H); 1.0d(6H) |

-continued
| No. | n | R¹ | R² | R³ | Method | NMR |
|---|---|---|---|---|---|---|
| 663 | 1 | CH₃ | 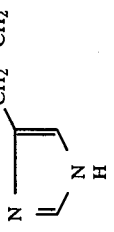 | C₂H₅ | B | 7.7–7.1m(2H); 3.9–2.9m(5H); 2.0–1.0m(14H) 1.2d(3H) |
| 664 | 1 | CH₃ |  | C₂H₅ | B | 7.7–7.1m(2H); 3.9–2.9m(5H); 1.2d(3H) |
| 665 | 0 | CH₃ | 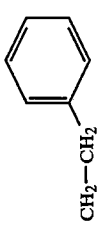 | C₂H₅ | B | 7.2–6.5m(5H); 2.7m(2H); 2.0–1.0m(13H); 1.2d(3H) |
| 666 | 0 | CH₃ | 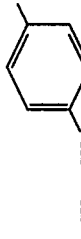 | H | B | 7.5–6.5m(4H); 2.7m(2H); 2.0–1.0m(13H); 1.2d(3H) |
| 667 | 0 | CH₃ | 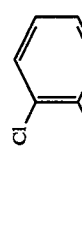 | H | B | 7.6–6.5m(3H); 4.5–2.8m(5H); 2.0–1.0m(13H); 1.2d(3H) |
| 668 | 0 | CH₃ |  | H | B | 7.3–6.0m(3H); 2.8m(2H); 2.0–1.0m(13H); 1.2d(3H) |

-continued
| No. | n | R$^1$ | R$^2$ | R$^3$ | Method | NMR |
|---|---|---|---|---|---|---|
| 669 | 0 | CH$_3$ |  | H | B | 7.3–6.5m(3H); 4.5–2.9m(5H); 2.0–1.0m(13H); 1.2d(3H); |
| 670 | 0 | CH$_3$ |  | H | B | 8.6–6.5m(4H); 4.5–2.9m 2.0–1.0m(13H); 1.2d(3H) |
| 671 | 0 | CH$_3$ |  | C$_2$H$_5$ | B | 7.8–6.5m(6H); 4.5–2.9m(5H); 2.0–1.0m(13H); 1.2d(3H) |
| 672 | 0 | CH$_3$ | CH$_3$\CH—CH$_2$— | C$_2$H$_5$ | B | 7.2–6.5(5H); 4.5–2.9m(5H); 2.0–1.0m(12H); 1.2d(3H); 1.1d(3H) |
| 673 | 0 | CH$_3$ | 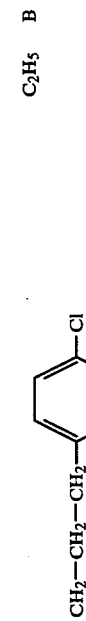 | C$_2$H$_5$ | B | 7.4–6.5(4H); 2.7–2.3m(2H); 2.0–1.0m(15H); 1.2d(3H) |
| 674 | 0 | CH$_3$ |  | C$_2$H$_5$ | B | 7.3–6.3(4H); 3.9s(3H); 2.0–1.0m(15H); 1.2d(3H); 1.0s(6H) |

-continued structure: CH2-(cyclohexyl)-(CH2)n-N(CH2-COOH)-C(=O)-CH(R1)-NH-CH(R2)-COOR3

| No. | n | R¹ | R² | R³ | Method | NMR |
|-----|---|----|----|----|--------|-----|
| 675 | 0 | CH₃ | -CH₂-C₆H₃(OCH₃)(Cl) | C₂H₅ | B | 7.2–6.3(3H); 3.0s(3H); 2.7m(2H); 2.0–1.0m(13H); 1.2d(3H) |
| 676 | 0 | CH₃ | -CH₂-(indol-3-yl) | C₂H₅ | B | 7.8–6.5m(6H); 4.5–2.9m(5H); 1.2d(3H) |
| 677 | 0 | CH₃ | -CH₂-(imidazol-4-yl)-CH₂-CH₂- | C₂H₅ | B | 7.7–6.5m(2H); 4.5–2.9m(5H); 2.0–1.0m(13H); 1.2d(3H) |
| 678 | 0 | CH₃ | -CH₂-(imidazol-4-yl)-CH₂- | C₂H₅ | B | 7.7–6.5m(2H); 4.5–2.9m(5H); 1.2d(3H) |
| 679 | 1 | CH₃ | (CH₃)₂-CH-CH₂-CH₂-CH₂ | C₂H₅ | A | 2.0–1.0m(19H); 1.2d(3H); 0.9d(6H) |
| 680 | 1 | H₂N—(CH₂)₄ | (CH₃)₂CH-CH₂-CH₂ | C₂H₅ | B | 2.4m(2H); 2.0–1.0m(23H); 0.9d(6H) |
| 681 | 1 | H₂N—(CH₂)₃ | (CH₃)₂CH—CH₂ | C₂H₅ | B | 2.0–1.0m(19H); 0.9d(6H) |
| 682 | 0 | FCH₂ | (CH₃)₂CH | C₂H₅ | B | 4.3d(2H); 2.0–1.0m(12H); 0.9d(6H) |
| 683 | 1 | CH₃—CH₂—CH(CH₃)— | -CH₂-cyclohexyl | H | A | 2.0–1.0m(28H); 1.0d+t(6H) |

-continued

Structure: cyclohexane with CH₂-CH(COOH)-N((CH₂)ₙ-R²)-C(=O)-CH(R¹)-NH-CH(R²)-COOR³

| No. | n | $R^1$ | $R^2$ | $R^3$ | Method | NMR |
|---|---|---|---|---|---|---|
| 684 | 1 | $CH_3$ | CH₂—CH₂—(2-naphthyl) | $C_2H_5$ | A | 7.8-7.0m(7H); 2.7m(2H); 2.0-1.0m(14H); 1.2d(3H) |
| 685 | 1 | $CH_3$ | CH₂—(4-OH-phenyl) | H | B | 7.3-6.5m(4H); 2.8m(2H); 1.2d(3H) |
| 686 | 1 | $CH_3$ | CH₂—(4-OCH₃-phenyl) | H | B | 7.3-6.4m(4H); 3.9s(3H); 3.9-2.9m(5H); 1.2d(3H) |
| 687 | 1 | $CH_3$ | CH₂—(3-OCH₃-phenyl) | $C_2H_5$ | B | 7.6-6.4m(4H); 3.8s(3H); 3.9-2.9m(5H); 1.2d(3H) |
| 688 | 0 | $CH_3$ | CH₂—CH₂—(4-Cl-phenyl) | $C_2H_5$ | B | 7.5-6.5m(4H); 2.7m(2H); 2.0-1.0m(13H); 1.2d(3H) |
| 689 | 0 | $CH_3$ | CH₂—CH₂—(4-F-phenyl) | $C_2H_5$ | B | 7.5-6.6m(4H); 2.7m(2H); 2.0-1.0m(13H); 1.2d(3H) |
| 690 | 0 | $CH_3$ | CH₂—CH₂—(2-CH₃-phenyl) | $C_2H_5$ | B | 7.4-7.0m(4H); 2.6m(2H); 2.3s(3H); 2.0-1.0m(13H); 1.2d(3H) |

-continued

| No. | n | R¹ | R² | R³ | Method | NMR |
|---|---|---|---|---|---|---|
| 691 | 0 | CH₃ | CH₂—CH₂— (2,6-dichlorophenyl) | C₂H₅ | B | 7.6–6.5m(3H); 4.5–2.8m(5H); 2.0–1.0m(13H); 1.2d(3H) |
| 692 | 0 | CH₃ | CH₂—CH₂— (2,4-dichlorophenyl) | C₂H₅ | B | 7.5–6.5m(3H); 4.5–2.8m(5H); 2.0–1.0m(13H); 1.2d(3H) |
| 693 | 0 | CH₃ | CH₂—CH₂— (4-methoxyphenyl) | C₂H₅ | B | 7.3–6.4m(4H); 4.5–2.8m(8H); 2.0–1.0m(13H); 1.2d(3H) |
| 694 | 0 | CH₃ | CH₂—CH₂— (2,4-dimethoxyphenyl) | C₂H₅ | B | 7.2–6.3m(3H); 3.9s(6H); 4.5–2.5m(5H); 2.0–1.0m(13H); 1.2d(3H) |
| 695 | 0 | CH₃ | CH₂—CH₂— (thiophen-2-yl) | C₂H₅ | B | 7.3–6.5m(3H); 4.5–2.9m(5H); 2.0–1.0m(13H); 1.2d(3H) |

I claim:
1. A compound of the formula

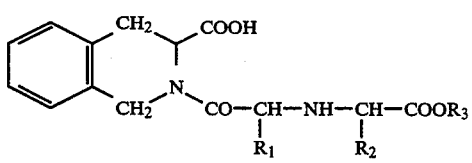

or physiologically tolerated salt thereof, wherein COOR$_3$ is
a) carboxyl,
b) carboxyl ester and
R$_1$ is
a) alkyl or alkenyl having up to 6 C atoms,
b) alkyl or alkenyl having up to 6 C atoms substituted by
  1) (C$_5$-C$_7$)-cycloalkyl,
  2) (C$_5$-C$_7$)-cycloalkenyl,
  3) hydroxy,
  4) (C$_1$-C$_2$)-alkoxy,
  5) phenoxy,
  6 phenoxy substituted by
    6.1) halogen,
    6.2) (C$_1$-C$_2$)-alkyl, or
    6.3) (C$_1$-C$_2$)-alkoxy,
  7) naphthyloxy,
  8) monoalkylamino having up to 7 C atoms,
  9) monoalkylamino having up to 7 C atoms substituted in the alkyl part by
    9.1) hydroxy,
    9.2) carboxy,
    9.3) carboxamido,
    9.4) carboethoxy,
    9.5) amino,
    9.6) alkylamino,
    9.7) dialkylamino,
    9.8) piperidino, or
    9.9) morpholino,
  10) dialkylamino having up to 7 C atoms,
  11) dialkylamino having up to 7 C atoms substituted as defined in b) 9.1-9.9,
  12) monocycloalkylamino having up to 7 C atoms,
  13) dicycloalkylamino having up to 7 C atoms,
  14) alkyloxycarbonylamino,
  15) phenoxycarbonylamino,
  16) phenoxycarbonylamino substituted as defined in b) 6.1-6.3,
  17) naphthyloxycarbonylamino,
  18) benzyloxycarbonylamino or phenethyloxycarbonylamino,
  19) benzyloxycarbonylamino or phenethyloxycarbonylamino each substituted in the aryl part by
    19.1) halogen,
    19.2) nitro,
    19.3) (C$_1$-C$_2$)-alkyl, or
    19.4) (c$_1$-C$_2$)-alkoxy.
  20) alkylureido,
  21) phenylureido,
  22) phenylureido substituted as defined in b) 6.1-6.3,
  23) naphthylureido,
  24) benzylureido or phenethylureido,
  25) benzylureido or phenethylureido each substituted as defined in b) 19.1-19.4,
  26) formyl,
  27) alkanoylamino,
  28) benzoylamino,
  29) benzoylamino substituted as defined in b) 6.1-6.3,
  30) naphthoylamino,
  31) phenylamino or naphthylamino,
  32) phenylamino or naphthylamino each mono- or di-substituted by
    32.1) (C$_1$-C$_2$)-alkyl,
    32.2) (C$_1$-C$_2$)-alkoxy,
    32.3) methylenedioxy,
    32.4) amino,
    32.5) hydroxy,
    32.6) acetoxy,
    32.7) carboxy,
    32.8) carboxamido,
    32.9) carboethoxy,
    32.10) halogen, or
    32.11) nitro,
  33) benzylamino or phenethylamino,
  34) benzylamino or phenethyl amino each mono- or di-substituted in the aryl part as defined in b) 32.1-32.11,
  35) (C$_1$-C$_7$)-alkylmercapto, (C$_1$-C$_7$)-alkylsulfinyl, or (C$_1$-C$_7$)-alkylsulfonyl
  36) (C$_1$-C$_7$)-alkylmercapto, (C$_1$-C$_7$)-alkylsulfinyl, or (C$_1$-C$_7$)-alkylsulfonyl each substituted by
    36.1) methoxy,
    36.2) ethoxy,
    36.3) hydroxy,
    36.4) carboxy,
    36.5) carboxamido,
    36.6) carboethoxy,
    36.7) amino, or
    36.8) alkylamino,
  37) phenylmercapto or naphthylmercapto, phenylsulfinyl or naphthylsulfinyl, or phenylsulfonyl or nephthylsulfonyl,
  38) phenylmercapto or naphthylmercapto, phenylsulfinyl or naphthylsulfinyl, or phenylsulfonyl or naphthylsulfonyl each substituted
    38.1) as defined in b) 36.1-36.8 or substituted by
    38.2) halogen,
    38.3) nitro, or
    38.4) sulfonamido,
  39) benzylmercapto, benzylsulfinyl, or benzylsulfonyl,
  40) benzylmercapto, benzylsulfinyl, or benzylsulfonyl each substituted
    40.1) in the alkyl part as defined in b) 36.1-36.8 or
    40.2) in the aryl part as defined in b) 38.1-38.4,
  41) carboxy,
  42) carboethoxy,
  43) carboxamido,
  44) alkylaminocarbonyl having up to 6 C atoms,
  45) cycloalkylaminocarbonyl having up to 6 C atoms,
  46) cycloalkyleneaminocarbonyl having up to 6 C atoms,
  47) dialkylaminocarbonyl having up to 6 C atoms,
  48) phenylaminocarbonyl,
  49) phenylaminocarbonyl substituted as defined in b) 6.1-6.3,
  50) naphthylaminocarbonyl,
  51) benzylaminocarbonyl or phenethylaminocarbonyl, 52) benzylaminocarbonyl or phenethylaminocarbonyl each substituted as defined in b) 19.1–19.4,
53) guanido,
54) phenyl,
55) phenyl substituted by
   55.1) halogen
   55.2) hydroxy,
   55.3) acetoxy,
   55.4) carboxy,
   55.5) carboxamido,
   55.6) sulfonamido,
   55.7) nitro,
   55.8) methyl,
   55.9) ethyl,
   55.10) methoxy, or
   55.11) ethoxy,
56) naphthyl, dihydronaphthyl, or tetrahydronaphthyl,
57) naphthyl, dihydronaphthyl, or tetrahydronaphthyl, each substituted as defined in b) 55.1–55.11,
58) imidazol-4-ethyl, or
59) indolemethyl,
c) ($C_5$–$C_7$)-cycloalkyl or ($C_5$–$C_7$)-cycloalkenyl,
d) phenyl,
e) naphthyl, dihydronaphthyl, or tetrahydronaphthyl,
f) imidazol-4-ethyl,
g) indolemethyl, or
h) the side-chain of a naturally occurring L-amino acid, $R_2$ is
a) alkyl or alkenyl having up to 6 C atoms,
b) alkyl or alkenyl having up to 6 C atoms, substituted by
   1) ($C_5$–$C_7$)-cycloalkyl,
   2) ($C_5$–$C_7$)-cycloalkenyl,
   3) hydroxy,
   4) ($C_1$–$C_2$)-alkoxy,
   5) phenoxy,
   6) phenoxy substituted by
      6.1) halogen
      6.2) ($C_1$–$C_2$)-alkyl,
      6.3) ($C_1$–$C_2$)-alkoxy,
      6.4) nitro, or
   7) naphthyloxy,
   8) benzyloxy,
   9) benzyloxy substituted in the aryl part by
      9.1) methoxy,
      9.2) carboxamido,
      9.3) amino,
      9.4) halogen,
      9.5) nitro, or
   10) monoalkylamino having up to 7 C atoms,
   11) monoalkylamino having up to 7 C atoms, substituted in the alkyl part by
      11.1) hydroxy,
      11.2) carboxy,
      11.3) carboxamido,
      11.4) carboethoxy,
      11.5) amino,
      11.6) alkylamino,
      11.7) dialkylamino,
      11.8) piperidino, or
      11.9) morpholino,
   12) dialkylamino having up to a total of 7 C atoms,
   13) dialkylamino having up to a total of 7 C atoms substituted as defined in b) 11.1–11.9,
   14) monocycloalkylamino having up to 7 C atoms,
   15) dicycloalkylamino having up to 7 C atoms,
   16) alkoxycarbonylamino,
   17) phenoxycarbonylamino,
   18) phenoxycarbonylamino substituted as defined in b) 6.1–6.3,
   19) nephthyloxycarbonylamino,
   20) benzyloxycarbonylamino or phenethyloxycarbonylamino,
   21) benzyloxycarbonylamino or phenethyloxycarbonylamino each substituted in the aryl part by
      21.1) halogen,
      21.2) nitro,
      21.3) ($C_1$–$C_2$)-alkyl, or
      21.4) ($C_1$–$C_2$)-alkoxy,
   22) ($C_1$–$C_{10}$)-alkylureido,
   23) phenylureido,
   24) phenylureido substituted as defined in b) 6.1, 6.2, 6.3 or by nitro,
   25) naphthylureido,
   26) benzylureido or phenethylureido,
   27) benzylureido or phenethylureido each substituted as defined in b) 21.1–21.4,
   28) formyl,
   29) alkanoylamino,
   30) benzoylamino,
   31) benzoylamino mono- to di-substituted by
      31.1) halogen,
      31.2) ($C_1$–$C_2$)-alkyl,
      31.3) ($C_1$–$C_2$)-alkoxy,
      31.4) hydroxy,
      31.5) carboxy,
      31.6) nitro, or
      31.7) amino,
   32) naphthoylamino,
   33) phenylamino or naphthylamino,
   34) phenylamino or naphthylamino each mono- or di-substituted by
      34.1) ($C_1$–$C_2$)-alkyl,
      34.2) ($C_1$–$C_2$)-alkoxy,
      34.3) methylenedixoy,
      34.4) amino,
      34.5) hydroxy,
      34.6) acetoxy,
      34.7) carboxy,
      34.8) carboxamido,
      34.9) carboethoxy,
      34.10) halogen, or
      34.11) nitro,
   35) benzylamino or phenethylamino,
   36) benzylamino or phenethylamino each mono- or di-substituted in the aryl part as defined in b) 34.1–34.11,
   37) ($C_1$–$C_7$)-alkylmercapto, ($C_1$–$C_7$)-alkylsulfinyl, or ($C_1$–$C_7$)-alkylsulfonyl,
   38) ($C_1$–$C_7$)-alkylmercapto, ($C_1$–$C_7$)-alkylsulfinyl, or ($C_1$–$C_7$)-alkylsulfonyl each substituted by
      38.1) methoxy,
      38.2) ethoxy,
      38.3) hydroxy,
      38.4) carboxy,
      38.5) carboxamido,
      38.6) carboethoxy,
      38.7) amino, or
      38.8) alkylamino
   39) phenylmercapto or naphthylmercapto, phenylsulfinyl or naphthylsulfinyl, or phenylsulfonyl or naphthylsulfonyl, 40) phenylmercapto or naphthylmercapto, phenylsulfinyl or naphthylsulfinyl, or phenylsulfonyl or naphathylsulfonyl each substituted
  40.1) as defined in b) 38.1–38.8, or substituted by
  40.2) halogen,
  40.3) nitro,
  40.4) sulfonamido, or
41) benzylmercapto, benzylsulfinyl, or benzylsulfonyl,
42) benzylmercapto, benzylsulfinyl, or benzylsulfonyl each substituted
  42.1) in the alkyl part as defined in b) 38.1–38.8 or
  42.2) in the aryl part as defined in b) 40.1–40.4,
43) carboxy,
44) alkylaminocarbonyl having up to 6 C atoms,
45) cycloalkylaminocarbonyl having up to 6 C atoms,
46) cycloalkyleneaminocarbonyl having up to 6 C atoms,
47) dialkylaminocarbonyl having up to 6 C atoms,
48) phenylaminocarbonyl,
49) phenylaminocarbonyl mono- to di-substituted by
  49.1) halogen,
  49.2) ($C_1$–$C_2$)-alkyl,
  49.3) ($C_1$–$C_2$)-alkoxy,
  49.4) carboxyl,
  49.5) carboxyamido,
  49.6) hydroxy, or
  49.7) nitro,
50) naphthylaminocarbonyl,
  61.1) halogen,
  61.2) hydroxy,
  61.3) acetoxy,
  61.4) carboxy,
  61.5) carboxamido,
  61.6) sulfonamido,
  61.7) nitro,
  61.8) methyl,
  61.9) ethyl,
  61.10) methoxy,
  61.11) ethoxy, or
c) ($C_5$–$C_7$)-cycloalkyl- or cycloalkenyl,
d) naphthyl, dihydronaphthyl, or tetrahydronaphthyl,
e) a 5-membered or 6-membered monocyclic heterocyclic structure, the hetero atoms of which are
  1) 1 or 2 S atoms or 1 O atom and 0 or 1 N atom or
  2) up to 4 N atoms,
f) a heterocycle as defined in e) substituted by
  1) halogen,
  2) oxo,
  3) S-oxo,
  51) benzylaminocarbonyl or phenethylaminocarbonyl,
  52) benzylaminocarbonyl or phenethylaminocarbonyl each substituted as defined in b) 21.1–21.4,
  53) guanido,
  54) naphthyl, dihydronaphthyl, or tetrahydronaphthyl,
  55) naphthyl, dihydronaphthyl, or tetrahydronaphthyl, each substituted by
    55.1) halogen,
    55.2) hydroxy,
    55.3) acetoxy,
    55.4) carboxy,
    55.5) carboxamido,
    55.6) sulfonamido,
    55.7) nitro,
    55.8) methyl,
    55.9) ethyl,
    55.10) methoxy, or
    55.11) ethoxy,
56) a 5-membered or 6-membered monocyclic heterocyclic structure, the hetero atoms of which are
  56.1) 1 or 2 S atoms or 1 O atom and 0 or 1 N atom or
  56.2) up to 4N atoms
57) a heterocycle as defined in b) 56 substituted by
  57.1) halogen,
  51.2) oxo,
  57.3) S-oxo,
  57.4) hydroxy,
  57.5) carboxy,
  57.6) carboxamido,
  57.7) sulfonamido,
  57.8) nitro,
  57.9) ($C_1$–$C_9$)-alkyl,
  57.10) benzyl or phenethyl,
  57.11) methoxy,
  57.12) ethoxy, or
58) a 9-membered or 10-membered bicyclic heterocyclic structure, the hetero atoms of which are 2 O atoms or 1 or 2 N atoms or
59) a heterocycle as defined in b) 58 substituted as defined in b) 57.1–57.12,
60) phenyl or
61) phenyl mono- to di-substituted by
  4) hydroxy,
  5) carboxy,
  6) carboxamido,
  7) sulfonamido,
  8) nitro,
  9) ($C_1$–$C_9$)-alkyl,
  10) benzyl or phenethyl,
  11) methoxy, or
  12) ethoxy,
g) a 9-membered or 10-membered bicyclic heterocyclic structure, the hetero atoms of which are 2 O atoms or 1 or 2 N atoms or
h) a heterocycle as defined in g) substituted as defined in f) 1–12,
i) phenyl.

2. A compound as in claim 1 wherein $R_2$ is
a) alkyl having up to 6 C atoms,
b) alkyl having up to 6 C atoms substituted by
  1) ($C_5$–$C_7$)-cycloalkyl,
  2) ($C_1$–$C_2$)-alkoxy,
  3) ($C_1$–$C_2$)-alkoxy substituted by
    3.1) Alkylamino
  4) phenoxy,
  5) phenoxy substituted by
    5.1) halogen
    5.2) ($C_1$–$C_2$)-alkyl, or
    5.3) ($C_1$–$C_2$)-alkoxy,
  6) benzyloxy,
  7) benzyloxy substituted in the aryl part by
    7.1) methoxy,
    7.2) carbo amido,
    7.3) amino,
    7.4) halogen, or
    7.5) nitro,
  8) monoalkylamino having up to 7 C atoms, 9) monoalkylamino having up to 7 C atoms substituted in the alkyl part by
   9.1) carboxamido,
   9.2) carboethoxy,
   9.3) dialkylamino,
10) dialkylamino having up to 7 C atoms,
11) alkoxycarbonylamino,
12) benzyloxycarbonylamino,
13) ($C_1$–$C_{10}$)-alkylureido,
14) phenylureido,
15) phenylureido substituted by
   15.1) halogen,
   15.2) nitro,
   15.3) ($C_1$–$C_2$)-alkyl, or
   15.4) ($C_1$–$C_2$)-alkoxy,
16) alkanoylamino,
17) benzoylamino,
18) benzoylamino mono- or di-substituted by
   18.1) halogen,
   18.2) ($C_1$–$C_2$)-alkyl,
   18.3) ($C_1$–$C_2$)-alkoxy,
   18.4) hydroxy,
   18.5) carboxy,
   18.6) nitro, or
   18.7) amino,
19) phenylamino,
20) phenylamino substituted by
   20.1) ($C_1$–$C_2$)-alkyl,
   20.2) ($C_1$–$C_2$)-alkoxy,
   20.3) methylenedioxy,
   20.4) amino,
   20.5) hydroxy,
   20.6) acetoxy,
   20.7) carboxamido,
   20.8) carboethoxy,
   20.9) halogen, or
   20.10) nitro,
21) ($C_1$–$C_7$)-alkylmercapto, ($C_1$–$C_7$)-alkylsulfinyl, or ($C_1$–$C_7$)-alkylsulfonyl,
22) ($C_1$–$C_7$)-alkylmercapto, ($C_1$–$C_7$)-alkylsulfinyl, or ($C_1$–$C_7$)-alkylsulfonyl substituted by
   22.1) ethoxy,
   22.2) carboxamido,
   22.3) carboethoxy, or
23) phenylmercapto, phenylsulfinyl, or phenylsulfonyl,
24) phenylmercapto, phenylsulfinyl, or phenylsulfonyl substituted by
   24.1) methoxy,
   24.2) carboxy,
   24.3) carboxamido,
   24.4) amino,
   24.5) nitro,
   24.6) halogen, or
   24.7) sulfonamido,
25) benzylmercapto, benzylsulfinyl, or benzylsulfonyl,
26) carboxy,
27) cycloalkylaminocarbonyl up to 6 C atoms,
28) dialkylaminocarbonyl up to 6 C atoms,
29) phenylaminocarbonyl,
30) phenylcarbonyl substituted by
   30.1) halogen,
   30.2) ($C_1$–$C_2$)-alkyl,
   30.3) carboxy,
   30.4) carboxamido,
   30.5) carboethoxy,
   30.6) hydroxy, or
   30.7) nitro,
31) phenyl,
32) phenyl mon- or di-substituted by
   32.1) halogen,
   32.2) hydroxy,
   32.3) carboxy,
   32.4) carboxamido,
   32.5) nitro,
   32.6) methyl, or
   32.7) methoxy,
33) naphthyl,
34) a 5-membered or 6-membered monocyclic heterocyclic structure, the hetero atoms of which are
   34.1) 1 or 2 S atoms or 1 O atoms and 0 or 1 N atom or
   34.2) up to 4 N atoms,
35) a heterocycle as defined in b) 35 substituted by
   35.1) halogen,
   35.2) oxo,
   35.3) ($C_1$–$C_9$)-alkyl, or
   35.4) methoxy,
36) a 9-membered or 10-membered bicyclic heterocyclic structure, the hetero atoms of which are 2 O atoms or 1 or 2 N atoms
c) ($C_5$–$C_7$)-cycloalkenyl, or
d) a 5-membered or 6-membered monocyclic heterocyclic structure, the hetero atoms of which are
   1) 1 or 2 S atoms or 1 O atom and 0 or 1 N atom or
   2) 1, 2 or 4 N atoms.

3. A compound as in claim 1 wherein $R_1$ is methyl, ethyl, n-propyl, isopropyl, n-butyl, isobutyl, tertiary-butyl, linear or branched pentyl or hexyl, cyclopentyl, cyclohexyl, cycloheptyl, cyclopentenyl, cyclohexenyl, cycloheptenyl, phenyl, naphthyl, dihydronaphthyl, tetrahydronaphthyl, benzyl, phenethyl, p-fluorophenethyl, o-methylphenethyl, p-methoxyphenethyl, 2,4-dichlorophenethyl, or cyclohexylethyl.

4. A compound as in claim 1 wherein $R_2$ is methyl, ethyl, n-propyl, isopropyl, n-butyl, isobutyl, tertiary-butyl, linear or branched pentyl or hexyl, cyclopoentyl, cyclohexyl, cycloheptyl, cyclopentenyl, cyclohexenyl, cycloheptenyl, phenyl, naphthyl, dihydronaphthyl, tetrahydronaphthyl, benzyl, phenethyl, p-fluorophenethyl, o-methylphenethyl, p-methoxyphenethyl, 2,4-dichlorophenethyl, or cyclohexylethyl.

5. A compound as in claim 1 wherein $R_1$ is the sidechain of a naturally occuring L-amino acid.

6. A compound as in claim 1 wherein $R_1$ is methyl, isobutyl, methylthioethyl, carboxymethyl, carboxyethyl, amino-n-butyl, guanido-n-propyl, imidazol-4-ethyl, benzyl, 4-hydroxybenzyl, or 3-indolemethyl.

7. A compound as in claim 1 wherein $R_1$ is
($C_1$–$C_6$)-alkyl,
($C_1$–$C_6$)-alkyl, substituted by
   hydroxy,
   amino,
   phenylmercapto,
   guanido,
   phenyl,
   imidazol-4-ethyl, or
   indolemethyl.

8. A compound as in claim 1 which is N-[1-S-carboethoxy-3-(4-fluorophenyl)-propyl]-S-alanyl-1,2,3,4-tetrahydroisoquinoline-3-S-carboxylic acid.

9. A compound as in claim 1 which is N-[1-S-carboethoxy-2-(3-indolyl)-ethyl]-S-alanyl-1,2,3,4-tetrahydrodroisoquinoline-3-S-carboxylic acid.

10. A compound as in claim 1 which is N-(1-S-carboxy-3-phenyl-propyl)-S-(lysyl-1,2,3,4-tetrahydroisoquinoline-3-S-carboxylic acid.

11. A compound as in claim 1 which is N-(1-S-carboxy-2-cyclohexyl-ethyl)-S-isoleucyl-1,2,3,4-tetrahydroisoquiinoline-3-S-carboxylic acid.

12. A pharmaceutical preparation for the treatment of hypertension, said preparation comprising a hypotensively effective amount of a compound or salt as in claim 1 and a pharmaceutically acceptable carrier therefor.

13. A method for treating hypertension in a patient suffering therefrom, which method comprises orally, intravenously, or subcutaneously administering to said patient a hypotensively effective amount of a compound as in claim 1.

* * * * *

UNITED STATES PATENT AND TRADEMARK OFFICE
CERTIFICATE OF CORRECTION

PATENT NO. : 5,401,766
DATED : MARCH 28, 1995
INVENTOR(S) : Geiger et al.

PAGE 1 of 3

It is certified that error appears in the above-identified patent and that said Letters Patent is hereby corrected as shown below:

In Claim 1, column 229, after line 32 (after "50) naphthylaminocarbonyl,") and before line 55 (before "51) benzylaminocarbonyl or phenethylaminocar-"), please delete:

"61.1) halogen,
61.2) hydroxy,
61.3) acetoxy,
61.4) carboxy,
61.5) carboxamido,
61.6) sulfonamido,
61.7) nitro,
61.8) methyl,
61.9) ethyl,
61.10) methoxy,
61.11) ethoxy, or c) ($C_5$-$C_7$)-cycloalkyl- or cycloalkenyl, d) naphthyl, dihydronaphthyl, or tetrahydronapht-hyl, e) a 5-membered or 6-membered monocyclic heterocyclic structure, the hetero atoms of which are 1) 1 or 2 S atoms or 1 O atom and 0 or 1 N atom or 2) up to 4 N atoms, f) a heterocycle as defined in e) substituted by 1) halogen,

UNITED STATES PATENT AND TRADEMARK OFFICE
CERTIFICATE OF CORRECTION

PATENT NO. : 5,401,766
DATED : MARCH 28, 1995
INVENTOR(S) : Geiger et al.

It is certified that error appears in the above-identified patent and that said Letters Patent is hereby corrected as shown below:

2) oxo,

3) S-oxo,"

In Claim 1, column 230, after line 32 (after "61) phenyl mono- to di-substituted by") and before line 33 (before "4) hydroxy,"), please insert:

—61.1) halogen, 61.2) hydroxy, 61.3) acetoxy, 61.4) carboxy, 61.5) carboxamido 61.6) sulfonamido, 61.7) nitro, 61.8) methyl, 61.9) ethyl, 61.10) methoxy, 61.11) ethoxy, or

UNITED STATES PATENT AND TRADEMARK OFFICE
CERTIFICATE OF CORRECTION

PATENT NO. : 5,401,766

DATED : March 28, 1995

INVENTOR(S) : Geiger et al.

It is certified that error appears in the above-identified patent and that said Letters Patent is hereby corrected as shown below:

c) $(C_5-C_7)$-cycloalkyl- or cycloalkenyl, d) naphthyl, dihydronaphthyl, or tetrahydronapht-hyl, e) a 5-membered or 6-membered monocyclic heterocyclic structure, the hetero atoms of which are 1) 1 or 2 S atoms or 1 O atom and 0 or 1 N atom or 2) up to 4 N atoms, f) a heterocycle as defined in e) substituted by 1) halogen 2) oxo, 3) S-oxo,—.

Signed and Sealed this

Twenty-third Day of January, 1996

BRUCE LEHMAN

*Attest:*

*Attesting Officer*  *Commissioner of Patents and Trademarks*